United States Patent
Miller et al.

(10) Patent No.: US 9,169,300 B2
(45) Date of Patent: Oct. 27, 2015

(54) METHODS, CHIMERIC POLYPEPTIDES, POLYNUCLEOTIDES AND CELLS FOR PRODUCING BIOPLASTICS

(75) Inventors: Charles Miller, North Logan, UT (US); Ronald Sims, Logan, UT (US); Elisabeth Linton, Salt Lake City, UT (US)

(73) Assignee: Utah State University, North Logan, UT (US)

( * ) Notice: Subject to any disclaimer, the term of this patent is extended or adjusted under 35 U.S.C. 154(b) by 227 days.

(21) Appl. No.: 12/907,572

(22) Filed: Oct. 19, 2010

(65) Prior Publication Data

US 2011/0159555 A1   Jun. 30, 2011

Related U.S. Application Data

(60) Provisional application No. 61/252,967, filed on Oct. 19, 2009.

(51) Int. Cl.
| | |
|---|---|
| *C12P 7/62* | (2006.01) |
| *C07K 19/00* | (2006.01) |
| *C07H 21/00* | (2006.01) |
| *C12N 15/63* | (2006.01) |
| *C07K 14/195* | (2006.01) |

(52) U.S. Cl.
CPC .............. *C07K 14/195* (2013.01); *C12P 7/625* (2013.01); *C07K 2319/02* (2013.01)

(58) Field of Classification Search
None
See application file for complete search history.

(56) References Cited

PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q44013. Nov. 1, 1996.*
Accession P08715. Jan. 1, 1988.*
Linton et al., Translocation of green fluroescent protein by comparative analysis with multiple signal peptides, Biotechnol. J., vol. 6, pp. 1-10 (Aug. 10, 2011), Wiley-VCH Verlag GmbH & Co. KGaA, Weinheim.
Krogh et al., Hidden Markov Models in Computational Biology: Applications to Protein Modeling, UCSC-CRL-93-32, (Aug. 17, 1993).
Mackman et al., Genetical and functional organisation of the *Escherichia coli* haemolysin determinant 2001, Mol. Gen. Genet., vol. 201, pp. 282-288 (Jul. 15, 1985), Springer-Verlag.
Kozak, M., Point Mutations Define a Sequence Flanking the AUG Initiator Codon That Modulates Translation by Eukaryotic Ribosomes, Cell, vol. 44, pp. 283-292 (Jan. 31, 1986), Cell Press.
Reddy et al., Polyhydroxyalkanoates: An overview, Bioresource Technology, vol. 87, pp. 137-146, (2003), Elsevier Science Ltd.
Boffelli et al., Comparative Genomics at the Vertebrate Extremes, Nature Reviews Genetics, vol. 5, pp. 456-465 (Jun. 2004), Nature Publishing Group.
Spiekermann et al., A Sensitive, viable-colony staining method using Nile red for direct screening of bacteria that accumulate polyhydroxyalkanoic acids and other lipid storage compounds, Arch. Microbiol., vol. 171, pp. 73-80, (Nov. 11, 1999), Springer-Verlag.

* cited by examiner

*Primary Examiner* — Christian Fronda

(57) ABSTRACT

Methods of producing a bioplastic are disclosed. Furthermore, chimeric polypeptides useful to transport polyhydroxyalkanoates (PHAs) are disclosed, as are polynucleotides that code for the chimeric polypeptides, cells harboring the chimeric polypeptides and methods of transporting PHAs.

15 Claims, 27 Drawing Sheets

Figure 1A

| SEQ ID NO: | START | ALIGNMENT | END |
|---|---|---|---|
| 1 | 1 | MILTPEQVAAAQK----ANL----ET----LF----G-LTTKAFEGVEKLVELNLQVVKT | 43 |
| 2 | 1 | MILTPEQVAAAQK----ANL----ET----LF----G-LTTKAFEGVEKLVELNLQVVKT | 43 |
| 3 | 1 | MILTPEQVAAAQK----ANL----ET----LF----G-LTTKAFEGVEKLVELNLQVVKT | 43 |
| 4 | 1 | MILTPEQVAAAQK----ANL----ET----LF----G-LTSKAFEGVEKLVELNLQVVKA | 43 |
| 5 | 1 | MLTQEQIAAAHK----ANL----ET----FF----G-LTNKAFEGVEKLVELNLQVVKA | 42 |
| 6 | 1 | MLTQEQIAAAQK----ANL----ET----FF----G-LTNKAFEGVEKLVELNLQVVKA | 42 |
| 7 | 1 | MLTQEQIAAAHK----ANL----ET----FF----G-LTNKAFEGVEKLVELNLQVVKA | 42 |
| 29 | 1 | MLTQEQIAAAQK----ANL----ET----FF----G-LTNKAFEGVEKLVELNLQVVKA | 42 |
| 30 | 1 | MLTQEQIAAAQK----ANL----ET----FF----G-LTNKAFEGVEKLVELNLQVVKA | 42 |
| 31 | 3 | LLTPEQIAAAQK----ANL----ES----LF----G-LTTKAFEGVEKLIELNLQVVKS | 44 |
| 32 | 3 | LLTPEQIAAAQK----ANL----ES----LF----G-LTTKAFEGVEKLIELNLQVVKS | 44 |
| 33 | 3 | LLTPEQIAAAQK----ANL----ES----LF----G-LTTKAFEGVEKLIELNLQVVKS | 44 |
| 34 | 3 | LLTPEQFAAAQK----ANL----ET----LF----G-LTSKAFEGVEKLVELNLQVVKS | 44 |
| 35 | 3 | LLTPEQIAAAQK----ANL----ES----LF----G-LTTKAFEGVEKLIELNLQVVKS | 44 |
| 36 | 3 | LLTPEQIAAAQK----ANL----ES----LF----G-LTTKAFEGVEKLIELNLQVVKS | 44 |
| 37 | 3 | LLTPEQFAAAQK----ANF----ET----LF----G-LTTKAFEGVEKLVELNLQVVKS | 44 |
| 38 | 3 | LLTPEQIAAAQK----ANL----ES----LF----G-LTTKAFEGVEKLIELNLQVVKS | 44 |
| 39 | 3 | LLTPEQIAAAQK----ANL----ES----LF----G-LTTKAFEGVEKLIELNLQVVKS | 44 |
| 40 | 3 | LLTPEQFAAAQK----ANF----ET----LF----G-LTTKAFEGVEKLVELNLQVVKS | 44 |
| 41 | 5 | LLTPEQIAAAQK----ANI----ES----LF----G-LTTKAFEGVEKLIELNLQVVKS | 46 |
| 42 | 3 | LLTPEQFAAAQK----ANF----ET----LF----G-LTTKAFEGVEKLVELNLQVVKS | 44 |
| 43 | 1 | MLTPEQIAAAQK----ANI----ES----LF----G-LTTKAFEGVEKLIELNLQVVKS | 42 |
| 44 | 3 | LLTPEQIAAAQK----ANL----ES----LF----G-LTTKAFEGVEKLIELNLQVVKS | 44 |
| 45 | 3 | LLTPEQIAAAQK----ANI----ES----LF----G-LTTKAFEGVEKLIELNLQVVKS | 44 |
| 46 | 3 | LLTPEQIAAAQK----ANI----ES----LF----G-LTTKAFEGVEKLIELNLQVVKS | 44 |
| 47 | 5 | LLTPEQIAAAQK----ANI----ES----LF----G-LTTKAFEGVEKLIELNLQVVKS | 46 |
| 48 | 3 | LLTPEQFAAAQK----ANF----ET----LF----G-LTTKAFEGVEKLVELNLQVVKS | 44 |
| 49 | 5 | LLTPEQIAAAQK----ANI----ES----LF----G-LTTKAFEGVEKLIELNLQVVKS | 46 |
| 50 | 5 | LLTPEQIAAAQK----TNI----ES----LF----G-LTTKAFEGVEKLIELNLQVVKS | 46 |
| 51 | 3 | LLTPEQFAAAQK----ANF----ET----LF----G-LTTKAFEGVEKLVELNLQVVKS | 44 |
| 52 | 51 | TQEQIAAAQK----ANL----QY----FF----G-LTNKAFEGVPLLVELNLQVVKA | 90 |
| 53 | 3 | LLTPEQIAAAHK----ANL----ES----LF----G-LTSKAFESVEKLIELNVQVVKS | 44 |
| 54 | 3 | LLTPEQIAAAQK----ANL----ES----LF----G-LTTTAFDGIEKLIELNVQVVKS | 44 |
| 55 | 1 | MSLTPDQILSAQK----AHF----ET----LF----G-LTSKAFEGVEKLVELNVTASRA | 43 |
| 56 | 1 | MSLTPDQILSAQK----ANL----ET----LF----G-LTSKAFEGVEKLVELNVTASRA | 43 |
| 57 | 1 | MSLTPDQILSAQK----AHF----ET----LF----G-LTSKAFEGVEKLVELNVTASRA | 43 |
| 58 | 1 | MLTVEQVLASQK----ANV----ET----LL----G-LTSKAFEGMERIVELNMTASKA | 42 |
| 59 | 1 | MLTAEQVLASHK----ANI----ET----LF----G-LTSKAFEGVEKLVELNVQATKA | 42 |
| 60 | 1 | MSLTPEQILASHK----ANL----ET----LF----G-LTNKAFEGVEKLVELNVTASRA | 43 |
| 61 | 1 | MLTAEQLMASHK----ANI----ET----LF----G-LTQKAFEGVEKLVELNVQATKA | 42 |
| 62 | 1 | MSLTPEQILASHK----ANL----ET----LF----G-LTNKAFEGVEKLVELNVTASRA | 43 |
| 63 | 1 | MSLTPEQILASHK----ANI----ET----LF----G-LTNKAFEGVEKLVQLNVAASRA | 43 |
| 64 | 1 | MSLTPEQLIASQK----AHL----DT----LF----G-LTNKAFEGVEKLVELNVTASRA | 43 |
| 65 | 1 | MNLTPEQIAAAQK----ANL----ET----LS----G-LTNQALQSIEKLVELNLAIAKQ | 43 |
| 66 | 1 | MMTPEQFAAAQK----AQF----ET----FF----G-LAAKSMDNMEKLVDLNMQAVKT | 42 |
| 67 | 1 | MMTPEQFAAAQK----AQF----ET----FF----G-LAAKSMDNMEKLVDLNMQAVKT | 42 |
| 68 | 1 | MTLTAEQILASHK----ANI----ET----LF----G-LTSKAFEGVEKLVELNVSASRA | 43 |
| 69 | 1 | MSLTPEQLIASQK----AHL----DT----LF----G-LTNKAFEGVEKLVELNVTASRA | 43 |
| 70 | 1 | MALTADQILAAQK----ANL----ET----LF----G-LTTKAFEGVEKLVELNVTASKA | 43 |
| 71 | 1 | MTLTAEQILASHK----ANI----ET----LF----G-LTNKAFEGVEKLVELNVTASRA | 43 |

Figure 1B

| SEQ ID NO: | START | ALIGNMENT | END |
|---|---|---|---|
| 72 | 1 | MLTAEQIIAAHK----ANL----ET----LF----G-LTNKAFEGVEKLVELNLQVAKS | 42 |
| 73 | 1 | MSNSPEQFAAAGK----ANL----EA----LV----E-LGQKTFEGVEKLVELNLQAARS | 43 |
| 74 | 4 | FTPEQFAAAQK----SNV----SH----LF----A-LTNTAFEGFQKLTELNLQTLKA | 44 |
| 75 | 4 | FMPEQFAAVQK----SSL----NQ----LF----A-LTNMAFDGFQKLTELNLQAVRT | 44 |
| 76 | 2 | PEQFAAVQK----SSL----NQ----LF----A-LTNMAFDGFQKLTELNLQAVRT | 40 |
| 77 | 1 | MFTIPEQFSAATK----HQF----ESQLAILN----S-LTSTAFDSVQKIVDLNLNAAKS | 47 |
| 78 | 1 | MTAIPQQVLARQK----SAL----QT----LV----A-AQTAVFGGFEKLVDLNLKVVKA | 43 |
| 79 | 1 | MFAIPEQFSNATK----ANF----ES----QFAIFSS-LTSKAFEGMEKLVELNLTAAKA | 47 |
| 80 | 6 | EQFIATNK----ANL----QS----LT----D-LTTQAFAGVEKLVELNMAASKA | 43 |
| 81 | 1 | MALSSPDPAAVVK----ANL----DA----FF----G-LTGKIFEGAEKLAALNLQAVRS | 43 |
| 82 | 1 | MFAIPEQFSTATKNQFEAQL----AI----LN----S-FASTAFDSVQKIVDLNLNVVKS | 47 |
| 83 | 1 | MTYTAEQLIATTQ----SNV----DA----LE----G-LATQAFAGFEKLVELNLSASKA | 43 |
| 84 | 5 | TPDQVVAAQE----SSV----GY----WF----T-LTNIAVEGLQRLTELNLQTART | 44 |
| 85 | 1 | MNYSNDQLIATQK----SSV----EA----LA----G-LSEKAFASFEKLVELNMAASKA | 43 |
| 86 | 4 | LIPQQLVAAQQ----SSL----EA----LF----G-LTNKAFEGFEQLVALNLQVGKA | 44 |
| 87 | 1 | MTAIPQQVLDRQK----SAL----NT----LA----A-TQATLFAGFEKLVDLNLKVVKA | 43 |
| 88 | 4 | WSPEQFIKVQM----AGI----EA----LT----G-LTGKAFEGFEKLLELNLQAMKT | 44 |
| 89 | 4 | LIPQQLVTAQQ----SSL----ET----LF----G-LTSKVFEGFEKLVALNLQVSKA | 44 |
| 90 | 1 | MSAIPQQVLARQK----ATV----NS----LV----A-AQSAMFAGFEKLVDLNLKVVRA | 43 |
| 91 | 1 | MFSYQDQFSAATK----ANLQAHLDL----IN----S-LTAKAFEGVEKIVELNLSATKA | 47 |
| 92 | 1 | MSAIPQQVLDRQK----ASI----NT----FV----A-AQSAVFAGFEKLVELNMKVVRA | 43 |
| 93 | 1 | MFTTPEQFAAANK----ASV----DA----ML----T-LANTALASAERIAALNLNTARS | 43 |
| 94 | 1 | MNTTAEQFIATNK----ANL----QA----LQ----G-FTTQAFAGIEKLVELNLAASKA | 43 |
| 95 | 1 | MFATPEQFAATNK----ANV----ET----LL----T-LANNVFASAERFAALNLNTARS | 43 |
| 96 | 4 | FVTPEQFATANK----ANI----ET----LL----T-LANTAFASAERLAALNLNTARS | 45 |
| 97 | 4 | WTAEQCTKAQM----AGL----EA----MA----G-LTNKVLEGFEKVMDLNLQTMKM | 44 |
| 98 | 22 | LF----SQLASKTFEGVEKLVDLNLKAARS | 47 |
| 99 | 1 | MYATPEQFAATNK----AYV----ET----LL----T-IANTSFVSAEKLATLNLAAARA | 43 |
| 100 | 6 | EQIAAANK----AAL----DN----LV----T-LTQQAFKGIEQLVELNMQAARS | 43 |
| 101 | 5 | TPEQFISMQS----ANV----AV----AF----S-LTQQTFQYFEELAKLNLQAAKA | 44 |
| 102 | 1 | MTATPEQITAAAK----ANI----ET----LL----T-LANSAFSNVERLAALNLNTARS | 43 |
| 103 | 6 | PDQFISMQS----ANV----AV----AF----A-MTQQTFQYFEELAKLNLQAAKA | 44 |
| 104 | 4 | FTSDQFAALHK----TNL----AN----LA----M-MSKSTIDGFQKLTELNLKTAKS | 44 |
| 105 | 1 | MSINPEQLAAANK----AAI----DS----LL----S-VANTALASAERIATLNLETARS | 43 |
| 106 | 5 | TPDQFISMQS----ANV----AV----AF----S-LAQQTFQYFEELARLNLQAARA | 44 |
| 107 | 4 | IQTPEQFAAVGQ----ANL----EA----MM----S-LANSAIARAERLAELNLNTVRS | 45 |
| 108 | 1 | MWTVEQCKNVQA----AGL----DA----ML----G-LAKQGFDGFEKVVALNLQTTKT | 42 |
| 109 | 11 | AAQA----AAM----DI----VF----G-MTTKTLDAYQRLTELSMQTMKA | 44 |
| 110 | 3 | FFDSEKLQSAQK----ANL----DL----LQ----Q-ISGKVFESVEQLSQLQFKALRA | 44 |
| 111 | 1 | MLNTEQFAATNK----ANF----EA----MM----G-LTAKAFQGVEQLTALNLQVAKA | 42 |
| 112 | 7 | EKVESASK----SNL----DA----VQ----Q-LSSKLFEGAEELAKLQFKTIRA | 44 |
| 113 | 1 | MLKSEHVAATHK----TGL----EA----LA----E-LTSATLNSVEKLSELQFQTVRA | 42 |
| 114 | 1 | MLKSEHVAATHK----TGL----EA----LA----E-LTSAALNSVEKLSELQFQTVRA | 42 |
| 115 | 3 | VFAPEKFAADYQ----SGI----AA----WF----A-IARPAISGFEAVVELNLQVART | 44 |
| 116 | 7 | EAIAAAQK----AGV----EI----LY----G-LTSRTLEGFHKVAELNLQTMKW | 44 |
| 117 | 1 | MLKSEHVAATHK----TGL----DA----LA----E-LTGAALNSVEKLSELQFQTVRA | 42 |
| 118 | 7 | EQLAAAQK----ANA----EV----ML----A-LLRTAFNGVERLTALNVAASRE | 44 |
| 119 | 1 | MLKSEHVAATHK----TGL----EA----LA----E-LTSATLNSVEKLSELQFQTVRA | 42 |
| 120 | 7 | EKMESASK----SNL----DA----VQ----Q-LNSKIFESAEELYKLQFKTLRA | 44 |
| 121 | 7 | TPEQFASANK----ATV----DS----LL----S-VANAALASAERIAALNLNTARS | 46 |

Figure 1C

| SEQ ID NO: | START | ALIGNMENT | END |
|---|---|---|---|
| 1 | 44 | SFAEGVDNAKKALSAKDAQELLAIQAAAVQP--VA--EKTLAYTRHLYEIASETQSEFTK | 99 |
| 2 | 44 | SFAEGVDNAKKALSAKDAQELLAIQAAAVQP--VA--EKTLAYTRHLYEIASETQSEFTK | 99 |
| 3 | 44 | TFAENVDNAKKALSAKDAQELLAIQAAAVQP--VA--EKTLAYTRHLYEIASETQSEFAK | 99 |
| 4 | 44 | TLAENADNAKKALTAKDAQELLAIQASLVQP--VA--EKTLAYTRHLYEIASETQSEFTK | 99 |
| 5 | 43 | TLAENVEHAKKALTAKDAQELLSVQTAAVQP--LA--EKVLAYSRHLYEIASDTQTEFSK | 98 |
| 6 | 43 | TLAENVEHSKKALSAKDAQELLAVHTAAVQP--LA--EKVLAYNRHLYEIFSDTQTEFGK | 98 |
| 7 | 43 | TLAENVEHAKKALTAKDAQELLSVQTAAVQP--LA--EKVLAYSRHLYEIASDTQTEFSK | 98 |
| 29 | 43 | TLAENVEHSKKALSAKDAQELLAVHTAAVQP--LA--EKVLAYNRHLYEIFSDTQTEFGK | 98 |
| 30 | 43 | TLAENVEHSKKALSAKDAQELLAVHTAAVQP--LA--EKVLAYNRHLYEIFSDTQTEFGK | 98 |
| 31 | 45 | TLAEGQENAQRLLSVKDAQELIALQASLSQP--VA--EKVLSYGRHLYEIASSTQAEFAK | 100 |
| 32 | 45 | TLAEGQENAQRLLSVKDAQELIALQASLSQP--VA--EKVLSYGRHLYEIASSTQAEFAK | 100 |
| 33 | 45 | TLAEGQENAQRLLSVKDAQELIALQASLTQP--VA--EKVLSYGRHLYEIASATQAEFAK | 100 |
| 34 | 45 | TIAESQENAQRALSVKDAQELLALQAGLTQP--VA--EKVLSYGRHLYEIASATQAEFAR | 100 |
| 35 | 45 | TLVESQENAQRLLSAKDAQELLALQASLTQP--VA--EKVLSYGRHLYEIASSTQAEFAK | 100 |
| 36 | 45 | TLAEGQENAQRLLSVKDAQELIALQASLTQP--VA--EKVLSYGRHLYEIASATQAEFAK | 100 |
| 37 | 45 | TLAESQENAQRALSVKDAQELLALQASLAQP--VA--EKALSYGRHVYEIVSATQGEFTR | 100 |
| 38 | 45 | TLTESQENAQRLLSVKDAQELIALQASLSQP--VA--EKVLSYTRHLYEIASSTQAEFAK | 100 |
| 39 | 45 | TLTESQENAQRLLSVKDAQELIALQASLSQP--VA--EKVLSYGRHLYEIASSTQAEFAK | 100 |
| 40 | 45 | TLAESQENAQRALSVKDAQELLALQASLAQP--VA--EKALSYGRHVYEIVSATQGEFTR | 100 |
| 41 | 47 | TLAESQENVQRALSVKDAQELLALQASLTQP--IA--EKVLAYGRHVYEIASATQAEFAK | 102 |
| 42 | 45 | TLAESQENAQRALSVKDAQELLALQASLAQP--VA--EKALSYGRHVYEIVSATQGEFAR | 100 |
| 43 | 43 | TLAESQENVQRALSVKDAQELLALQASLTQP--IA--EKVLAYGRHVYEIASATQAEFAK | 98 |
| 44 | 45 | TLTESQENAQRLLSVKDAQELIALQASLSQP--VA--EKVLSYSRHLYEIASATQAEFAK | 100 |
| 45 | 45 | TLAESQENVQRALSVKDAQELLALQASLTQP--IA--EKVLAYGRHVYEIASATQAEFAK | 100 |
| 46 | 45 | TLAESQENVQRALSVKDAQELLALQASLTQP--IA--EKVLAYGRHVYEIASATQAEFAK | 100 |
| 47 | 47 | TLAESQENVQRALSVKDAQELLALQASLTQP--IA--EKVLAYGRHVYEIASATQAEFAK | 102 |
| 48 | 45 | TLAESQENAQRALSVKDAQELLALQASLAQP--VA--EKALSYGRHVYEIVSATQGEFAR | 100 |
| 49 | 47 | TLAESQENVQRALSVKDTQELLALQASLTQP--IA--EKVLAYGRHVYEIASATQAEFAK | 102 |
| 50 | 47 | TLAESQENVQRALSVKDAQELLALQASLTQP--IA--EKVLAYGRHVYEIASATQAEFAK | 102 |
| 51 | 45 | TLAESQENTQRALSVKDAQELLALQASLAQP--VA--EKALSYGRHVYEIVSATQGEFAR | 100 |
| 52 | 91 | TLAENVEHSKKALSAKDAQELLAVHTAAVQP--LA--EKVLAYNRHLYEIFSDTQTEFGK | 146 |
| 53 | 45 | TLAESQENAQRALSAKDAQELIALQASFAQP--VA--EKMLAYGRHLYDIASTTQAEFAK | 100 |
| 54 | 45 | TLAETQENAQRLLSVKDAQELIALQASLTQP--VA--EKVLAYGRHVYEIASATQAEFAK | 100 |
| 55 | 44 | ALAEAAQHTQAVLSVKDAQELLTLQAGLFQP--LA--EKTASYSRHLYDIASNTAGEFNK | 99 |
| 56 | 44 | ALTEAAQHTQAVLSVKDAQELLSLQANLFQP--LA--EKTAAYSRHLYDIASGTGAELAK | 99 |
| 57 | 44 | ALTEAAQHTQAVLSVKDAQELLTLQAGLFQP--LA--EKTASYSRHLYDIASNTAGEFNK | 99 |
| 58 | 43 | ALAETSETAKAFLSAKDAQELLALQSSLMQP--LA--EKTAAYSRHLYDIATGSSAEFSK | 98 |
| 59 | 43 | ALAETANHTQAVLGAKDAQELLALQAGLVQP--LA--EKTAAYSRHIYDIATAASAELSK | 98 |
| 60 | 44 | ALAEAASHTQAVLSAKDAQELLALQASLFQP--LA--EKALAYSRHLYDIASGMGAEFGK | 99 |
| 61 | 43 | ALAETANNAQAVLNAKDAQELLALQASMVQP--LA--EKTAAYSRHLYDIAQSAGAEFSK | 98 |
| 62 | 44 | ALAEAASHTQAVLSTKDAQELLALQASLFQP--LA--EKAVAYSRHLYDIASGTGAEFGK | 99 |
| 63 | 44 | ALTEAATHAQAVLSVKDAQELLALQAGLFQP--LA--EKAAAYSRHVYEIASGTGAEFGK | 99 |
| 64 | 44 | TLSEAATHTQALLSVKDAQELLSLQAAFFQP--LA--EKTAAYNRHLYEIASGTTAEFGR | 99 |
| 65 | 44 | SLSDSVNNAKKALEVKDIQQLLAHQAETVQP--IA--EKIISYSRHLYELAHETQESFTK | 99 |
| 66 | 43 | SLQESADHTMALLSVKDLQELSTLQSGWMQP--MA--EKVLSYSRHAYEIASGAQAELAK | 98 |
| 67 | 43 | SLQESADHTMALLSVKDLQELSTLQSGWMQP--MA--EKVLSYSRHAYEIASGAQAELAK | 98 |
| 68 | 44 | ALSEVANHAQAVLGVKDAQELLALQASLFQP--LA--EKTAAYSRHLYDIASGTGAEFGK | 99 |
| 69 | 44 | TLSEAATHTQALLSVKDPQELLSLQAAFFQP--LA--EKTAAYNRHLYEIASGTTAEFGR | 99 |
| 70 | 44 | ALSEAQSTAQAALNVKDAQELLTLQASLFQP--LA--EKTAAYSRHLYDIAQGTGAEFTK | 99 |
| 71 | 44 | ALAEAANHTQALLGVKDAQELLALQAGLFQP--LA--EKTAAYSRHLYDIASGTGAEFTR | 99 |

Figure 1D

| SEQ ID NO: | START | ALIGNMENT | END |
|---|---|---|---|
| 72 | 43 | GLGEVAEHAKATLSAKDAQELLALQANLLQP--AA--EKAAAYSRHLYDIASGTNAEVSK | 98 |
| 73 | 44 | NMGEGVDAAKALFAVKDAQELFALQSSLMQP--AT--EKATAYGRQVYEIAQSTQAEVAK | 99 |
| 74 | 45 | TLSEGQENVQAALAGKDLREVFAAQGNLAQP--AA--EKAVAYARHVYEIASNTQAELSK | 100 |
| 75 | 45 | TLAEGQGNIEAVLAGKDLREVFAVQGNLAQP--AA--EKAVAYARHVYEIASNTQVELTK | 100 |
| 76 | 41 | TLAEGQGNIEAVLAGKDLREVFAVQGNLAQP--AA--EKAVAYARHVYEIASNTQVELTK | 96 |
| 77 | 48 | SLQESSAAAQKLATAKDPQEFFSLSAAHAQP--NA--EKALAYGRHLASIASSTQAEFTK | 103 |
| 78 | 44 | TLDEVAQKSQQAVELKDVQDAASFTSALVQP--SA--EKALAYGKHVYDIINTVQADLAK | 99 |
| 79 | 48 | SLEESSITTRQLLSAKDPQEFFSLTAAQAQP--TA--EKAMSYSRQVAAIAAGTQAEFTK | 103 |
| 80 | 44 | ALSESFTHVQTVMAIKDPKELMALQSGLLKP--MA--DKTAAYAQHLQTIVTDSGAEFTK | 99 |
| 81 | 44 | TLAEAQENMTKAPGTTDPLQWFALQSGLTGP--FA--ENSLSYGRQVFDIASTTQAELTQ | 99 |
| 82 | 48 | SLQESSAAAQQLISAKDPQEFFSLSAAQAQP--TA--EKALAYSRHLVGITTSTQAEFAK | 103 |
| 83 | 44 | ALAESFSNARALAGAKDPQQLLALQAGLFQP--LA--EKSVSYGNQVYSVAAETGAVFTK | 99 |
| 84 | 45 | TVADSQDNVRALFAGRDLRDVFAVQANLAQP--AA--EKAIAYARNVYEIASNTQAELTK | 100 |
| 85 | 44 | LLGESISHLQALSEIKDPKELLSLQSELVKP--MA--EKAASYSRHLYEILSGASAEFTK | 99 |
| 86 | 45 | VLAENQEIVTKALSAGNPGALFALQASLSQP--VA--EKVVAYGRRVHEIVSGVQSEITA | 100 |
| 87 | 44 | TLDEVAQTSQQAIAVKDPQEAAAFATALVQP--GA--EKALAYGKHVYDIVAGVQGELAK | 99 |
| 88 | 45 | ALADSREGARKALSAKDPQELVELQIALFQP--AA--DNVLAYRRQLYDILAATRAEFEK | 100 |
| 89 | 45 | AIVQNHENVTKAMSGGNPGELLARQASLSQP--AA--EKAVAYGRQVHEILVGVQSEISA | 100 |
| 90 | 44 | TLDEVAQQSQQAAELKDPQDVASFTSGLVQP--GA--EKALAYGKHVYDIVAGVQAELAQ | 99 |
| 91 | 48 | TLEEAAAAKQLAGAKDPQELLSLATAQAQP--GA--EKATAYGRHLAGIVSSTQAEFTK | 103 |
| 92 | 44 | TLDEVAQKSQQASEVKDPQEAAAFASGLLQP--GA--EKAMAYTKHVYDIVAGVQGSLVK | 99 |
| 93 | 44 | MLEDGVANAKAMLGAKDPQEFFSVQASLAQP--SL--EKAVAYTRSVYEISAQSKEEITK | 99 |
| 94 | 44 | ALGESFNHVQAALGAKDAQQLLALQSGLVKP--LT--EKSAAYVQHVQTIVTGSGAEFTK | 99 |
| 95 | 44 | ILEDSIANSKALLGAKDVQELVSLQAALAQP--LV--EKAVAYNRSVYEIASQGQEEISK | 99 |
| 96 | 46 | LLEDGVANTKALLAAKDVQELVNLQVSLAQP--IV--EKAVAYARSVYEISSQSQEEMSK | 101 |
| 97 | 45 | TLAHNREGVMKALSVQNPQELIELQIELFQP--AA--DKVLEYRRQLHDILAATRAEFEK | 100 |
| 98 | 48 | TLEESQAAAQKLFAAKDPQEFFALTSAHAQP--TL--EKSVAYGRHLSGIFSSTQAELTK | 103 |
| 99 | 44 | VLEDGVANAKSLLAVKDAHELVNLQASLAQP--SV--EKLVAYSRHVYDIAHQAQQEIAG | 99 |
| 100 | 44 | SIDDSVEKAKAALGAKDPQEFMTSLQANLQP--AQ--DKAVAYGRQVADIAAATQAEVSK | 99 |
| 101 | 45 | TLAESEQAWQMAMSGKTPVELLVHQASNAKP--VA--EKVLSYNSHMLEIANAAQAEFLK | 100 |
| 102 | 44 | VLEDGVANTKALLAAKDVQEFVSLQTSLAQP--LI--EKAVAYNRSVYEIASQSQEELSK | 99 |
| 103 | 45 | TLAESEQAWQLATSGKTPVELFVHQAGNVKP--VA--EKVLSYNSHLFGIANSVQEFLK | 100 |
| 104 | 45 | ALTEGQENLKAVLGGKDLRDVLAVQGSLAQP--TT--EKAISYARQVCEIAAQAQAELAR | 100 |
| 105 | 44 | VIEDSVSGAKALMGAKDPQEALSIQASLTQP--NV--EKAVAYSRSIYEISAQTQEQLAK | 99 |
| 106 | 45 | TLAESEQAWQLAVSGKTPMELFVYQAGNAKP--VA--EKVLSYNSHLFGIANSAQEFLK | 100 |
| 107 | 46 | VLEDSVATTRKLAEAKDPQQLAKLQGELTKP--ML--DKAVAYARSVQEIATEGQQEVSN | 101 |
| 108 | 43 | SLALTREGVLKILSAQSPRELAELQIEWLQP--LT--DHALTYRHQLQDILAATRAEFAK | 98 |
| 109 | 45 | TLADNQETVRQAFAAKSPQEFFALQVTAVEP--AA--EKARAFFQQVQEIAATTREEFQK | 100 |
| 110 | 45 | SSGEQFDSLRKLLSVRDPQAFAELQASFAQP--AAQAERLLEFNREVYDLVSSTQADIAK | 102 |
| 111 | 43 | GLDEAAETGRAALSAKDPQALLALQAAPLQA--AA--EKATAYGKQVYGIVAGIKADVEK | 98 |
| 112 | 45 | ATDDNFENLRKIISVRDPQAFLELQASFFKPNEQA--ERLVEFSRQTYDLISRFQAEVTR | 102 |
| 113 | 43 | SLEDSAEQGKRAFGARSLHELTELQSESAQP--T---EKLVAYGRHLYQIAAGTHAEWRK | 97 |
| 114 | 43 | SLEDTAEQGMRAFDARSLHELTALQSEASQP---A--EKLVAYGRHLYQIAAGTHAEWRK | 97 |
| 115 | 45 | ALAEYEDKLKNAFNASNPAAGFAQQVAAPQE--AA--GKAAAYGRHLFDIAVSTQAEWAK | 100 |
| 116 | 45 | TLAETQACTRKAFEAKNDGDLPVMEARILLP--LA--EKAQAYCRQGLEIAAETRADLAT | 100 |
| 117 | 43 | SLEDSTEQSKRAFDARSLHELTALQSEVSQP--T---EKLMAYGQHLYQIAAGTHAEWRK | 97 |
| 118 | 45 | FFNNSVANSQQLLGAKDAAAVAKLNAELAQP--NL--EKLVEYSRNVYELTTDVQKELTS | 100 |
| 119 | 43 | SLEDTAEQGKRAFGARSLHELTELQSESAQP--T---EKLVAYGRHLYQIATGTHAEWRK | 97 |
| 120 | 45 | AADDNFESLRKLLSVRDPQAFLELQASFFKPNEQA--ERLVEFSRQTYDLISRFQAEVTR | 102 |
| 121 | 47 | VLEDSVSGTKALLGAKDVQEAISIQASLAQP--NV--EKAVAYSRSVYEISAQAQEELSK | 102 |

Figure 1E

| SEQ ID NO: | START | ALIGNMENT | END |
|---|---|---|---|
| 1 | 100 | VAEAQLAEGSKNVQALVENLAKNAPAG-SESTVAIVKSAISAANNAYESVQKATKQAVEI | 158 |
| 2 | 100 | VAEAQLAEGSKNVQALVENLAKNAPAG-SESTVAIVKSAISAANNAYESVQKATKQAVEI | 158 |
| 3 | 100 | VAEAQLAEGSKNVQALVENFAKNAPAG-SESTVAIVKSAISAANNAYESVQKATKQAVEI | 158 |
| 4 | 100 | VAEAQLAEGTKNVQALVDNLAKNAPAG-SESTVAIVKSAISAANNAYESVQKATKQAVEM | 158 |
| 5 | 99 | AAEAQIAENSRKLQALVDNVSKNAPAG-SESAVALVKSALSAANNAYDSVQKATKQAVEL | 157 |
| 6 | 99 | VAETQIAEGSRKLQALIDNVSKNAPAG-SESAVALVKSALSAANNAYDSVQKATKQAVEL | 157 |
| 7 | 99 | AAEVQIAENSRKLQALVDNVSKNAPAG-SESAVALVKSALSAANNAYDSVQKATKQAVEL | 157 |
| 29 | 99 | VAETQIAEGGRKLQALIDNVSKNAPAG-SESAVALVKSALSAANNAYDSVQKATKQAVEL | 157 |
| 30 | 99 | VAETQIAENGRKLQALIDNVSKNAPAG-SESAVALVKSALSAANNAYDSVQKATKQAVEL | 157 |
| 31 | 101 | VAEAQFEEQNKKVQALVDNVAKNAPAG-SETAVAALKSALNAANTTYETVQKATKQAVEI | 159 |
| 32 | 101 | VAEAQFEEQNKKVQALVDNVAKNAPAG-SETAVAALKSALNAANTTYETVQKATKQAVEI | 159 |
| 33 | 101 | VAEAQFEEQNRKVQALVDNVAKNAPAG-SETAVAALKSALNAANTTYETVQKATKQAVEI | 159 |
| 34 | 101 | VAEAQYEEQNKKVQALVENVAKNAPAG-SETAVAVIKSAITAANTTYETVHKATKQAVEI | 159 |
| 35 | 101 | VAEAQFEEQNRKVQALVDNVAKNAPAG-SETAVAALKSALNAANTTYETVQKATKQAVEI | 159 |
| 36 | 101 | VAEAQFEEQNKKVQALVDNVAKNAPAG-SETAVAALKSALNAANTTYETVQKAAKQAVEI | 159 |
| 37 | 101 | VAEAQFEEQNRKVQALVENVAKNAPAG-SETAVAVMKSAITAANTTYETVHKATRQAVEI | 159 |
| 38 | 101 | VAEAQFEEQNKKVQALVDNVAKNAPAG-SETAVAALKSALNAANTTYETVQKAAKQAVEI | 159 |
| 39 | 101 | VAEAQFEEQNKKVQALVDNVAKNAPAG-SETAVAALKSALNAANTTYETVQKATKQAVEI | 159 |
| 40 | 101 | VAEAQFEEQNRKVQSLVENVAKNAPAG-SETAVAVLKSAITAANTTYDTVHKATKQAVEI | 159 |
| 41 | 103 | VAEAQYEEQNRKVQALVDNVAKNAPAG-SETAVAALKSAINAANTTYETVQKAAKQAVEI | 161 |
| 42 | 101 | VAEAQFEEQNRKVQSLVENVAKNAPAG-SETAVAVIKSAITAANTTYETVHKATKQAVEI | 159 |
| 43 | 99 | VAEAQYEEQNRKVQALVDNVAKNAPAG-SETAVAALKSAINAANTTYETVQKAAKQAVEI | 157 |
| 44 | 101 | VAEAQFDEQNKKVQALVDNVAKNAPAG-SETAVAALKSALNAANTTYETVQKAAKQAVEI | 159 |
| 45 | 101 | VAEAQYEEQNRKVQALVDNVAKNAPAG-SETAVAALKSAINAANTTYETVQKAAKQAVEI | 159 |
| 46 | 101 | VAEAQYEEQNRKVQALVDNVAKNAPAG-SETAVAALKSAINAANTTYETVQKAAKQAVEI | 159 |
| 47 | 103 | VAEAQYEEQNRKVQALVDNVAKNAPAG-SETAVAALKSAINAANTTYETVQKAAKQAVEI | 161 |
| 48 | 101 | VAEAQFEEQNRKVQSLVENVAKNAPAG-SETAVAVMKSAITAANTTYETVHKATKQAVEI | 159 |
| 49 | 103 | VAEAQYEEQNRKVQALVDNVAKNAPAG-SETAVAALKSAINAANTTYETVQKAAKQAVEI | 161 |
| 50 | 103 | VAEAQYEEQNRKVQALVDNVAKNAPAG-SETAVAALKSAINAANTTYETVQKAAKQAVEI | 161 |
| 51 | 101 | VAEAQFEEQNRKVQALVENVAKNAPAG-SETAVAVMKSAITAANTTYETVHKATRQAVEI | 159 |
| 52 | 147 | VAETQIAENGRKLQALIDNVSKNAPAG-SESAVALVKSALSAANNAYDSVQKATKQAVEL | 205 |
| 53 | 101 | VAEAQFQEQNLKVQALVDNVAKNAPAG-SETAVAALKSAINAANTTYETVQKATKQAVEI | 159 |
| 54 | 101 | VAEAQYEEQNKKVQALVDNVAKNAPAG-SETAVAALKSALNAASTTYETVQKAAKQAVEI | 159 |
| 55 | 100 | TLEAQSTEARKNFNALLDNTTKNAPAG-SESAVAMVKSAVSAANNAFESVQKAVKQASDM | 158 |
| 56 | 100 | TFESQASDLQKNFSALVDTTAKNAPAG-SETAVAVMKSAVSAANNAFESVQKAVKQASDL | 158 |
| 57 | 100 | ALEVQSTEARKSFNSLLDNSTKNAPAG-SESAVAMVKSAVSAANNAFESVQKAVKQASDM | 158 |
| 58 | 99 | AFEAQTAEAQQKFMGLVDNVAKNAPAG-SESAVAVMKSAVAAASNAMESVQKAVQQATEV | 157 |
| 59 | 99 | TFEGQAADAQKKFVGIVDNAAKNAPAG-SETAVAVMKSAVAAANNAFESVQKAVKQASDI | 157 |
| 60 | 100 | TFEAQAAEVQRNFTNLVDSAAKNAPAG-SETTVAVFKSAVSAANNAFESVQKAVKQASDV | 158 |
| 61 | 99 | TLEGQTAEAQKKFADLVESATQNAPAG-SETAVTMMKSAMTAANSAFESVQKAVKQAGDM | 157 |
| 62 | 100 | TFEAQAAEVQRNFTNLVDSAAKNAPAG-SETTVAVFKSAVSAANNAFESVQKAVKQASDV | 158 |
| 63 | 100 | AFESQAAEAQRNFSNLVDTAAKNAPAG-SETTVAVFKSAVSAANNAFESVQKAVKQASDV | 158 |
| 64 | 100 | AFEAQAAEMQRNFSNLVDTAARNAPAG-TETGVAVFKSAVSAANNAFETVQKAVKQASDA | 158 |
| 65 | 100 | SAEKEFQAGQEKMNALVEEWTKNAPAG-SDVAVQALKQAIASANNVYETSQKAVKHAVEV | 158 |
| 66 | 99 | TAESQISETHKKFMDLAESAAKNAPAG-SETAVAMMKSAMNAANNAYDSVQKVTKQAAEA | 157 |
| 67 | 99 | TAESQISETHKKFMDLAESAAKNAPAG-SETAVAMMKSAMNAANNAYDSVQKVTKQAAEA | 157 |
| 68 | 100 | AFETQASDAQKAFATLVDSAAKNAPAG-SETAVAVMKSAVSAATNAFESVQKAVKQASDV | 158 |
| 69 | 100 | AFEAQAAEIQRNFTNLVDTAARNAPAG-TETGVAVFKSAVSAANNAFETVQKAVKQASDA | 158 |
| 70 | 100 | AFEAKAAEAQQTFVGLVDSASKNAPAG-SETAVAVLKSAVAAANNAFESVQKAVKQASDV | 158 |
| 71 | 100 | AFEVQATDAQRSFTNLVDSAAKNAPAG-SETAVAVMKSAVSAANNAFESVQKAVKQASDV | 158 |

Figure 1F

| SEQ ID NO: | START | ALIGNMENT | END |
|---|---|---|---|
| 72 | 99 | IAEGKISEAQKSFLAVVDTAIKNAPAG-TENAAALVKSAVAAANNALESVTKAAKQAQDV | 157 |
| 73 | 100 | LAEAQYAALQQNIAALVDTAVKNAPAG-SEGAVAMVRQAVTAANTALENAQKAAKQAVGV | 158 |
| 74 | 101 | AVEAQYEQHNRNVQAFVDTFVKNAPAG-SEALTALLQSGVAAASTTYQSFQDAAKQTAEV | 159 |
| 75 | 101 | AVEGQYEQHNRNVQAFVDNFVKNAPAG-SEAITALLQSSVAAASSTFQSFQDAAKQTAEV | 159 |
| 76 | 97 | AVEGQYEQHNRNVQAFVDNFVKNAPAG-SEAITALLQSSVAAASSTFQSFQDAAKQTAEV | 155 |
| 77 | 104 | AAETQIAETNRKVLSLIDELSKNAPAG-SENAISILKSAIGNANAGYEQLSKTTKQAVEA | 162 |
| 78 | 100 | LAEAQIAEGQQHVQEAVEQFSKNAPNG-SESAVALLKSSLATANNAYESLTKAAKQAAEV | 158 |
| 79 | 104 | AAEEQIAETNRKVISLVDEVTKNAPAG-SENVVSIIKATIGNANAGYEQFSKTAKQAAET | 162 |
| 80 | 100 | AVEAKTAEAQKAFGDVLENLTKNAPAG-SETIVTAFKDALSSGQNAIESVQTQTKKAVET | 158 |
| 81 | 100 | FAQAQYERHNARVQAFVEEAAKNAPAG-SEAAIAAWKSATSATSTLYETLQKTGQQAVQA | 158 |
| 82 | 104 | AAETQIAETNRKVLSLVEELSKNAPAG-SENAIALIKSAIGNANAGYEQLSKTTKHAVET | 162 |
| 83 | 100 | TFEAKVDEAKKAFAVAVDNMTKNAPAG-TEAAVAAFKSAVSASQNAIETAQGTAKKAVEL | 158 |
| 84 | 101 | AVEARYEQHSRNMQSFVDTFVKNAPAG-SEAITALLQSSVAAASSTYQSIQSAAKQTAEA | 159 |
| 85 | 100 | TLESTSAESQKTVTELLETSLKNAPAG-SEAAVAVIKSAITAGNTAVETAQKSAKQAAQL | 158 |
| 86 | 101 | AATAQGQQFQRDAQGFVESLQKNTPAG-SESAVAAWNSVLSAANATYESANKAAKQFV | 157 |
| 87 | 100 | LAEAQIAEGQQQVADAVEQFSKSAPTG-SESAVALLKSSLATANGAYESLTKAAKQAAEV | 158 |
| 88 | 101 | VAEVQYTAGKQGLHDFLGSVVSQTPSGAAAAPLAAWQEAVSATTTLYESMQTTAKQAVQA | 160 |
| 89 | 101 | AATAQGQQFQREAQGFVENLTKNAPAG-SESAIAAWSSAFSTASTVYESANKAAKQFV | 157 |
| 90 | 100 | LAEAQIAEGQQQLTEAVEQFSKNAPTG-SESAVALIKSSLATANSAYDSLTKAAKQAAEV | 158 |
| 91 | 104 | AAEAQIAETSRKLSALIDEITKNAPPG-SEQAVSILKATLTNANAAYEQLSKNSKQAVET | 162 |
| 92 | 100 | LTEEQIAESQQQLSEAVDQLSKNAPAG-SESAVALIKSSLATATSAYDSVTKAAKQAAEV | 158 |
| 93 | 100 | LLEAQFSDFQKQTLALLEKATKNAPVG-SDVAVSAVKSAIASATSAFDSMNKAAKQVADI | 158 |
| 94 | 100 | AVEAKTAEAQKAFDSVLENLTKNAPAG-SETAVAAFKNALTSGQNALES | 147 |
| 95 | 100 | LVETQIAEVNKNLSLALDKAAKSAPAG-SDVAVAAVKSAIAAANSAYDSVSKAAKQVAEI | 158 |
| 96 | 102 | VFEGQVAELNKGVATALDKAAKSAPAG-SDVAVAAVKSAIAAANSAYDSMSKAAKQVAEI | 160 |
| 97 | 101 | IAEVQYTTSKGQLQGLIDSAVSNAPSG-STAPLAAWQEAVKATTALYESMQSTAKQAVEV | 159 |
| 98 | 104 | AAEAQIAEVNRKVVAMIDEVAKNAPAG-SEQAVSVLKSAIGNMSAGYEQFTKNAKQAAEV | 162 |
| 99 | 100 | ILESQLAEINKNVASALDKAAKSAPAG-SDVAVAAVKSALAAANSAYDSMNKAAKQVAEI | 158 |
| 100 | 100 | LAEAQVKAVQEQFQSLVDTAVKNAPAG-SESAVAAVKSAIANTTAAFDSVQKAAKQAASA | 158 |
| 101 | 101 | IFEDRFAQSNTKMQTVFEDLARNAPAG-SELAVTAFKSAVSSAGAAYDAMRKATAQAIAM | 159 |
| 102 | 100 | LFEGQVAELNKSLAAALDKAAKSAPAG-SDVAVAAVKSAIAAANSAYDSVSKAAKQVAEI | 158 |
| 103 | 101 | LFEDRFAQSNAKMQTVVDDFARNAPAG-SEVAVTVFKSAVSSAGAAYDAMRKATAQAIAM | 159 |
| 104 | 101 | AVEEQYEQHHRNLQAFVDTFVKNAPAG-SEAVSALLQSTVDAAGNTYRSAQAISKQMSDV | 159 |
| 105 | 100 | MVEAQFGDFQKSVASMLEKAAKAAPGG-SDVAVNAFQSAIAAATSTFENMRKAAQQVTEL | 158 |
| 106 | 101 | LFEDRFAQSNAKMQTAMDDFSRNAPAG-SEVAVTVFKSAVSSAGVAYEAMRKATAQAIAV | 159 |
| 107 | 102 | LFEKQIADLNKRFHDMLEQAAKQAPAG-SEGVFEAVRSAMNTANSLYDNASKAARQAAEV | 160 |
| 108 | 99 | VAEAQYAASRGQLQDFFEGAVSNAPSG-SASPLGAWQEAIKATTMLFESMQSTTKQAMEV | 157 |
| 109 | 101 | VAAAQYETNKQTVQQIFEKLAQNVPAG-SEGPFSAWQAAMTSGASLCESMQQSTKQAIEL | 159 |
| 110 | 103 | LAERQVEAGTKQVRELVDVIAKNAPAG-AEPAVAVLKSALESAGSVYESAQKAAKQAAEI | 161 |
| 111 | 99 | LAAEQAAAAQSSFVALVESAGKNAPEG-AVNGIALFKSSLATMNNAFDGLQKAGRQAAET | 157 |
| 112 | 103 | LTERQIEIGTQQAQEIVEEICKNAPAS-AEPVVSVFKSAVEGAGNVYESAQRAAKQASEI | 161 |
| 113 | 98 | VAQASANEQCRIALAWVDDYAKQAVPG-SEPAISFMRSTISATQRACDAWQDASVHAIHL | 156 |
| 114 | 98 | VAQTRANEQCRIALAWVDDYAKQAVPG-SEPAVSFMRSTITAAQRACDAWQDASTHAIHL | 156 |
| 115 | 101 | VAQAQYEETDKRVKDVVGELTKHAPAG-SGAVVAALNSALSAATAAADSMRAATGQAIEA | 159 |
| 116 | 101 | VVEAQYEQSKRVMQDYIDAVERVAPSG-SGTAMAAWKSALTATTSFLDAMQRTAKQVGNI | 159 |
| 117 | 98 | VAQTRANEQCRIALAWVDDYAKQAVPG-SEPAISFMRSTITATQRACDAWQDASTHAIHL | 156 |
| 118 | 101 | VIEAQYGNLTKNAASAVQKASASAPIG-GDVFAAAMNSVINASSQAFESLNSVTRQLSEI | 159 |
| 119 | 98 | VAQASANEQCRIALAWVDDYAKQAVPG-SEPAISFMRSTIAATQRACDAWQDASVHALHL | 156 |
| 120 | 103 | LTERQIEIGTQQAQEIVEEICKNAPAS-AEPVVSVFKSAVEGAGNVYESAQKAAKQASEI | 161 |
| 121 | 103 | SIEAQFGGFQKQVADLLDKAAKSAPAG-SDVAVAAVKSAIAAANSAFDNLNKAAKQVAEI | 161 |

Figure 1G

| SEQ ID NO: | START | ALIGNMENT | END |
|---|---|---|---|
| 1 | 159 | AETNF-QAAATAATKAAQQASATARTATAKKTTAA | 192 |
| 2 | 159 | AETNF-QAGGYGCHQGC | 174 |
| 3 | 159 | AETNF | 163 |
| 4 | 159 | AESNF-QAAATAATKAAQQASATAR | 182 |
| 5 | 158 | AESNF-H | 163 |
| 6 | 158 | AESNF-H | 163 |
| 7 | 158 | AESNF-H | 163 |
| 29 | 158 | AESNF-H | 163 |
| 30 | 158 | AESNF-H | 163 |
| 31 | 160 | AETNF | 164 |
| 32 | 160 | AETNF | 164 |
| 33 | 160 | AETNF | 164 |
| 34 | 160 | AESNF | 164 |
| 35 | 160 | AETNF | 164 |
| 36 | 160 | AETNF | 164 |
| 37 | 160 | AESNF | 164 |
| 38 | 160 | AETNF | 164 |
| 39 | 160 | AETNF | 164 |
| 40 | 160 | AESNF | 164 |
| 41 | 162 | AETNF | 166 |
| 42 | 160 | AESNF | 164 |
| 43 | 158 | AETNF | 162 |
| 44 | 160 | AETNF | 164 |
| 45 | 160 | AETNF | 164 |
| 46 | 160 | AETNF | 164 |
| 47 | 162 | AETNF | 166 |
| 48 | 160 | AESNF | 164 |
| 49 | 162 | AETNF-NAAAAVATKAANTAAAASRRSSTGKT | 192 |
| 50 | 162 | AETNF | 166 |
| 51 | 160 | AESNF | 164 |
| 52 | 206 | AESNF-H | 211 |
| 53 | 160 | AESNF | 164 |
| 54 | 160 | AETNF | 164 |
| 55 | 159 | AEANF-NAATKTATEAVKATTAAKR | 182 |
| 56 | 159 | AEANF-TAVTNTASEAVQSAQTRKR | 182 |
| 57 | 159 | AEANF-NAATKTATEAV-KATTTAK | 181 |
| 58 | 158 | AEANF-NAVSATAVNAAKPA | 176 |
| 59 | 158 | AEANF-NTVAASAVNASKTVS | 177 |
| 60 | 159 | AEANF | 163 |
| 61 | 158 | AETNF-NTVSESAVNASKSVS | 177 |
| 62 | 159 | AEANF | 163 |
| 63 | 159 | AE | 160 |
| 64 | 159 | AEANF | 163 |
| 65 | 159 | AQTNI-NTATDA | 169 |
| 66 | 158 | VEANM-NAVTSTAMKAAQTTSRTA | 180 |
| 67 | 158 | VEANM-NAVTSTAMKAAQ---TTSRT-TAKR | 183 |
| 68 | 159 | AEANF | 163 |
| 69 | 159 | AEANF | 163 |
| 70 | 159 | AEANF-NA | 165 |
| 71 | 159 | AEANF | 163 |

Figure 1H

| SEQ ID NO: | START | ALIGNMENT | END |
|---|---|---|---|
| 72 | 158 | AEANF-QA | 164 |
| 73 | 159 | AEANF-EA | 165 |
| 74 | 160 | AKANF | 164 |
| 75 | | | |
| 76 | | | |
| 77 | 163 | LEGNL-NAAANQFVSAAEKTTTRSR | 186 |
| 78 | 159 | AESNL | 163 |
| 79 | 163 | IEANV-GAAVNQFTQAAQNA | 181 |
| 80 | 159 | AQSNF-TAAATQASDAVKKVTKSA | 181 |
| 81 | 159 | AESNF-NSVAATASKTARRA | 177 |
| 82 | 163 | LEGNL-NAAASQFASAAEKTTARARKA | 188 |
| 83 | 159 | AESNF-----TAVTK---QAVSAATTSSKKR | 181 |
| 84 | 160 | AGARF | 164 |
| 85 | 159 | VESNI-TALSSAATKA | 173 |
| 86 | | | |
| 87 | 159 | AESNL | 163 |
| 88 | 161 | AESSF-NTAAQVASKGMQR | 178 |
| 89 | | | |
| 90 | 159 | AESNL | 163 |
| 91 | 163 | LEANL-ANATKQFTAAAEKTVASTR | 186 |
| 92 | 159 | AESNL | 163 |
| 93 | 159 | AE | 160 |
| 94 | | | |
| 95 | 159 | AE | 160 |
| 96 | 161 | AE | 162 |
| 97 | 160 | AENSF-NTAAAAASKGARH | 177 |
| 98 | 163 | LEANV-TNAVEQMSQAGAKVTRGAR | 186 |
| 99 | 159 | AE | 160 |
| 100 | 159 | AEANFKQLSATA | 170 |
| 101 | 160 | AQ | 161 |
| 102 | 159 | AE | 160 |
| 103 | 160 | AQAG--QSSASASTR | 172 |
| 104 | 160 | ARSNL | 164 |
| 105 | 159 | AQSNM | 163 |
| 106 | 160 | AQ | 161 |
| 107 | 161 | AEANM-AAATEATVKA | 175 |
| 108 | 158 | AEGSF-STAVEAASKGVRRREAQTTHGAAK | 186 |
| 109 | 160 | AETQ | 163 |
| 110 | 162 | AENG | 165 |
| 111 | 158 | AEANY-AAVTGSVIKAAK | 174 |
| 112 | | | |
| 113 | 157 | MDNAL-QAGAKTGKKAS | 172 |
| 114 | 157 | MDNAL-Q | 162 |
| 115 | 160 | AQSGF-DAVSDTAARGAKQ | 177 |
| 116 | 160 | TENNV-NLAASLASSSALQPSSNA | 182 |
| 117 | 157 | MDNAL-QAGAKIAKK | 170 |
| 118 | 160 | AEANI-QTATKA | 170 |
| 119 | 157 | MDNAL-QTGAKAGKKAS | 172 |
| 120 | | | |
| 121 | 162 | TE | 163 |

Figure 6

ATGATCCTCACCCCGGAACAAGTTGCAGCAGGCCAAAAGGCCAACCTCGAAACGCTGTTCGGCCTGACCAC
CAAGGCGTTTGAAGGCGTCGAAAAGCTCGTCGAGCTGAACCTTCAGGTCGTCAAGACTTCGTTCGCAGAAG
GCGTTGACAACGCCAAGAAGGCGCTGTGTCGGCCAAGGAACTGCTGGCCATCCAGGCCGCAGC
CGTGCAGCCGGTTGCCGAAAAGACCCTGGCCTACACCCGCCACCTGTATGAAATCGCTTCGGAAACCCAGA
GCGAGTTCACCAAGGTAGCCGAGGCTCAACTGGCTCGAAGAACGTGCAAGCGCTGGTCGAGAA
CCTCGCCAAGAACGCCCCGGCCGGTTCGGAATCGACCTGGCCATCGTGACCGGCGATCTCCGCTGCC
AACAACGCCTACGAGTCGGTGCAGAAGGCGACCAAGCAAGCGGTCGAAATCGCTGAAACCAACTTCCAGGC
TGCGGCTACGCGGCTGCCACCAAGGCTGCCCAGCAAGCCCCACGGGCCCGTACGGCCACGGGCAAAGAA
GACGACGGGCTGCCTGA

Figure 12
A
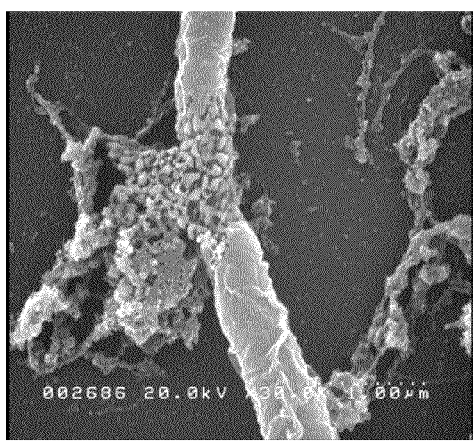
B
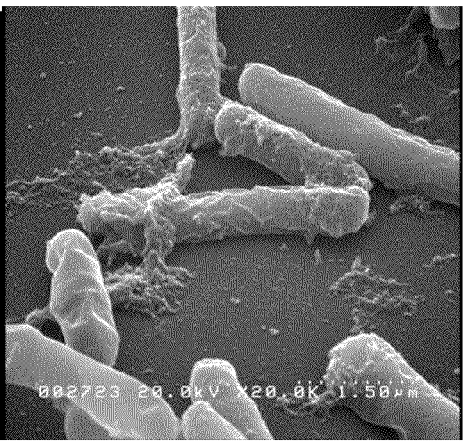
C
D

SEQUENCE LISTING

```
<160> NUMBER OF SEQ ID NOS: 121

<210> SEQ ID NO 1
<211> LENGTH: 192
<212> TYPE: PRT
<213> ORGANISM: Artificial Sequence
<220> FEATURE:
<223> OTHER INFORMATION: Sequence derived from Cupriavidus necator

<400> SEQUENCE: 1

Met Ile Leu Thr Pro Glu Gln Val Ala Ala Gln Lys Ala Asn Leu
1               5                   10                  15

Glu Thr Leu Phe Gly Leu Thr Thr Lys Ala Phe Glu Gly Val Glu Lys
                20                  25                  30

Leu Val Glu Leu Asn Leu Gln Val Val Lys Thr Ser Phe Ala Glu Gly
            35                  40                  45

Val Asp Asn Ala Lys Lys Ala Leu Ser Ala Lys Asp Ala Gln Glu Leu
        50                  55                  60

Leu Ala Ile Gln Ala Ala Ala Val Gln Pro Val Ala Glu Lys Thr Leu
```

```
            65                  70                  75                  80
Ala Tyr Thr Arg His Leu Tyr Glu Ile Ala Ser Glu Thr Gln Ser Glu
                    85                  90                  95

Phe Thr Lys Val Ala Glu Ala Gln Leu Ala Glu Gly Ser Lys Asn Val
                100                 105                 110

Gln Ala Leu Val Glu Asn Leu Ala Lys Asn Ala Pro Ala Gly Ser Glu
                115                 120                 125

Ser Thr Val Ala Ile Val Lys Ser Ala Ile Ser Ala Ala Asn Asn Ala
            130                 135                 140

Tyr Glu Ser Val Gln Lys Ala Thr Lys Gln Ala Val Glu Ile Ala Glu
145                 150                 155                 160

Thr Asn Phe Gln Ala Ala Ala Thr Ala Ala Thr Lys Ala Ala Gln Gln
                    165                 170                 175

Ala Ser Ala Thr Ala Arg Thr Ala Thr Ala Lys Lys Thr Thr Ala Ala
                180                 185                 190

<210> SEQ ID NO 2
<211> LENGTH: 228
<212> TYPE: PRT
<213> ORGANISM: Artificial Sequence
<220> FEATURE:
<223> OTHER INFORMATION: Sequence derived from Alcaligenes eutrophus

<400> SEQUENCE: 2

Met Ile Leu Thr Pro Glu Gln Val Ala Ala Gln Lys Ala Asn Leu
1               5                   10                  15

Glu Thr Leu Phe Gly Leu Thr Thr Lys Ala Phe Glu Gly Val Glu Lys
                20                  25                  30

Leu Val Glu Leu Asn Leu Gln Val Val Lys Thr Ser Phe Ala Glu Gly
            35                  40                  45

Val Asp Asn Ala Lys Lys Ala Leu Ser Ala Lys Asp Ala Gln Glu Leu
        50                  55                  60

Leu Ala Ile Gln Ala Ala Ala Val Gln Pro Val Ala Glu Lys Thr Leu
65                  70                  75                  80

Ala Tyr Thr Arg His Leu Tyr Glu Ile Ala Ser Glu Thr Gln Ser Glu
                    85                  90                  95

Phe Thr Lys Val Ala Glu Ala Gln Leu Ala Glu Gly Ser Lys Asn Val
                100                 105                 110

Gln Ala Leu Val Glu Asn Leu Ala Lys Asn Ala Pro Ala Gly Ser Glu
            115                 120                 125

Ser Thr Val Ala Ile Val Lys Ser Ala Ile Ser Ala Ala Asn Asn Ala
        130                 135                 140

Tyr Glu Ser Val Gln Lys Ala Thr Lys Gln Ala Val Glu Ile Ala Glu
145                 150                 155                 160

Thr Asn Phe Gln Ala Gly Gly Tyr Gly Cys His Gln Gly Cys Pro Ala
                    165                 170                 175

Ser Gln Arg His Gly Pro Tyr Gly His Gly Lys Glu Asp Asp Gly Cys
                180                 185                 190

Leu Ile Thr Ala Cys Val Glu Asp Gly Pro Ala Ala Gly Pro Leu
            195                 200                 205

Ala Lys Leu Ile Asp Ala Trp Arg Leu Arg Cys Val Leu Pro Thr Met
        210                 215                 220

Lys Val Val Pro
225
```

<210> SEQ ID NO 3
<211> LENGTH: 192
<212> TYPE: PRT
<213> ORGANISM: Artificial Sequence
<220> FEATURE:
<223> OTHER INFORMATION: Sequence derived from Cupriavidus taiwanensis

<400> SEQUENCE: 3

Met Ile Leu Thr Pro Glu Gln Val Ala Ala Gln Lys Ala Asn Leu
1               5                   10                  15

Glu Thr Leu Phe Gly Leu Thr Thr Lys Ala Phe Glu Gly Val Glu Lys
            20                  25                  30

Leu Val Glu Leu Asn Leu Gln Val Val Lys Thr Thr Phe Ala Glu Asn
        35                  40                  45

Val Asp Asn Ala Lys Lys Ala Leu Ser Ala Lys Asp Ala Gln Glu Leu
    50                  55                  60

Leu Ala Ile Gln Ala Ala Ala Val Gln Pro Val Ala Glu Lys Thr Leu
65                  70                  75                  80

Ala Tyr Thr Arg His Leu Tyr Glu Ile Ala Ser Glu Thr Gln Ser Glu
                85                  90                  95

Phe Ala Lys Val Ala Glu Ala Gln Leu Ala Glu Gly Ser Lys Asn Val
            100                 105                 110

Gln Ala Leu Val Glu Asn Phe Ala Lys Asn Ala Pro Ala Gly Ser Glu
        115                 120                 125

Ser Thr Val Ala Ile Val Lys Ser Ala Ile Ser Ala Ala Asn Asn Ala
    130                 135                 140

Tyr Glu Ser Val Gln Lys Ala Thr Lys Gln Ala Val Glu Ile Ala Glu
145                 150                 155                 160

Thr Asn Phe Gln Ala Ala Ala Ser Ala Ala Thr Lys Ala Ala Gln Gln
                165                 170                 175

Ala Ser Ala Thr Ala Arg Thr Ala Thr Ala Lys Lys Ala Ala Thr Ala
            180                 185                 190

<210> SEQ ID NO 4
<211> LENGTH: 192
<212> TYPE: PRT
<213> ORGANISM: Artificial Sequence
<220> FEATURE:
<223> OTHER INFORMATION: Sequence derived from Cupriavidus metallidurans
    CH34

<400> SEQUENCE: 4

Met Ile Leu Thr Pro Glu Gln Val Ala Ala Gln Lys Ala Asn Leu
1               5                   10                  15

Glu Thr Leu Phe Gly Leu Thr Ser Lys Ala Phe Glu Gly Val Glu Lys
            20                  25                  30

Leu Val Glu Leu Asn Leu Gln Val Val Lys Ala Thr Leu Ala Glu Asn
        35                  40                  45

Ala Asp Asn Ala Lys Lys Ala Leu Thr Ala Lys Asp Ala Gln Glu Leu
    50                  55                  60

Leu Ala Ile Gln Ala Ser Leu Val Gln Pro Val Ala Glu Lys Thr Leu
65                  70                  75                  80

Ala Tyr Thr Arg His Leu Tyr Glu Ile Ala Ser Glu Thr Gln Ser Glu
                85                  90                  95

Phe Thr Lys Val Ala Glu Ala Gln Leu Ala Glu Gly Thr Lys Asn Val
            100                 105                 110

Gln Ala Leu Val Asp Asn Leu Ala Lys Asn Ala Pro Ala Gly Ser Glu
        115                 120                 125

```
Ser Thr Val Ala Ile Val Lys Ser Ala Ile Ser Ala Ala Asn Asn Ala
        130                 135                 140

Tyr Glu Ser Val Gln Lys Ala Thr Lys Gln Ala Val Glu Met Ala Glu
145                 150                 155                 160

Ser Asn Phe Gln Ala Ala Ala Thr Ala Thr Lys Ala Ala Gln Gln
                165                 170                 175

Ala Ser Ala Thr Ala Arg Thr Ala Thr Lys Lys Ser Ala Ala Ala
            180                 185                 190

<210> SEQ ID NO 5
<211> LENGTH: 193
<212> TYPE: PRT
<213> ORGANISM: Artificial Sequence
<220> FEATURE:
<223> OTHER INFORMATION: Sequence derived from Ralstonia pickettii 12J

<400> SEQUENCE: 5

Met Leu Thr Gln Glu Gln Ile Ala Ala Ala His Lys Ala Asn Leu Glu
1               5                   10                  15

Thr Phe Phe Gly Leu Thr Asn Lys Ala Phe Glu Gly Val Glu Lys Leu
                20                  25                  30

Val Glu Leu Asn Leu Gln Val Val Lys Ala Thr Leu Ala Glu Asn Val
            35                  40                  45

Glu His Ala Lys Lys Ala Leu Thr Ala Lys Asp Ala Gln Glu Leu Leu
        50                  55                  60

Ser Val Gln Thr Ala Ala Val Gln Pro Leu Ala Glu Lys Val Leu Ala
65                  70                  75                  80

Tyr Ser Arg His Leu Tyr Glu Ile Ala Ser Asp Thr Gln Thr Glu Phe
                85                  90                  95

Ser Lys Ala Ala Glu Ala Gln Ile Ala Glu Asn Ser Arg Lys Leu Gln
                100                 105                 110

Ala Leu Val Asp Asn Val Ser Lys Asn Ala Pro Ala Gly Ser Glu Ser
            115                 120                 125

Ala Val Ala Leu Val Lys Ser Ala Leu Ser Ala Ala Asn Asn Ala Tyr
        130                 135                 140

Asp Ser Val Gln Lys Ala Thr Lys Gln Ala Val Glu Leu Ala Glu Ser
145                 150                 155                 160

Asn Phe His Ala Ala Ala Asn Ala Ala Ser Lys Ala Thr Ala Gln Ala
                165                 170                 175

Ser Ala Gln Ala Arg Ala Ala Thr Gly Lys Lys Ser Ala Thr Thr Ala
            180                 185                 190

Ala

<210> SEQ ID NO 6
<211> LENGTH: 193
<212> TYPE: PRT
<213> ORGANISM: Artificial Sequence
<220> FEATURE:
<223> OTHER INFORMATION: Sequence derived from Ralstonia solanacearum
      GMI1000

<400> SEQUENCE: 6

Met Leu Thr Gln Glu Gln Ile Ala Ala Ala Gln Lys Ala As

```
                35                  40                  45
Glu His Ser Lys Lys Ala Leu Ser Ala Lys Asp Ala Gln Glu Leu Leu
             50                  55                  60

Ala Val His Thr Ala Ala Val Gln Pro Leu Ala Glu Lys Val Leu Ala
 65                  70                  75                  80

Tyr Asn Arg His Leu Tyr Glu Ile Phe Ser Asp Thr Gln Thr Glu Phe
                 85                  90                  95

Gly Lys Val Ala Glu Thr Gln Ile Ala Glu Gly Ser Arg Lys Leu Gln
            100                 105                 110

Ala Leu Ile Asp Asn Val Ser Lys Asn Ala Pro Ala Gly Ser Glu Ser
            115                 120                 125

Ala Val Ala Leu Val Lys Ser Ala Leu Ser Ala Ala Asn Asn Ala Tyr
            130                 135                 140

Asp Ser Val Gln Lys Ala Thr Lys Gln Ala Val Glu Leu Ala Glu Ser
145                 150                 155                 160

Asn Phe His Ala Ala Ala Asn Ala Ala Ser Lys Ala Thr Ala Gln Ala
                165                 170                 175

Ala Ala Gln Ala Arg Ala Ala Thr Asn Lys Lys Ser Thr Asn Ala Ala
            180                 185                 190

Ala

<210> SEQ ID NO 7
<211> LENGTH: 193
<212> TYPE: PRT
<213> ORGANISM: Artificial Sequence
<220> FEATURE:
<223> OTHER INFORMATION: Sequence derived from Ralstonia pickettii 12D

<400> SEQUENCE: 7

Met Leu Thr Gln Glu Gln Ile Ala Ala Ala His Lys Ala Asn Leu Glu
  1               5                  10                  15

Thr Phe Phe Gly Leu Thr Asn Lys Ala Phe Glu Gly Val Glu Lys Leu
                 20                  25                  30

Val Glu Leu Asn Leu Gln Val Val Lys Ala Thr Leu Ala Glu Asn Val
             35                  40                  45

Glu His Ala Lys Lys Ala Leu Thr Ala Lys Asp Ala Gln Glu Leu Leu
 50                  55                  60

Ser Val Gln Thr Ala Ala Val Gln Pro Leu Ala Glu Lys Val Leu Ala
 65                  70                  75                  80

Tyr Ser Arg His Leu Tyr Glu Ile Ala Ser Asp Thr Gln Thr Glu Phe
                 85                  90                  95

Ser Lys Ala Ala Glu Val Gln Ile Ala Glu Asn Ser Arg Lys Leu Gln
            100                 105                 110

Ala Leu Val Asp Asn Val Ser Lys Asn Ala Pro Ala Gly Ser Glu Ser
            115                 120                 125

Ala Val Ala Leu Val Lys Ser Ala Leu Ser Ala Ala Asn Asn Ala Tyr
            130                 135                 140

Asp Ser Val Gln Lys Ala Thr Lys Gln Ala Val Glu Leu Ala Glu Ser
145                 150                 155                 160

Asn Phe His Ala Ala Ala Asn Ala Ala Ser Lys Ala Thr Ala Gln Ala
                165                 170                 175

Ser Ala Gln Ala Arg Ala Ala Thr Gly Lys Lys Ser Thr Thr Thr Ala
            180                 185                 190

Ala
```

<210> SEQ ID NO 8
<211> LENGTH: 60
<212> TYPE: PRT
<213> ORGANISM: Artificial Sequence
<220> FEATURE:
<223> OTHER INFORMATION: Sequence derived from Escherichia coli

<400> SEQUENCE: 8

Leu Ala Tyr Gly Ser Gln Gly Asp Leu Asn Pro Leu Ile Asn Glu Ile
1               5                   10                  15

Ser Lys Ile Ile Ser Ala Ala Gly Ser Phe Asp Val Lys Glu Glu Arg
            20                  25                  30

Thr Ala Ala Ser Leu Leu Gln Leu Ser Gly Asn Ala Ser Asp Phe Ser
        35                  40                  45

Tyr Gly Arg Asn Ser Ile Thr Leu Thr Thr Ser Ala
    50                  55                  60

<210> SEQ ID NO 9
<211> LENGTH: 42
<212> TYPE: PRT
<213> ORGANISM: Artificial Sequence
<220> FEATURE:
<223> OTHER INFORMATION: Sequence derived from Escherichia coli

<400> SEQUENCE: 9

Met Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gln Ala
        35                  40

<210> SEQ ID NO 10
<211> LENGTH: 18
<212> TYPE: PRT
<213> ORGANISM: Artificial Sequence
<220> FEATURE:
<223> OTHER INFORMATION: Sequence derived from Escherichia coli

<400> SEQUENCE: 10

Met Lys Lys Leu Leu Phe Ala Ile Pro Leu Val Val Pro Phe Tyr Ser
1               5                   10                  15

His Ser

<210> SEQ ID NO 11
<211> LENGTH: 22
<212> TYPE: PRT
<213> ORGANISM: Artificial Sequence
<220> FEATURE:
<223> OTHER INFORMATION: Sequence derived from Escherichia coli

<400> SEQUENCE: 11

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 12
<211> LENGTH: 21
<212> TYPE: PRT
<213> ORGANISM: Artificial Sequence
<220> FEATURE:
<223> OTHER INFORMATION: Sequence derived from Escherichia coli -continued

<400> SEQUENCE: 12

Met Lys Lys Thr Ala Ile Ala Ile Ala Val Ala Leu Ala Gly Phe Ala
1               5                   10                  15

Thr Val Ala Gln Ala
            20

<210> SEQ ID NO 13
<211> LENGTH: 22
<212> TYPE: PRT
<213> ORGANISM: Artificial Sequence
<220> FEATURE:
<223> OTHER INFORMATION: Sequence derived from Escherichis coli

<400> SEQUENCE: 13

Met Met Lys Arg Asn Ile Leu Ala Val Ile Val Pro Ala Leu Leu Val
1               5                   10                  15

Ala Gly Thr Ala Asn Ala
            20

<210> SEQ ID NO 14
<211> LENGTH: 21
<212> TYPE: PRT
<213> ORGANISM: Artificial Sequence
<220> FEATURE:
<223> OTHER INFORMATION: Sequence derived from Escherichia coli

<400> SEQUENCE: 14

Met Lys Val Lys Val Leu Ser Leu Leu Val Pro Ala Leu Leu Val Ala
1               5                   10                  15

Gly Ala Ala Asn Ala
            20

<210> SEQ ID NO 15
<211> LENGTH: 20
<212> TYPE: PRT
<213> ORGANISM: Artificial Sequence
<220> FEATURE:
<223> OTHER INFORMATION: Sequence derived from Escherichia coli

<400> SEQUENCE: 15

Met Arg Ala Lys Leu Leu Gly Ile Val Leu Thr Thr Pro Ile Ala Ile
1               5                   10                  15

Ser Ser Phe Ala
            20

<210> SEQ ID NO 16
<211> LENGTH: 23
<212> TYPE: PRT
<213> ORGANISM: Artificial Sequence
<220> FEATURE:
<223> OTHER INFORMATION: Sequence derived from Escherichia coli

<400> SEQUENCE: 16

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 17
<211> LENGTH: 21
<212> TYPE: PRT
<213> ORGANISM: Artificial Sequence
<220> FEATURE:

<223> OTHER INFORMATION: Sequence derived from Escherichia coli

<400> SEQUENCE: 17

Met Lys Gln Ser Thr Ile Ala Leu Ala Leu Leu Pro Leu Leu Phe Thr
1               5                   10                  15

Pro Val Thr Lys Ala
            20

<210> SEQ ID NO 18
<211> LENGTH: 21
<212> TYPE: PRT
<213> ORGANISM: Artificial Sequence
<220> FEATURE:
<223> OTHER INFORMATION: Sequence derived from Escherichia coli

<400> SEQUENCE: 18

Met Lys Lys Ser Thr Leu Ala Leu Val Val Met Gly Ile Val Ala Ser
1               5                   10                  15

Ala Ser Val Gln Ala
            20

<210> SEQ ID NO 19
<211> LENGTH: 26
<212> TYPE: PRT
<213> ORGANISM: Artificial Sequence
<220> FEATURE:
<223> OTHER INFORMATION: Sequence derived from Escherichia coli

<400> SEQUENCE: 19

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 20
<211> LENGTH: 28
<212> TYPE: PRT
<213> ORGANISM: Artificial Sequence
<220> FEATURE:
<223> OTHER INFORMATION: Sequence derived from Escherichia coli

<400> SEQUENCE: 20

Met Phe Lys Phe Lys Lys Lys Phe Leu Val Gly Leu Thr Ala Ala Phe
1               5                   10                  15

Met Ser Ile Ser Met Phe Ser Ala Thr Ala Ser Ala
            20                  25

<210> SEQ ID NO 21
<211> LENGTH: 20
<212> TYPE: PRT
<213> ORGANISM: Artificial Sequence
<220> FEATURE:
<223> OTHER INFORMATION: Sequence derived from Escherichis coli

<400> SEQUENCE: 21

Met Lys Ala Thr Lys Leu Val Leu Gly Ala Val Ile Leu Gly Ser Thr
1               5                   10                  15

Leu Leu Ala Gly
            20

<210> SEQ ID NO 22
<211> LENGTH: 25
<212> TYPE: PRT
<213> ORGANISM: Artificial Sequence -continued

```
<220> FEATURE:
<223> OTHER INFORMATION: Sequence derived from Escherichia coli

<400> SEQUENCE: 22

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 23
<211> LENGTH: 21
<212> TYPE: PRT
<213> ORGANISM: Artificial Sequence
<220> FEATURE:
<223> OTHER INFORMATION: Sequence derived from Escherichia coli

<400> SEQUENCE: 23

Met Asn Lys Val Lys Cys Tyr Val Leu Phe Thr Ala Leu Leu Ser Ser
1               5                   10                  15

Leu Tyr Ala His Gly
            20

<210> SEQ ID NO 24
<211> LENGTH: 10
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (7)..(10)
<223> OTHER INFORMATION: n can be any nucleotide

<400> SEQUENCE: 24 aggaggnnnn                                                                10

<210> SEQ ID NO 25
<211> LENGTH: 589
<212> TYPE: PRT
<213> ORGANISM: Artificial Sequence
<220> FEATURE:
<223> OTHER INFORMATION: Sequence derived from Ralstonia eutropha

<400> SEQUENCE: 25

Met Ala Thr Gly Lys Gly Ala Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140
```

```
Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
            260                 265                 270

Phe Leu Val Ser Trp Arg Asn Pro Asp Ala Ser Met Ala Gly Ser Thr
        275                 280                 285

Trp Asp Asp Tyr Ile Glu His Ala Ala Ile Arg Ala Ile Glu Val Ala
290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
        355                 360                 365

Leu Arg Glu Ala Thr Leu Gly Gly Ala Gly Ala Pro Cys Ala Leu
370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
        435                 440                 445

Glu Leu Lys Val Pro Gly Lys Leu Thr Val Cys Gly Val Pro Val Asp
450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
530                 535                 540

Gly Ser Trp Trp Pro Asp Trp Thr Ala Trp Leu Ala Gly Gln Ala Gly
545                 550                 555                 560
```

```
Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
            580                 585

<210> SEQ ID NO 26
<211> LENGTH: 393
<212> TYPE: PRT
<213> ORGANISM: Artificial Sequence
<220> FEATURE:
<223> OTHER INFORMATION: Sequence derived from Ralstonia eutropha

<400> SEQUENCE: 26

Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
        195                 200                 205

Gly Asp Pro Val Ala Phe Lys Thr Asp Glu Phe Val Arg Gln Gly Ala
210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335
```

```
Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390

<210> SEQ ID NO 27
<211> LENGTH: 246
<212> TYPE: PRT
<213> ORGANISM: Artificial Sequence
<220> FEATURE:
<223> OTHER INFORMATION: Sequence derived from Ralstonia eutropha

<400> SEQUENCE: 27

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 28
<211> LENGTH: 579
<212> TYPE: DNA
<213> ORGANISM: Artificial Sequence
<220> FEATURE:
<223> OTHER INFORMATION: Sequence derived from synthetic sequence

<400> SEQUENCE: 28
```

```
atgatcctca ccccggaaca agttgcagca gcgcaaaagg ccaacctcga aacgctgttc    60
ggcctgacca ccaaggcgtt tgaaggcgtc gaaaagctcg tcgagctgaa ccttcaggtc   120
gtcaagactt cgttcgcaga aggcgttgac aacgccaaga aggcgctgtc ggccaaggac   180
gcacaggaac tgctggccat ccaggccgca gccgtgcagc cggttgccga aaagaccctg   240
gcctacaccc gccacctgta tgaaatcgct tcggaaaccc agagcgagtt caccaaggta   300
gccgaggctc aactggccga aggctcgaag aacgtgcaag cgctggtcga aacctcgcc    360 aagaacgccc cggccggttc ggaatcgacc gtggccatcg tgaagtcggc gatctccgct   420
gccaacaacg cctacgagtc ggtgcagaag gcgaccaagc aagcggtcga aatcgctgaa   480
accaacttcc aggctgcggc tacggctgcc accaaggctg cccagcaagc cagcgccacg   540
gcccgtacgg ccacggcaaa gaagacgacg gctgcctga                         579
```

<210> SEQ ID NO 29
<211> LENGTH: 193
<212> TYPE: PRT
<213> ORGANISM: Artificial Sequence
<220> FEATURE:
<223> OTHER INFORMATION: Sequence derived from Ralstonia solanacearum PSI07

<400> S

```
<400> SEQUENCE: 30

Met Leu Thr Gln Glu Gln Ile Ala Ala Ala Gln Lys Ala Asn Leu Glu
1               5                   10                  15

Thr Phe Phe Gly Leu Thr Asn Lys Ala Phe Glu Gly Val Glu Lys Leu
            20                  25                  30

Val Glu Leu Asn Leu Gln Val Val Lys Ala Thr Leu Ala Glu Asn Val
        35                  40                  45

Glu His Ser Lys Lys Ala Leu Ser Ala Lys Asp Ala Gln Glu Leu Leu
    50                  55                  60

Ala Val His Thr Ala Ala Val Gln Pro Leu Ala Glu Lys Val Leu Ala
65                  70                  75                  80

Tyr Asn Arg His Leu Tyr Glu Ile Phe Ser Asp Thr Gln Thr Glu Phe
                85                  90                  95

Gly Lys Val Ala Glu Thr Gln Ile Ala Glu Asn Gly Arg Lys Leu Gln
            100                 105                 110

Ala Leu Ile Asp Asn Val Ser Lys Asn Ala Pro Ala Gly Ser Glu Ser
        115                 120                 125

Ala Val Ala Leu Val Lys Ser Ala Leu Ser Ala Ala Asn Asn Ala Tyr
    130                 135                 140

Asp Ser Val Gln Lys Ala Thr Lys Gln Ala Val Glu Leu Ala Glu Ser
145                 150                 155                 160

Asn Phe His Ala Ala Ala Asn Ala Ala Ser Lys Ala Thr Ala Gln Ala
                165                 170                 175

Ala Ala Gln Ala Arg Ala Ala Thr Thr Ser Lys Lys Ser Thr Thr Thr
            180                 185                 190

Ala Ala

<210> SEQ ID NO 31
<211> LENGTH: 188
<212> TYPE: PRT
<213> ORGANISM: Artificial Sequence
<220> FEATURE:
<223> OTHER INFORMATION: Sequence derived from Burkholderia cenocepacia
      J2315

<400> SEQUENCE: 31

```
                 145                 150                 155                 160
Glu Thr Asn Phe Asn Ala Ala Ala Val Ala Thr Lys Ala Ala Thr
                165                 170                 175

Ala Ala Ala Ala Arg Arg Ser Ser Lys Pro Ala Ala
            180                 185

<210> SEQ ID NO 32
<211> LENGTH: 188
<212> TYPE: PRT
<213> ORGANISM: Artificial Sequence
<220> FEATURE:
<223> OTHER INFORMATION: Sequence derived from Burkholderia sp. 383

<400> SEQUENCE: 32

Met Ser Leu Leu Thr Pro Glu Gln Ile Ala Ala Gln Lys Ala Asn
1               5                   10                  15

Leu Glu Ser Leu Phe Gly Leu Thr Thr Lys Ala Phe Glu Gly Val Glu
                20                  25                  30

Lys Leu Ile Glu Leu Asn Leu Gln Val Val Lys Ser Thr Leu Ala Glu
            35                  40                  45

Gly Gln Glu Asn Ala Gln Arg Leu Leu Ser Val Lys Asp Ala Gln Glu
50                  55                  60

Leu Ile Ala Leu Gln Ala Ser Leu Ser Gln Pro Val Ala Glu Lys Val
65                  70                  75                  80

Leu Ser Tyr Gly Arg His Leu Tyr Glu Ile Ala Ser Ser Thr Gln Ala
                85                  90                  95

Glu Phe Ala Lys Val Ala Glu Ala Gln Phe Glu Glu Gln Asn Lys Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Asn Thr
130                 135                 140

Thr Tyr Glu Thr Val Gln Lys Ala Thr Lys Gln Ala Val Glu Ile Ala
145                 150                 155                 160

Glu Thr Asn Phe Asn Ala Ala Ala Val Ala Thr Lys Ala Ala Thr
                165                 170                 175

Ala Ala Ala Ala Arg Arg Thr Ser Lys Pro Thr Ala
            180                 185

<210> SEQ ID NO 33
<211> LENGTH: 188
<212> TYPE: PRT
<213> ORGANISM: Artificial Sequence
<220> FEATURE:
<223> OTHER INFORMATION: Sequence derived from Burkholderia multivorans
      CGD2M

<400> SEQUENCE: 33

Met Ser Leu Leu Thr Pro Glu Gln Ile Ala Ala Gln Lys Ala Asn
1               5                   10                  15

Leu Glu Ser Leu Phe Gly Leu Thr Thr Lys Ala Phe Glu Gly Val Glu
                20                  25                  30

Lys Leu Ile Glu Leu Asn Leu Gln Val Val Lys Ser Thr Leu Ala Glu
            35                  40                  45

Gly Gln Glu Asn Ala Gln Arg Leu Leu Ser Val Lys Asp Ala Gln Glu
50                  55                  60

Leu Ile Ala Leu Gln Ala Ser Leu Thr Gln Pro Val Ala Glu Lys Val
65                  70                  75                  80
```

```
Leu Ser Tyr Gly Arg His Leu Tyr Glu Ile Ala Ser Ala Thr Gln Ala
                85                  90                  95

Glu Phe Ala Lys Val Ala Glu Ala Gln Phe Glu Gln Asn Arg Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Asn Thr
    130                 135                 140

Thr Tyr Glu Thr Val Gln Lys Ala Thr Lys Gln Ala Val Glu Ile Ala
145                 150                 155                 160

Glu Thr Asn Phe Asn Ala Ala Ala Val Ala Ser Lys Ala Ala Thr
                165                 170                 175

Ala Ala Ala Ser Arg Arg Thr Ser Lys Pro Ala Ala
            180                 185

<210> SEQ ID NO 34
<211> LENGTH: 194
<212> TYPE: PRT
<213> ORGANISM: Artificial Sequence
<220> FEATURE:
<223> OTHER INFORMATION: Sequence derived from Burkholderia phymatum
      STM815

<400> SEQUENCE: 34

Met Thr Leu Leu Thr Pro Glu Gln Phe Ala Ala Gln Lys Ala Asn
1               5                   10                  15

Leu Glu Thr Leu Phe Gly Leu Thr Ser Lys Ala Phe Glu Gly Val Glu
            20                  25                  30

Lys Leu Val Glu Leu Asn Leu Gln Val Val Lys Ser Thr Ile Ala Glu
        35                  40                  45

Ser Gln Glu Asn Ala Gln Arg Ala Leu Ser Val Lys Asp Ala Gln Glu
    50                  55                  60

Leu Leu Ala Leu Gln Ala Gly Leu Thr Gln Pro Val Ala Glu Lys Val
65                  70                  75                  80

Leu Ser Tyr Gly Arg His Leu Tyr Glu Ile Ala Ser Ala Thr Gln Ala
                85                  90                  95

Glu Phe Ala Arg Val Ala Glu Ala Gln Tyr Glu Gln Asn Lys Lys
            100                 105                 110

Val Gln Ala Leu Val Glu Asn Val Ala Lys Asn Ala Pro Ala Gly Ser
        115                 120                 125

Glu Thr Ala Val Ala Val Ile Lys Ser Ala Ile Thr Ala Ala Asn Thr
    130                 135                 140

Thr Tyr Glu Thr Val His Lys Ala Thr Lys Gln Ala Val Glu Ile Ala
145                 150                 155                 160

Glu Ser Asn Phe Asn Ala Ala Thr Ala Ala Ser Lys Ala Ala Ser
                165                 170                 175

Gln Ala Ala Ala Gln Ala Ser Arg Thr Ala Ala Ser Ala Lys Lys Ala
            180                 185                 190

Ala Val

<210> SEQ ID NO 35
<211> LENGTH: 188
<212> TYPE: PRT
<213> ORGANISM: Artificial Sequence
<220> FEATURE:
<223> OTHER INFORMATION: Sequence derived from Burkholderia dolosa
      AUO158
```

<400> SEQUENCE: 35

```
Met Ser Leu Leu Thr Pro Glu Gln Ile Ala Ala Gln Lys Ala Asn
1               5                   10                  15

Leu Glu Ser Leu Phe Gly Leu Thr Thr Lys Ala Phe Glu Gly Val Glu
            20                  25                  30

Lys Leu Ile Glu Leu Asn Leu Gln Val Val Lys Ser Thr Leu Val Glu
        35                  40                  45

Ser Gln Glu Asn Ala Gln Arg Leu Leu Ser Ala Lys Asp Ala Gln Glu
    50                  55                  60

Leu Leu Ala Leu Gln Ala Ser Leu Thr Gln Pro Val Ala Glu Lys Val
65                  70                  75                  80

Leu Ser Tyr Gly Arg His Leu Tyr Glu Ile Ala Ser Ser Thr Gln Ala
                85                  90                  95

Glu Phe Ala Lys Val Ala Glu Ala Gln Phe Glu Glu Gln Asn Arg Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Asn Thr
    130                 135                 140

Thr Tyr Glu Thr Val Gln Lys Ala Thr Lys Gln Ala Val Glu Ile Ala
145                 150                 155                 160

Glu Thr Asn Phe Asn Ala Ala Ala Val Ala Thr Lys Ala Ala Thr
                165                 170                 175

Ala Ala Ala Ser Arg Arg Ser Ser Lys Pro Ala Ala
            180                 185
```

<210> SEQ ID NO 36
<211> LENGTH: 188
<212> TYPE: PRT
<213> ORGANISM: Artificial Sequence
<220> FEATURE:
<223> OTHER INFORMATION: Sequence derived from Burkholderia multivorans
      ATCC 17616

<400> SEQUENCE: 36

```
Met Ser Leu Leu Thr Pro Glu Gln Ile Ala Ala Gln Lys Ala Asn
1               5                   10                  15

Leu Glu Ser Leu Phe Gly Leu Thr Thr Lys Ala Phe Glu Gly Val Glu
            20                  25                  30

Lys Leu Ile Glu Leu Asn Leu Gln Val Val Lys Ser Thr Leu Ala Glu
        35                  40                  45

Gly Gln Glu Asn Ala Gln Arg Leu Leu Ser Val Lys Asp Ala Gln Glu
    50                  55                  60

Leu Ile Ala Leu Gln Ala Ser Leu Thr Gln Pro Val Ala Glu Lys Val
65                  70                  75                  80

Leu Ser Tyr Gly Arg His Leu Tyr Glu Ile Ala Ser Ala Thr Gln Ala
                85                  90                  95

Glu Phe Ala Lys Val Ala Glu Ala Gln Phe Glu Glu Gln Asn Lys Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Asn Thr
    130                 135                 140

Thr Tyr Glu Thr Val Gln Lys Ala Ala Lys Gln Ala Val Glu Ile Ala
145                 150                 155                 160
```

Glu Thr Asn Phe Asn Ala Ala Ala Val Ala Ser Lys Ala Thr
                165                 170                 175

Ala Ala Ala Ser Arg Arg Thr Ser Lys Pro Ala Ala
            180                 185

<210> SEQ ID NO 37
<211> LENGTH: 191
<212> TYPE: PRT
<213> ORGANISM: Artificial Sequence
<220> FEATURE:
<223> OTHER INFORMATION: Sequence derived from Burkholderia sp. CCGE1002

<400> SEQUENCE: 37

Met Thr Leu Leu Thr Pro Glu Gln Phe Ala Ala Gln Lys Ala Asn
1               5                   10                  15

Phe Glu Thr Leu Phe Gly Leu Thr Lys Ala Phe Glu Gly Val Glu
                20                  25                  30

Lys Leu Val Glu Leu Asn Leu Gln Val Val Lys Ser Thr Leu Ala Glu
                35                  40                  45

Ser Gln Glu Asn Ala Gln Arg Ala Leu Ser Val Lys Asp Ala Gln Glu
        50                  55                  60

Leu Leu Ala Leu Gln Ala Ser Leu Ala Gln Pro Val Ala Glu Lys Ala
65                  70                  75                  80

Leu Ser Tyr Gly Arg His Val Tyr Glu Ile Val Ser Ala Thr Gln Gly
                85                  90                  95

Glu Phe Thr Arg Val Ala Glu Ala Gln Phe Glu Glu Gln Asn Arg Lys
                100                 105                 110

Val Gln Ala Leu Val Glu Asn Val Ala Lys Asn Ala Pro Ala Gly Ser
            115                 120                 125

Glu Thr Ala Val Ala Val Met Lys Ser Ala Ile Thr Ala Ala Asn Thr
            130                 135                 140

Thr Tyr Glu Thr Val His Lys Ala Thr Arg Gln Ala Val Glu Ile Ala
145                 150                 155                 160

Glu Ser Asn Phe Asn Ala Ala Thr Ala Ala Ser Lys Ala Ala Ser
                165                 170                 175

Gln Ala Ala Ala Gln Ala Ser Arg Ala Ala Ala Lys Lys Ala Val
            180                 185                 190

<210> SEQ ID NO 38
<211> LENGTH: 188
<212> TYPE: PRT
<213> ORGANISM: Artificial Sequence
<220> FEATURE:
<223> OTHER INFORMATION: Sequence derived from Burkholderia ambifaria
      AMMD

<400> SEQUENCE: 38

Met Ser Leu Leu Thr Pro Glu Gln Ile Ala Ala Gln Lys Ala Asn
1               5                   10                  15

Leu Glu Ser Leu Phe Gly Leu Thr Thr Lys Ala Phe Glu Gly Val Glu
                20                  25                  30

Lys Leu Ile Glu Leu Asn Leu Gln Val Val Lys Ser Thr Leu Thr Glu
                35                  40                  45

Ser Gln Glu Asn Ala Gln Arg Leu Leu Ser Val Lys Asp Ala Gln Glu
        50                  55                  60

Leu Ile Ala Leu Gln Ala Ser Leu Ser Gln Pro Val Ala Glu Lys Val
65                  70                  75                  80

-continued

```
Leu Ser Tyr Thr Arg His Leu Tyr Glu Ile Ala Ser Thr Gln Ala
                 85                  90                  95

Glu Phe Ala Lys Val Ala Glu Ala Gln Phe Glu Glu Gln Asn Lys Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Asn Thr
    130                 135                 140

Thr Tyr Glu Thr Val Gln Lys Ala Ala Lys Gln Ala Val Glu Ile Ala
145                 150                 155                 160

Glu Thr Asn Phe Asn Ala Ala Ala Val Ala Thr Lys Ala Ala Ser
                165                 170                 175

Ala Ala Ala Ser Arg Arg Ser Thr Lys Pro Ala Ala
            180                 185
```

<210> SEQ ID NO 39
<211> LENGTH: 188
<212> TYPE: PRT
<213> ORGANISM: Artificial Sequence
<220> FEATURE:
<223> OTHER INFORMATION: Sequence derived from Burkholderia cenocepacia AU 1054

<400> SEQUENCE: 39

```
Met Ser Leu Leu Thr Pro Glu Gln Ile Ala Ala Gln Lys Ala Asn
1               5                   10                  15

Leu Glu Ser Leu Phe G

Met Thr Leu Leu Thr Pro Glu Gln Phe Ala Ala Gln Lys Ala Asn
1               5                   10                  15

Phe Glu Thr Leu Phe Gly Leu Thr Thr Lys Ala Phe Glu Gly Val Glu
            20                  25                  30

Lys Leu Val Glu Leu Asn Leu Gln Val Val Lys Ser Thr Leu Ala Glu
        35                  40                  45

Ser Gln Glu Asn Ala Gln Arg Ala Leu Ser Val Lys Asp Ala Gln Glu
    50                  55                  60

Leu Leu Ala Leu Gln Ala Ser Leu Ala Gln Pro Val Ala Glu Lys Ala
65                  70                  75                  80

Leu Ser Tyr Gly Arg His Val Tyr Glu Ile Val Ser Ala Thr Gln Gly
                85                  90                  95

Glu Phe Thr Arg Val Ala Glu Ala Gln Phe Glu Glu Gln Asn Arg Lys
            100                 105                 110

Val Gln Ser Leu Val Glu Asn Val Ala Lys Asn Ala Pro Ala Gly Ser
        115                 120                 125

Glu Thr Ala Val Ala Val Leu Lys Ser Ala Ile Thr Ala Ala Asn Thr
    130                 135                 140

Thr Tyr Asp Thr Val His Lys Ala Thr Lys Gln Ala Val Glu Ile Ala
145                 150                 155                 160

Glu Ser Asn Phe Asn Ala Ala Ala Thr Ala Ala Ser Lys Ala Ala Ser
                165                 170                 175

Gln Ala Ala Ala Gln Ala Ser Arg Ser Ala Lys Lys Ala Val
            180                 185                 190

<210> SEQ ID NO 41
<211> LENGTH: 193
<212> TYPE: PRT
<213> ORGANISM: Artificial Sequence
<220> FEATURE:
<223> OTHER INFORMATION: Sequence derived from Burkholderia
      thailandensis TXDOH

<400> SEQUENCE: 41

Met Asn Met Ser Leu Leu Thr Pro Glu Gln Ile Ala Ala Gln Lys
1               5                   10                  15

Ala Asn Ile Glu Ser Leu Phe Gly Leu Thr Thr Lys Ala Phe Glu Gly
            20                  25                  30

Val Glu Lys Leu Ile Glu Leu Asn Leu Gln Val Val Lys Ser Thr Leu
        35                  40                  45

Ala Glu Ser Gln Glu Asn Val Gln Arg Ala Leu Ser Val Lys Asp Ala
    50                  55                  60

Gln Glu Leu Leu Ala Leu Gln Ala Ser Leu Thr Gln Pro Ile Ala Glu
65                  70                  75                  80

Lys Val Leu Ala Tyr Gly Arg His Val Tyr Glu Ile Ala Ser Ala Thr
                85                  90                  95

Gln Ala Glu Phe Ala Lys Val Ala Glu Ala Gln Tyr Glu Glu Gln Asn
            100                 105                 110

Arg Lys Val Gln Ala Leu Val Asp Asn Val Ala Lys Asn Ala Pro Ala
        115                 120                 125

Gly Ser Glu Thr Ala Val Ala Ala Leu Lys Ser Ala Ile Asn Ala Ala
    130                 135                 140

Asn Thr Thr Tyr Glu Thr Val Gln Lys Ala Lys Gln Ala Val Glu
145                 150                 155                 160

Ile Ala Glu Thr Asn Phe Asn Ala Ala Ala Ala Val Ala Thr Lys Ala
                165                 170                 175

```
Ala Asn Thr Ala Ala Ala Ala Ser Arg Arg Ser Gly Thr Gly Lys Thr
                180                 185                 190

Ala

<210> SEQ ID NO 42
<211> LENGTH: 190
<212> TYPE: PRT
<213> ORGANISM: Artificial Sequence
<220> FEATURE:
<223> OTHER INFORMATION: Sequence derived from Burkholderia graminis
      C4D1M

<400> SEQUENCE: 42

Met Thr Leu Leu Thr Pro Glu Gln Phe Ala Ala Ala Gln Lys Ala Asn
1               5                   10                  15

Phe Glu Thr Leu Phe Gly Leu Thr Thr Lys Ala Phe Glu Gly Val Glu
                20                  25                  30

Lys Leu Val Glu Leu Asn Leu Gln Val Val Lys Ser Thr Leu Ala Glu
            35                  40                  45

Ser Gln Glu Asn Ala Gln Arg Ala Leu Ser Val Lys Asp Ala Gln Glu
        50                  55                  60

Leu Leu Ala Leu Gln Ala Ser Leu Ala Gln Pro Val Ala Glu Lys Ala
65                  70                  75                  80

Leu Ser Tyr Gly Arg His Val Tyr Glu Ile Val Ser Ala Thr Gln Gly
                85                  90                  95

Glu Phe Ala Arg Val Ala Glu Ala Gln Phe Glu Glu Gln Asn Arg Lys
                100                 105                 110

Val Gln Ser Leu Val Glu Asn Val Ala Lys Asn Ala Pro Ala Gly Ser
            115                 120                 125

Glu Thr Ala Val Ala Val Ile Lys Ser Ala Ile Thr Ala Ala Asn Thr
        130                 135                 140

Thr Tyr Glu Thr Val His Lys Ala Thr Lys Gln Ala Val Glu Ile Ala
145                 150                 155                 160

Glu Ser Asn Phe Asn Ala Ala Thr Ala Ser Lys Ala Ala Ser
                165                 170                 175

Gln Ala Ala Ala Gln Ala Ser Arg Ser Ala Lys Lys Pro Val
            180                 185                 190

<210> SEQ ID NO 43
<211> LENGTH: 187
<212> TYPE: PRT
<213> ORGANISM: Artificial Sequence
<220> FEATURE:
<223> OTHER INFORMATION: Sequence derived from Burkholderia pseudomallei
      S13

<400> SEQUENCE: 43

Met Leu Thr Pro Glu Gln Ile Ala Ala Ala Gln Lys Ala Asn Ile Glu
1               5                   10                  15

Ser Leu Phe Gly Leu Thr Thr Lys Ala Phe Glu Gly Val Glu Lys Leu
                20                  25                  30

Ile Glu Leu Asn Leu Gln Val Val Lys Ser Thr Leu Ala Glu Ser Gln
            35                  40                  45

Glu Asn Val Gln Arg Ala Leu Ser Val Lys Asp Ala Gln Glu Leu Leu
        50                  55                  60

Ala Leu Gln Ala Ser Leu Thr Gln Pro Ile Ala Glu Lys Val Leu Ala
65                  70                  75                  80
```

Tyr Gly Arg His Val Tyr Glu Ile Ala Ser Ala Thr Gln Ala Glu Phe
            85                  90                  95

Ala Lys Val Ala Glu Ala Gln Tyr Glu Gln Asn Arg Lys Val Gln
        100                 105                 110

Ala Leu Val Asp Asn Val Ala Lys Asn Ala Pro Ala Gly Ser Glu Thr
        115                 120                 125

Ala Val Ala Ala Leu Lys Ser Ala Ile Asn Ala Asn Thr Thr Tyr
130                 135                 140

Glu Thr Val Gln Lys Ala Lys Gln Ala Val Glu Ile Ala Glu Thr
145                 150                 155                 160

Asn Phe Asn Ala Ala Ala Val Ala Thr Lys Ala Ala Asn Thr Ala
                165                 170                 175

Ala Ala Ala Ser Arg Arg Ser Gly Lys Thr Ala
                180                 185

<210> SEQ ID NO 44
<211> LENGTH: 188
<212> TYPE: PRT
<213> ORGANISM: Artificial Sequence
<220> FEATURE:
<223> OTHER INFORMATION: Sequence derived from Burkholderia
      vietnamiensis G4

<400> SEQUENCE: 44

Met Ser Leu Leu Thr Pro Glu Gln Ile Ala Ala Gln Lys Ala Asn
1               5                   10                  15

Leu Glu Ser Leu Phe Gly Leu Thr Thr Lys Ala Phe Glu Gly Val Glu
            20                  25                  30

Lys Leu Ile Glu Leu Asn Leu Gln Val Val Lys Ser Thr Leu Thr Glu
        35                  40                  45

Ser Gln Glu Asn Ala Gln Arg Leu Leu Ser Val Lys Asp Ala Gln Glu
    50                  55                  60

Leu Ile Ala Leu Gln Ala Ser Leu Ser Gln Pro Val Ala Glu Lys Val
65                  70                  75                  80

Leu Ser Tyr Ser Arg His Leu Tyr Glu Ile Ala Ser Ala Thr Gln Ala
                85                  90                  95

Glu Phe Ala Lys Val Ala Glu Ala Gln Phe Asp Glu Gln Asn Lys Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Asn Thr
    130                 135                 140

Thr Tyr Glu Thr Val Gln Lys Ala Ala Lys Gln Ala Val Glu Ile Ala
145                 150                 155                 160

Glu Thr Asn Phe Asn Ala Ala Ala Val Ala Thr Lys Ala Ala Thr
                165                 170                 175

Ala Ala Ala Ser Arg Arg Ser Ser Lys Pro Ala Ala
                180                 185

<210> SEQ ID NO 45
<211> LENGTH: 189
<212> TYPE: PRT
<213> ORGANISM: Artificial Sequence
<220> FEATURE:
<223> OTHER INFORMATION: Sequence derived from Burkholderia pseudomallei
      K96243

<400> SEQUENCE: 45

Met Ser Leu Leu Thr Pro Glu Gln Ile Ala Ala Gln Lys Ala Asn
1               5                   10                  15

Ile Glu Ser Leu Phe Gly Leu Thr Thr Lys Ala Phe Glu Gly Val Glu
            20                  25                  30

Lys Leu Ile Glu Leu Asn Leu Gln Val Val Lys Ser Thr Leu Ala Glu
            35                  40                  45

Ser Gln Glu Asn Val Gln Arg Ala Leu Ser Val Lys Asp Ala Gln Glu
        50                  55                  60

Leu Leu Ala Leu Gln Ala Ser Leu Thr Gln Pro Ile Ala Glu Lys Val
65                  70                  75                  80

Leu Ala Tyr Gly Arg His Val Tyr Glu Ile Ala Ser Ala Thr Gln Ala
                85                  90                  95

Glu Phe Ala Lys Val Ala Glu Ala Gln Tyr Glu Glu Gln Asn Arg Lys
            100                 105                 110

Val Gln Ala Leu Val Asp Asn Val Ala Lys Asn Ala Pro Ala Gly Ser
            115                 120                 125

Glu Thr Ala Val Ala Ala Leu Lys Ser Ala Ile Asn Ala Ala Asn Thr
        130                 135                 140

Thr Tyr Glu Thr Val Gln Lys Ala Ala Lys Gln Ala Val Glu Ile Ala
145                 150                 155                 160

Glu Thr Asn Phe Asn Ala Ala Ala Val Ala Thr Lys Ala Ala Asn
                165                 170                 175

Thr Ala Ala Ala Ser Arg Arg Ser Gly Lys Thr Ala
            180                 185

<210> SEQ ID NO 46
<211> LENGTH: 191
<212> TYPE: PRT
<213> ORGANISM: Artificial Sequence
<220> FEATURE:
<223> OTHER INFORMATION: Sequence derived from Burkholderia
      thailandensis E264

<400> SEQUENCE: 46

Met Ser Leu Leu Thr Pro Glu Gln Ile Ala Ala Gln Lys Ala Asn
1               5                   10                  15

Ile Glu Ser Leu Phe Gly Leu Thr Thr Lys Ala Phe Glu Gly Val Glu
            20                  25                  30

Lys Leu Ile Glu Leu Asn Leu Gln Val Val Lys Ser Thr Leu

```
Thr Ala Ala Ala Ala Ser Arg Arg Ser Gly Thr Gly Lys Thr Ala
            180                 185                 190

<210> SEQ ID NO 47
<211> LENGTH: 191
<212> TYPE: PRT
<213> ORGANISM: Artificial Sequence
<220> FEATURE:
<223> OTHER INFORMATION: Sequence derived from Burkholderia mallei
      GB8 horse 4

<400> SEQUENCE: 47

Met Asn Met Ser Leu Leu Thr Pro Glu Gln Ile Ala Ala Gln Lys
1               5                   10                  15

Ala Asn Ile Glu Ser Leu Phe Gly Leu Thr Thr Lys Ala Phe Glu Gly
                20                  25                  30

Val Glu Lys Leu Ile Glu Leu Asn Leu Gln Val Val Lys Ser Thr Leu
            35                  40                  45

Ala Glu Ser Gln Glu Asn Val Gln Arg Ala Leu Ser Val Lys Asp Ala
        50                  55                  60

Gln Glu Leu Leu Ala Leu Gln Ala Ser Leu Thr Gln Pro Ile Ala Glu
65                  70                  75                  80

Lys Val Leu Ala Tyr Gly Arg His Val Tyr Glu Ile Ala Ser Ala Thr
                85                  90                  95

Gln Ala Glu Phe Ala Lys Val Ala Glu Ala Gln Tyr Glu Glu Gln Asn
            100                 105                 110

Arg Lys Val Gln Ala Leu Val Asp Asn Val Ala Lys Asn Ala Pro Ala
        115                 120                 125

Gly Ser Glu Thr Ala Val Ala Ala Leu Lys Ser Ala Ile Asn Ala Ala
    130                 135                 140

Asn Thr Thr Tyr Glu Thr Val Gln Lys Ala Ala Lys Gln Ala Val Glu
145                 150                 155                 160

Ile Ala Glu Thr Asn Phe Asn Ala Ala Ala Val Ala Thr Lys Ala
                165                 170                 175

Ala Asn Thr Ala Ala Ala Ala Ser Arg Arg Ser Gly Lys Thr Ala
            180                 185                 190

<210> SEQ ID NO 48
<211> LENGTH: 190
<212> TYPE: PRT
<213> ORGANISM: Artificial Sequence
<220> FEATURE:
<223> OTHER INFORMATION: Sequence derived from Burkholderia xenovorans
      LB400

<400> SEQUENCE: 48

Met Thr Leu Leu Thr Pro Glu Gln Phe Ala Ala Gln Lys Ala Asn
1               5                   10                  15

Phe Glu Thr Leu Phe Gly Leu Thr Thr Lys Ala Phe Glu Gly Val Glu
                20                  25                  30

Lys Leu Val Glu Leu Asn Leu Gln Val Val Lys Ser Thr Leu Ala Glu
            35                  40                  45

Ser Gln Glu Asn Ala Gln Arg Ala Leu Ser Val Lys Asp Ala Gln Glu
        50                  55                  60

Leu Leu Ala Leu Gln Ala Ser Leu Ala Gln Pro Val Ala Glu Lys Ala
65                  70                  75                  80

Leu Ser Tyr Gly Arg His Val Tyr Glu Ile Val Ser Ala Thr Gln Gly
                85                  90                  95
```

Glu Phe Ala Arg Val Ala Glu Ala Gln Phe Glu Gln Asn Arg Lys
                100                 105                 110

Val Gln Ser Leu Val Glu Asn Val Ala Lys Asn Ala Pro Ala Gly Ser
            115                 120                 125

Glu Thr Ala Val Ala Val Met Lys Ser Ala Ile Thr Ala Ala Asn Thr
        130                 135                 140

Thr Tyr Glu Thr Val His Lys Ala Thr Lys Gln Ala Val Glu Ile Ala
145                 150                 155                 160

Glu Ser Asn Phe Asn Ala Ala Ala Thr Ala Ala Ser Lys Ala Ala Ser
                165                 170                 175

Gln Ala Ala Ala Gln Ala Ser Arg Ser Ala Lys Lys Ala Val
            180                 185                 190

<210> SEQ ID NO 49
<211> LENGTH: 193
<212> TYPE: PRT
<213> ORGANISM: Artificial Sequence
<220> FEATURE:
<223> OTHER INFORMATION: Sequence derived from Burkholderia
      thailandensis MSMB43

<400> SEQUENCE: 49

Met Asn Met Ser Leu Leu Thr Pro Glu Gln Ile Ala Ala Ala Gln Lys
1

```
Met Asn Met Ser Leu Leu Thr Pro Glu Gln Ile Ala Ala Ala Gln Lys
1               5                   10                  15

Thr Asn Ile Glu Ser Leu Phe Gly Leu Thr Lys Ala Phe Glu Gly
            20                  25                  30

Val Glu Lys Leu Ile Glu Leu Asn Leu Gln Val Val Lys Ser Thr Leu
            35                  40                  45

Ala Glu Ser Gln Glu Asn Val Gln Arg Ala Leu Ser Val Lys Asp Ala
        50                  55                  60

Gln Glu Leu Leu Ala Leu Gln Ala Ser Leu Thr Gln Pro Ile Ala Glu
65                  70                  75                  80

Lys Val Leu Ala Tyr Gly Arg His Val Tyr Glu Ile Ala Ser Ala Thr
                85                  90                  95

Gln Ala Glu Phe Ala Lys Val Ala Glu Ala Gln Tyr Glu Glu Gln Asn
                100                 105                 110

Arg Lys Val Gln Ala Leu Val Asp Asn Val Ala Lys Asn Ala Pro Ala
            115                 120                 125

Gly Ser Glu Thr Ala Val Ala Ala Leu Lys Ser Ala Ile Asn Ala Ala
    130                 135                 140

Asn Thr Thr Tyr Glu Thr Val Gln Lys Ala Ala Lys Gln Ala Val Glu
145                 150                 155                 160

Ile Ala Glu Thr Asn Phe Asn Ala Ala Ala Val Ala Thr Lys Ala
                165                 170                 175

Ala Asn Thr Ala Ala Ala Ser Arg Arg Ser Gly Lys Thr Ala Ala
            180                 185                 190

<210> SEQ ID NO 51
<211> LENGTH: 191
<212> TYPE: PRT
<213> ORGANISM: Artificial Sequence
<220> FEATURE:
<223> OTHER INFORMATION: Sequence derived from Burkholderia sp. H160

<400> SEQUENCE: 51

Met Thr Leu Leu Thr Pro Glu Gln Phe Ala Ala Ala Gln Lys Ala Asn
1               5                   10                  15

Phe Glu Thr Leu Phe Gly Leu Thr Lys Ala Phe Glu Gly Val Glu
            20                  25                  30

Lys Leu Val Glu Leu Asn Leu Gln Val Val Lys Ser Thr Leu Ala Glu
            35                  40                  45

Ser Gln Glu Asn Thr Gln Arg Ala Leu Ser Val Lys Asp Ala Gln Glu
        50                  55                  60

Leu Leu Ala Leu Gln Ala Ser Leu Ala Gln Pro Val Ala Glu Lys Ala
65                  70                  75                  80

Leu Ser Tyr Gly Arg His Val Tyr Glu Ile Val Ser Ala Thr Gln Gly
                85                  90                  95

Glu Phe Ala Arg Val Ala Glu Ala Gln Phe Glu Glu Gln Asn Arg Lys
                100                 105                 110

Val Gln Ala Leu Val Glu Asn Val Ala Lys Asn Ala Pro Ala Gly Ser
            115                 120                 125

Glu Thr Ala Val Ala Val Met Lys Ser Ala Ile Thr Ala Ala Asn Thr
    130                 135                 140

Thr Tyr Glu Thr Val His Lys Ala Thr Arg Gln Ala Val Glu Ile Ala
145                 150                 155                 160

Glu Ser Asn Phe Asn Ala Ala Thr Ala Ala Ser Lys Ala Ala Ser
            165                 170                 175
```

Gln Ala Ala Ala Gln Ala Ser Arg Ala Ala Ala Lys Lys Ala Val
180 185 190

<210> SEQ ID NO 52
<211> LENGTH: 242
<212> TYPE: PRT
<213> ORGANISM: Artificial Sequence
<220> FEATURE:
<223> OTHER INFORMATION: Sequence derived from Ralstonia solanacearum MolK2
<220> FEATURE:
<221> NAME/KEY: MISC_FEATURE
<222> LOCATION: (1)..(48)
<223> OTHER INFORMATION: Xaa denotes that the residue sequence is currently unknown

<400> SEQUENCE: 52

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Gly Thr Thr Gln Glu Gln Ile Ala Ala Ala Gln Lys Ala Asn Leu Gln
50 55 60

Tyr Phe Phe Gly Leu Thr Asn Lys Ala Phe Glu Gly Val Pro Leu Leu
65 70 75 80

Val Glu Leu Asn Leu Gln Val Val Lys Ala Thr Leu Ala Glu Asn Val
85 90 95

Glu His Ser Lys Lys Ala Leu Ser Ala Lys Asp Ala Gln Glu Leu Leu
100 105 110

Ala Val His Thr Ala Ala Val Gln Pro Leu Ala Glu Lys Val Leu Ala
115 120 125

Tyr Asn Arg His Leu Tyr Glu Ile Phe Ser Asp Thr Gln Thr Glu Phe
130 135 140

Gly Lys Val Ala Glu Thr Gln Ile Ala Glu Asn Gly Arg Lys Leu Gln
145 150 155 160

Ala Leu Ile Asp Asn Val Ser Lys Asn Ala Pro Ala Gly Ser Glu Ser
165 170 175

Ala Val Ala Leu Val Lys Ser Ala Leu Ser Ala Ala Asn Asn Ala Tyr
180 185 190

Asp Ser Val Gln Lys Ala Thr Lys Gln Ala Val Glu Leu Ala Glu Ser
195 200 205

Asn Phe His Ala Ala Ala Asn Ala Ala Ser Lys Ala Thr Ala Gln Ala
210 215 220

Ala Ala Gln Ala Arg Ala Ala Thr Thr Ser Lys Lys Ser Thr Thr Thr
225 230 235 240

Ala Ala

<210> SEQ ID NO 53
<211> LENGTH: 193
<212> TYPE: PRT
<213> ORGANISM: Artificial Sequence
<220> FEATURE:
<223> OTHER INFORMATION: Sequence derived from Burkholderia glumae BGR1

<400> SEQUENCE: 53

Met Ser Leu Leu Thr Pro Glu Gln Ile Ala Ala Ala His Lys Ala Asn
1 5 10 15

```
Leu Glu Ser Leu Phe Gly Leu Thr Ser Lys Ala Phe Glu Ser Val Glu
            20                  25                  30

Lys Leu Ile Glu Leu Asn Val Gln Val Val Lys Ser Thr Leu Ala Glu
        35                  40                  45

Ser Gln Glu Asn Ala Gln Arg Ala Leu Ser Ala Lys Asp Ala Gln Glu
    50                  55                  60

Leu Ile Ala Leu Gln Ala Ser Phe Ala Gln Pro Val Ala Glu Lys Met
65                  70                  75                  80

Leu Ala Tyr Gly Arg His Leu Tyr Asp Ile Ala Ser Thr Thr Gln Ala
                85                  90                  95

Glu Phe Ala Lys Val Ala Glu Ala Gln Phe Gln Glu Gln Asn Leu Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Ile Asn Ala Ala Asn Thr
    130                 135                 140

Thr Tyr Glu Thr Val Gln Lys Ala Thr Lys Gln Ala Val Glu Ile Ala
145                 150                 155                 160

Glu Ser Asn Phe Asn Ala Ala Ala Val Ala Thr Lys Ala Ala Asn
                165                 170                 175

Ser Ala Ala Ala Ala Ser Arg Arg Thr Ala Ala Ala Pro Lys Ala
            180                 185                 190

Val

<210> SEQ ID NO 54
<211> LENGTH: 188
<212> TYPE: PRT
<213> ORGANISM: Artificial Sequence
<220> FEATURE:
<223> OTHER INFORMATION: Sequence derived from Burkholderia ubonensis Bu

<400> SEQUENCE: 54

Met Ser Leu Leu Thr Pro Glu Gln Ile Ala Ala Ala Gln Lys Ala Asn
1               5                   10                  15

Leu Glu Ser Leu Phe Gly Leu Thr Thr Thr Ala Phe Asp Gly Ile Glu
            20                  25                  30

Lys Leu Ile Glu Leu Asn Val Gln Val Val Lys Ser Thr Leu Ala Glu
        35                  40                  45

Thr Gln Glu Asn Ala Gln Arg Leu Leu Ser Val Lys Asp Ala Gln Glu
    50                  55                  60

Leu Ile Ala Leu Gln Ala Ser Leu Thr Gln Pro Val Ala Glu Lys Val
65                  70                  75                  80

Leu Ala Tyr Gly Arg His Val Tyr Glu Ile Ala Ser Ala Thr Gln Ala
                85                  90                  95

Glu Phe Ala Lys Val Ala Glu Ala Gln Tyr Glu Gln Asn Lys Lys
            100                 105                 110

Val Gln Ala Leu Val Asp Asn Val Ala Lys Asn Ala Pro Ala Gly Ser
        115                 120                 125

Glu Thr Ala Val Ala Ala Leu Lys Ser Ala Leu Asn Ala Ala Ser Thr
    130                 135                 140

Thr Tyr Glu Thr Val Gln Lys Ala Lys Gln Ala Val Glu Ile Ala
145                 150                 155                 160

Glu Thr Asn Phe Asn Ala Ala Ala Val Ala Thr Lys Ala Ala Ser
                165                 170                 175

Ala Ala Ala Ser Arg Arg Ala Thr Lys Pro Ala Ala
            180                 185
```

<210> SEQ ID NO 55
<211> LENGTH: 182
<212> TYPE: PRT
<213> ORGANISM: Artificial Sequence
<220> FEATURE:
<223> OTHER INFORMATION: Sequence derived from Comamonas testosteroni CNB-2

<400> SEQUENCE: 55

```
Met Ser Leu Thr Pro Asp Gln Ile Leu Ser Ala Gln Lys Ala His Phe
1               5                   10                  15

Glu Thr Leu Phe Gly Leu Thr Ser Lys Ala Phe Glu Gly Val Glu Lys
            20                  25                  30

Leu Val Glu Leu Asn Val Thr Ala Ser Arg Ala Ala Leu Ala Glu Ala
        35                  40                  45

Ala Gln His Thr Gln Ala Val Leu Ser Val Lys Asp Ala Gln Glu Leu
    50                  55                  60

Leu Thr Leu Gln Ala Gly Leu Phe Gln Pro Leu Ala Glu Lys Thr Ala
65                  70                  75                  80

Ser Tyr Ser Arg His Leu Tyr Asp Ile Ala Ser Asn Thr Ala Gly Glu
                85                  90                  95

Phe Asn Lys Thr Leu Glu Ala Gln Ser Thr Glu Ala Arg Lys Asn Phe
            100                 105                 110

Asn Ala Leu Leu Asp Asn Thr Thr Lys Asn Ala Pro Ala Gly Ser Glu
        115                 120                 125

Ser Ala Val Ala Met Val Lys Ser Ala Val Ser Ala Ala Asn Asn Ala
    130                 135                 140

Phe Glu Ser Val Gln Lys Ala Val Lys Gln Ala Ser Asp Met Ala Glu
145                 150                 155                 160

Ala Asn Phe Asn Ala Ala Thr Lys Thr Ala Thr Glu Ala Val Lys Ala
                165                 170                 175

Thr Thr Ala Ala Lys Arg
            180
```

<210> SEQ ID NO 56
<211> LENGTH: 182
<212> TYPE: PRT
<213> ORGANISM: Artificial Sequence
<220> FEATURE:
<223> OTHER INFORMATION: Sequence derived from Delftia acidovorans SPH-1

<400> SEQUENCE: 56

```
Met Ser Leu Thr Pro Asp Gln Ile Leu Ser Ala Gln Lys Ala Asn Leu
1               5                   10                  15

Glu Thr Leu Phe Gly Leu Thr Ser Lys Ala Phe Glu Gly Val Glu Lys
            20                  25                  30

Leu Val Glu Leu Asn Val Thr Ala Ser Arg Ala Ala Leu Thr Glu Ala
        35                  40                  45

Ala Gln His Thr Gln Ala Val Leu Ser Val Lys Asp Ala Gln Glu Leu
    50                  55                  60

Leu Ser Leu Gln Ala Asn Leu Phe Gln Pro Leu Ala Glu Lys Thr Ala
65                  70                  75                  80

Ala Tyr Ser Arg His Leu Tyr Asp Ile Ala Ser Gly Thr Gly Ala Glu
                85                  90                  95

Leu Ala Lys Thr Phe Glu Ser Gln Ala Ser Asp Leu Gln Lys Asn Phe
            100                 105                 110
```

Ser Ala Leu Val Asp Thr Thr Ala Lys Asn Ala Pro Ala Gly Ser Glu
    115        120        125

Thr Ala Val Ala Val Met Lys Ser Ala Val Ser Ala Ala Asn Asn Ala
 130        135        140

Phe Glu Ser Val Gln Lys Ala Val Lys Gln Ala Ser Asp Leu Ala Glu
145        150        155        160

Ala Asn Phe Thr Ala Val Thr Asn Thr Ala Ser Glu Ala Val Gln Ser
     165        170        175

Ala Gln Thr Arg Lys Arg
     180

<210> SEQ ID NO 57
<211> LENGTH: 182
<212> TYPE: PRT
<213> ORGANISM: Artificial Sequence
<220> FEATURE:
<223> OTHER INFORMATION: Sequence derived from Comamonas testosteroni
   KF-1

<400> SEQUENCE: 57

Met Ser Leu Thr Pro Asp Gln Ile Leu Ser Ala Gln Lys Ala His Phe
1        5        10        15

Glu Thr Leu Phe Gly Leu Thr Ser Lys Ala Phe Glu Gly Val Glu Lys
     20        25        30

Leu Val Glu Leu Asn Val Thr Ala Ser Arg Ala Ala Leu Thr Glu Ala
   35        40        45

Ala Gln His Thr Gln Ala Val Leu Ser Val Lys Asp Ala Gln Glu Leu
 50        55        60

Leu Thr Leu Gln Ala Gly Leu Phe Gln Pro Leu Ala Glu Lys Thr Ala
65        70        75        80

Ser Tyr Ser Arg His Leu Tyr Asp Ile Ala Ser Asn Thr Ala Gly Glu
     85        90        95

Phe Asn Lys Ala Leu Glu Val Gln Ser Thr Glu Ala Arg Lys Ser Phe
     100        105        110

Asn Ser Leu Leu Asp Asn Ser Thr Lys Asn Ala Pro Ala Gly Ser Glu
    115        120        125

Ser Ala Val Ala Met Val Lys Ser Ala Val Ser Ala Ala Asn Asn Ala
 130        135        140

Phe Glu Ser Val Gln Lys Ala Val Lys Gln Ala Ser Asp Met Ala Glu
145        150        155        160

Ala Asn Phe Asn Ala Ala Thr Lys Thr Ala Thr Glu Ala Val Lys Ala
     165        170        175

Thr Thr Thr Ala Lys Arg
     180

<210> SEQ ID NO 58
<211> LENGTH: 180
<212> TYPE: PRT
<213> ORGANISM: Artificial Sequence
<220> FEATURE:
<223> OTHER INFORMATION: Sequence derived from Rhodoferax ferrireducens
   T118

<400> SEQUENCE: 58

Met Leu Thr Val Glu Gln Val Leu Ala Ser Gln Lys Ala Asn Val Glu
1        5        10        15

Thr Leu Leu Gly Leu Thr Ser Lys Ala Phe Glu Gly Met Glu Arg Ile
     20        25        30

Val Glu Leu Asn Met Thr Ala Ser Lys Ala Ala Leu Ala Glu Thr Ser
             35                  40                  45

Glu Thr Ala Lys Ala Phe Leu Ser Ala Lys Asp Ala Gln Glu Leu Leu
 50                  55                  60

Ala Leu Gln Ser Ser Leu Met Gln Pro Leu Ala Glu Lys Thr Ala Ala
 65                  70                  75                  80

Tyr Ser Arg His Leu Tyr Asp Ile Ala Thr Gly Ser Ser Ala Glu Phe
                 85                  90                  95

Ser Lys Ala Phe Glu Ala Gln Thr Ala Glu Gln Gln Lys Phe Met
                100                 105                 110

Gly Leu Val Asp Asn Val Ala Lys Asn Ala Pro Ala Gly Ser Glu Ser
                115                 120                 125

Ala Val Ala Val Met Lys Ser Ala Val Ala Ala Ser Asn Ala Met
                130                 135                 140

Glu Ser Val Gln Lys Ala Val Gln Gln Ala Thr Glu Val Ala Glu Ala
145                 150                 155                 160

Asn Phe Asn Ala Val Ser Ala Thr Ala Val Asn Ala Ala Lys Pro Ala
                    165                 170                 175

Gly Lys Lys Arg
            180

<210> SEQ ID NO 59
<211> LENGTH: 180
<212> TYPE: PRT
<213> ORGANISM: Artificial Sequence
<220> FEATURE:
<223> OTHER INFORMATION: Sequence derived from Polaromonas sp. JS666

<400> SEQUENCE: 59

Met Leu Thr Ala Glu Gln Val Leu Ala Ser His Lys Ala Asn Ile Glu
 1               5                  10                  15

Thr Leu Phe Gly Leu Thr Ser Lys Ala Phe Glu Gly Val Glu Lys Leu
                 20                  25                  30

Val Glu Leu Asn Val Gln Ala Thr Lys Ala Ala Leu Ala Glu Thr Ala
             35                  40                  45

Asn His Thr Gln Ala Val Leu Gly Ala Lys Asp Ala Gln Glu Leu Leu
 50                  55                  60

Ala Leu Gln Ala Gly Leu Val Gln Pro Leu Ala Glu Lys Thr Ala Ala
 65                  70                  75                  80

Tyr Ser Arg His Ile Tyr Asp Ile Ala Thr Ala Ala Ser Ala Glu Leu
                 85                  90                  95

Ser Lys Thr Phe Glu Gly Gln Ala Ala Asp Ala Gln Lys Lys Phe Val
                100                 105                 110

Gly Ile Val Asp Asn Ala Ala Lys Asn Ala Pro Ala Gly Ser Glu Thr
                115                 120                 125

Ala Val Ala Val Met Lys Ser Ala Val Ala Ala Asn Asn Ala Phe
                130                 135                 140

Glu Ser Val Gln Lys Ala Val Lys Gln Ala Ser Asp Ile Ala Glu Ala
145                 150                 155                 160

Asn Phe Asn Thr Val Ala Ala Ser Ala Val Asn Ala Ser Lys Thr Val
                    165                 170                 175

Ser Lys Lys Arg
            180

<210> SEQ ID NO 60

```
<211> LENGTH: 187
<212> TYPE: PRT
<213> ORGANISM: Artificial Sequence
<220> FEATURE:
<223> OTHER INFORMATION: Sequence derived from Acidovorax sp. JS42

<400> SEQUENCE: 60
```

| Met | Ser | Leu | Thr | Pro | Glu | Gln | Ile | Leu | Ala | Ser | His | Lys | Ala | Asn | Leu |
|---|---|---|---|---|---|---|---|---|---|---|---|---|---|---|---|
| 1 | | | | 5 | | | | | 10 | | | | | 15 | |

Glu Thr Leu Phe Gly Leu Thr Asn Lys Ala Phe Glu Gly Val Glu Lys
            20                  25                  30

Leu Val Glu Leu Asn Val Thr Ala Ser Arg Ala Ala Leu Ala Glu Ala
        35                  40                  45

Ala Ser His Thr Gln Ala Val Leu Ser Ala Lys Asp Ala Gln Glu Leu
    50                  55                  60

Leu Ala Leu Gln Ala Ser Leu Phe Gln Pro Leu Ala Glu Lys Ala Leu
65                  70                  75                  80

Ala Tyr Ser Arg His Leu Tyr Asp Ile Ala Ser Gly Met Gly Ala Glu
                85                  90                  95

Phe Gly Lys Thr Phe Glu Ala Gln Ala Ala Glu Val Gln Arg Asn Phe
            100                 105                 110

Thr Asn Leu Val Asp Ser Ala Ala Lys Asn Ala Pro Ala Gly Ser Glu
        115                 120                 125

Thr Thr Val Ala Val Phe Lys Ser Ala Val Ser Ala Ala Asn Asn Ala
    130                 135                 140

Phe Glu Ser Val Gln Lys Ala Val Lys Gln Ala Ser Asp Val Ala Glu
145                 150                 155                 160

Ala Asn Phe Asn Ala Val Ala Ser Ser Ala Ala Thr Ala Ala Lys Thr
                165                 170                 175

Ala Thr Ala Ala Thr Ala Ala Pro Arg Lys Arg
            180                 185

```
<210> SEQ ID NO 61
<211> LENGTH: 180
<212> TYPE: PRT
<213> ORGANISM: Artificial Sequence
<220> FEATURE:
<223> OTHER INFORMATION: Sequence derived from Polaromonas
      naphthalenivorans CJ2

<400> SEQUENCE: 61
```

Met Leu Thr Ala Glu Gln Leu Met Ala Ser His Lys Ala Asn Ile Glu
1               5                   10                  15

Thr Leu Phe Gly Leu Thr Gln Lys Ala Phe Glu Gly Val Glu Lys Leu
            20                  25                  30

Val Glu Leu Asn Val Gln Ala Thr Lys Ala Ala Leu Ala Glu Thr Ala
        35                  40                  45

Asn Asn Ala Gln Ala Val Leu Asn Ala Lys Asp Ala Gln Glu Leu Leu
    50                  55                  60

Ala Leu Gln Ala Ser Met Val Gln Pro Leu Ala Glu Lys Thr Ala Ala
65                  70                  75                  80

Tyr Ser Arg His Leu Tyr Asp Ile Ala Gln Ser Ala Gly Ala Glu Phe
                85                  90                  95

Ser Lys Thr Leu Glu Gly Gln Thr Ala Glu Ala Gln Lys Lys Phe Ala
            100                 105                 110

Asp Leu Val Glu Ser Ala Thr Gln Asn Ala Pro Ala Gly Ser Glu Thr
        115                 120                 125

```
Ala Val Thr Met Met Lys Ser Ala Met Thr Ala Ala Asn Ser Ala Phe
            130                 135                 140

Glu Ser Val Gln Lys Ala Val Lys Gln Ala Gly Asp Met Ala Glu Thr
145                 150                 155                 160

Asn Phe Asn Thr Val Ser Glu Ser Ala Val Asn Ala Ser Lys Ser Val
                165                 170                 175

Ser Lys Lys Arg
            180

<210> SEQ ID NO 62
<211> LENGTH: 187
<212> TYPE: PRT
<213> ORGANISM: Artificial Sequence
<220> FEATURE:
<223> OTHER INFORMATION: Sequence derived from Acidovorax ebreus TPSY

<400> SEQUENCE: 62

Met Ser Leu Thr Pro Glu Gln Ile Leu Ala Ser His Lys Ala Asn Leu
1               5                   10                  15

Glu Thr Leu Phe Gly Leu Thr Asn Lys Ala Phe Glu Gly Val Glu Lys
                20                  25                  30

Leu Val Glu Leu Asn Val Thr Ala Ser Arg Ala Ala Leu Ala Glu Ala
            35                  40                  45

Ala Ser His Thr Gln Ala Val Leu Ser Thr Lys Asp Ala Gln Glu Leu
        50                  55                  60

Leu Ala Leu Gln Ala Ser Leu Phe Gln Pro Leu Ala Glu Lys Ala Val
65                  70                  75                  80

Ala Tyr Ser Arg His Leu Tyr Asp Ile Ala Ser Gly Thr Gly Ala Glu
                85                  90                  95

Phe Gly Lys Thr Phe Glu Ala Gln Ala Ala Glu Val Gln Arg Asn Phe
            100                 105                 110

Thr Asn Leu Val Asp Ser Ala Ala Lys Asn Ala Pro Ala Gly Ser Glu
        115                 120                 125

Thr Thr Val Ala Val Phe Lys Ser Ala Val Ser Ala Ala Asn Asn Ala
    130                 135                 140

Phe Glu Ser Val Gln Lys Ala Val Lys Gln Ala Ser Asp Val Ala Glu
145                 150                 155                 160

Ala Asn Phe Asn Ala Val Ala Ser Ser Ala Ala Thr Ala Ala Lys Thr
                165                 170                 175

Ala Thr Ala Ala Thr Ala Ala Pro Arg Lys Arg
            180                 185

<210> SEQ ID NO 63
<211> LENGTH: 184
<212> TYPE: PRT
<213> ORGANISM: Artificial Sequence
<220> FEATURE:
<223> OTHER INFORMATION: Sequence derived from Alicycliphilus
      denitrificans BC

<400> SEQUENCE: 63

Met Ser Leu Thr Pro Glu Gln Ile Leu Ala Ser His Lys Ala Asn Ile
1               5                   10                  15

Glu Thr Leu Phe Gly Leu Thr Asn Lys Ala Phe Glu Gly Val Glu Lys
                20                  25                  30

Leu Val Gln Leu Asn Val Ala Ala Ser Arg Ala Ala Leu Thr Glu Ala
            35                  40                  45

Ala Thr His Ala Gln Ala Val Leu Ser Val Lys Asp Ala Gln Glu Leu
```

```
Leu Ala Leu Gln Ala Gly Leu Phe Gln Pro Leu Ala Glu Lys Ala Ala
 65                  70                  75                  80

Ala Tyr Ser Arg His Val Tyr Glu Ile Ala Ser Gly Thr Gly Ala Glu
                 85                  90                  95

Phe Gly Lys Ala Phe Glu Ser Gln Ala Ala Glu Ala Gln Arg Asn Phe
            100                 105                 110

Ser Asn Leu Val Asp Thr Ala Ala Lys Asn Ala Pro Ala Gly Ser Glu
        115                 120                 125

Thr Thr Val Ala Val Phe Lys Ser Ala Val Ser Ala Ala Asn Asn Ala
130                 135                 140

Phe Glu Ser Val Gln Lys Ala Val Lys Gln Ala Ser Asp Val Ala Glu
145                 150                 155                 160

Ala Asn Phe Asn Ala Val Ala Asn Ser Ala Ala Asn Ala Ala Lys Thr
                165                 170                 175

Val Glu Val Ala Ala Arg Lys Arg
            180
```

<210> SEQ ID NO 64
<211> LENGTH: 192
<212> TYPE: PRT
<213> ORGANISM: Artificial Sequence
<220> FEATURE:
<223> OTHER INFORMATION: Sequence derived from Acidovorax avenae subsp.
      citrulli AAC00-1

<400> SEQUENCE: 64

```
Met Ser Leu Thr Pro Glu Gln Leu Ile Ala Ser Gln Lys Ala His Leu
1               5                   10                  15

Asp Thr Leu Phe Gly Leu Thr Asn Lys Ala Phe Glu Gly Val Glu Lys
            20                  25                  30

Leu Val Glu Leu Asn Val Thr Ala Ser Arg Ala Thr Leu Ser Glu Ala
        35                  40                  45

Ala Thr His Thr Gln Ala Leu Leu Ser Val Lys Asp Ala Gln Glu Leu
 50                  55                  60

Leu Ser Leu Gln Ala Ala Phe Phe Gln Pro Leu Ala Glu Lys Thr Ala
 65                  70                  75                  80

Ala Tyr Asn Arg His Leu Tyr Glu Ile Ala Ser Gly Thr Thr Ala Glu
                 85                  90                  95

Phe Gly Arg Ala Phe Glu Ala Gln Ala Ala Glu Met Gln Arg Asn Phe
            100                 105                 110

Ser Asn Leu Val Asp Thr Ala Ala Arg Asn Ala Pro Ala Gly Thr Glu
        115                 120                 125

Thr Gly Val Ala Val Phe Lys Ser Ala Val Ser Ala Ala Asn Asn Ala
130                 135                 140

Phe Glu Thr Val Gln Lys Ala Val Lys Gln Ala Ser Asp Ala Ala Glu
145                 150                 155                 160

Ala Asn Phe Asn Ala Val Thr Asn Thr Ala Thr Ala Asn Ala Ala Thr
                165                 170                 175

Ala Thr Asn Ala Ala Ala Ala Thr Ser Ala Ala Met Arg Lys Arg
            180                 185                 190
```

<210> SEQ ID NO 65
<211> LENGTH: 184
<212> TYPE: PRT
<213> ORGANISM: Artificial Sequence
<220> FEATURE:

<223> OTHER INFORMATION: Sequence derived from Polynucleobacter
      necessarius subsp. asymbioticus QLW-P1DMWA-1

<400> SEQUENCE: 65

Met Asn Leu Thr Pro Glu Gln Ile Ala Ala Ala Gln Lys Ala Asn Leu
1               5                   10                  15

Glu Thr Leu Ser Gly Leu Thr Asn Gln Ala Leu Gln Ser Ile Glu Lys
            20                  25                  30

Leu Val Glu Leu Asn Leu Ala Ile Ala Lys Gln Ser Leu Ser Asp Ser
        35                  40                  45

Val Asn Asn Ala Lys Lys Ala Leu Glu Val Lys Asp Ile Gln Gln Leu
    50                  55                  60

Leu Ala His Gln Ala Glu Thr Val Gln Pro Ile Ala Glu Lys Ile Ile
65                  70                  75                  80

Ser Tyr Ser Arg His Leu Tyr Glu Leu Ala His Glu Thr Gln Glu Ser
                85                  90                  95

Phe Thr Lys Ser Ala Glu Lys Glu Phe Gln Ala Gly Gln Glu Lys Met
            100                 105                 110

Asn Ala Leu Val Glu Glu Trp Thr Lys Asn Ala Pro Ala Gly Ser Asp
        115                 120                 125

Val Ala Val Gln Ala Leu Lys Gln Ala Ile Ala Ser Ala Asn Asn Val
    130                 135                 140

Tyr Glu Thr Ser Gln Lys Ala Val Lys His Ala Val Glu Val Ala Gln
145                 150                 155                 160

Thr Asn Ile Asn Thr Ala Thr Asp Ala Val Ala Lys Thr Thr Ser Ala
                165                 170                 175

Ala Ser Lys Ala Ser Lys Lys Lys
            180

<210> SEQ ID NO 66
<211> LENGTH: 186
<212> TYPE: PRT
<213> ORGANISM: Artificial Sequence
<220> FEATURE:
<223> OTHER INFORMATION: Sequence derived from Thiomonas sp. 3As

<400> SEQUENCE: 66

Met Met Thr Pro Glu Gln Phe Ala Ala Ala Gln Lys Ala Gln Phe Glu
1               5                   10                  15

Thr Phe Phe Gly Leu Ala Ala Lys Ser Met Asp Asn Met Glu Lys Leu
            20                  25                  30

Val Asp Leu Asn Met Gln Ala Val Lys Thr Ser Leu Gln Glu Ser Ala
        35                  40                  45

Asp His Thr Met Ala Leu Leu Ser Val Lys Asp Leu Gln Glu Leu Ser
    50                  55                  60

Thr Leu Gln Ser Gly Trp Met Gln Pro Met Ala Glu Lys Val Leu Ser
65                  70                  75                  80

Tyr Ser Arg His Ala Tyr Glu Ile Ala Ser Gly Ala Gln Ala Glu Leu
                85                  90                  95

Ala Lys Thr Ala Glu Ser Gln Ile Ser Glu Thr His Lys Lys Phe Met
            100                 105                 110

Asp Leu Ala Glu Ser Ala Ala Lys Asn Ala Pro Ala Gly Ser Glu Thr
        115                 120                 125

Ala Val Ala Met Met Lys Ser Ala Met Asn Ala Asn Asn Ala Tyr
    130                 135                 140

Asp Ser Val Gln Lys Val Thr Lys Gln Ala Ala Glu Ala Val Glu Ala

```
                145                 150                 155                 160
Asn Met Asn Ala Val Thr Ser Thr Ala Met Lys Ala Ala Gln Thr Thr
                    165                 170                 175

Ser Arg Thr Ala Ala Lys Arg Ala Ala Ala
                180                 185

<210> SEQ ID NO 67
<211> LENGTH: 186
<212> TYPE: PRT
<213> ORGANISM: Artificial Sequence
<220> FEATURE:
<223> OTHER INFORMATION: Sequence derived from Thiomonas intermedia K12

<400> SEQUENCE: 67

Met Met Thr Pro Glu Gln Phe Ala Ala Ala Gln Lys Ala Gln Phe Glu
1               5                   10                  15

Thr Phe Phe Gly Leu Ala Ala Lys Ser Met Asp Asn Met Glu Lys Leu
                20                  25                  30

Val Asp Leu Asn Met Gln Ala Val Lys Thr Ser Leu Gln Glu Ser Ala
            35                  40                  45

Asp His Thr Met Ala Leu Leu Ser Val Lys Asp Leu Gln Glu Leu Ser
        50                  55                  60

Thr Leu Gln Ser Gly Trp Met Gln Pro Met Ala Glu Lys Val Leu Ser
65                  70                  75                  80

Tyr Ser Arg His Ala Tyr Glu Ile Ala Ser Gly Ala Gln Ala Glu Leu
                85                  90                  95

Ala Lys Thr Ala Glu Ser Gln Ile Ser Glu Thr His Lys Lys Phe Met
            100                 105                 110

Asp Leu Ala Glu Ser Ala Ala Lys Asn Ala Pro Ala Gly Ser Glu Thr
        115                 120                 125

Ala Val Ala Met Met Lys Ser Ala Met Asn Ala Ala Asn Asn Ala Tyr
    130                 135                 140

Asp Ser Val Gln Lys Val Thr Lys Gln Ala Ala Glu Ala Val Glu Ala
145                 150                 155                 160

Asn Met Asn Ala Val Thr Ser Thr Ala Met Lys Ala Ala Gln Thr Thr
                    165                 170                 175

Ser Arg Thr Thr Ala Lys Arg Ala Ala Ala
                180                 185

<210> SEQ ID NO 68
<211> LENGTH: 182
<212> TYPE: PRT
<213> ORGANISM: Artificial Sequence
<220> FEATURE:
<223> OTHER INFORMATION: Sequence derived from Verminephrobacter
      eiseniae EF01-2

<400> SEQUENCE: 68

Met Thr Leu Thr Ala Glu Gln Ile Leu Ala Ser His Lys Ala Asn Ile
1               5                   10                  15

Glu Thr Leu Phe Gly Leu Thr Ser Lys Ala Phe Glu Gly Val Glu Lys
                20                  25                  30

Leu Val Glu Leu Asn Val Ser Ala Ser Arg Ala Ala Leu Ser Glu Val
            35                  40                  45

Ala Asn His Ala Gln Ala Val Leu Gly Val Lys Asp Ala Gln Glu Leu
        50                  55                  60

Leu Ala Leu Gln Ala Ser Leu Phe Gln Pro Leu Ala Glu Lys Thr Ala
65                  70                  75                  80
```

```
Ala Tyr Ser Arg His Leu Tyr Asp Ile Ala Ser Gly Thr Gly Ala Glu
                85                  90                  95

Phe Gly Lys Ala Phe Glu Thr Gln Ala Ser Asp Ala Gln Lys Ala Phe
            100                 105                 110

Ala Thr Leu Val Asp Ser Ala Ala Lys Asn Ala Pro Ala Gly Ser Glu
        115                 120                 125

Thr Ala Val Ala Val Met Lys Ser Ala Val Ser Ala Ala Thr Asn Ala
130                 135                 140

Phe Glu Ser Val Gln Lys Ala Val Lys Gln Ala Ser Asp Val Ala Glu
145                 150                 155                 160

Ala Asn Phe Asn Ala Val Ala Ser Thr Ala Ala Asn Ala Ala Lys Thr
                165                 170                 175

Val Ala Pro Arg Lys Arg
            180

<210> SEQ ID NO 69
<211> LENGTH: 192
<212> TYPE: PRT
<213> ORGANISM: Artificial Sequence
<220> FEATURE:
<223> OTHER INFORMATION: Sequence derived from Acidovorax avenae subsp.
      avenae ATCC 19860

<400> SEQUENCE: 69

Met Ser Leu Thr Pro Glu Gln Leu Ile Ala Ser Gln Lys Ala His Leu
1               5                   10                  15

Asp Thr Leu Phe Gly Leu Thr Asn Lys Ala Phe Glu Gly Val Glu Lys
            20                  25                  30

Leu Val Glu Leu Asn Val Thr Ala Ser Arg Ala Thr Leu Ser Glu Ala
        35                  40                  45

Ala Thr His Thr Gln Ala Leu Leu Ser Val Lys Asp Pro Gln Glu Leu
    50                  55                  60

Leu Ser Leu Gln Ala Ala Phe Phe Gln Pro Leu Ala Glu Lys Thr Ala
65                  70                  75                  80

Ala Tyr Asn Arg His Leu Tyr Glu Ile Ala Ser Gly Thr Thr Ala Glu
                85                  90                  95

Phe Gly Arg Ala Phe Glu Ala Gln Ala Ala Glu Ile Gln Arg Asn Phe
            100                 105                 110

Thr Asn Leu Val Asp Thr Ala Ala Arg Asn Ala Pro Ala Gly Thr Glu
        115                 120                 125

Thr Gly Val Ala Val Phe Lys Ser Ala Val Ser Ala Ala Asn Asn Ala
    130                 135                 140

Phe Glu Thr Val Gln Lys Ala Val Lys Gln Ala Ser Asp Ala Ala Glu
145                 150                 155                 160

Ala Asn Phe Asn Ala Val Thr Asn Thr Ala Thr Ala Asn Ala Ala Ser
                165                 170                 175

Ala Thr Asn Ala Ala Ala Ala Thr Ser Ala Ala Leu Arg Lys Arg
            180                 185                 190

<210> SEQ ID NO 70
<211> LENGTH: 183
<212> TYPE: PRT
<213> ORGANISM: Artificial Sequence
<220> FEATURE:
<223> OTHER INFORMATION: Sequence derived from Variovorax paradoxus S110

<400> SEQUENCE: 70
```

```
Met Ala Leu Thr Ala Asp Gln Ile Leu Ala Gln Lys Ala Asn Leu
1               5                   10                  15

Glu Thr Leu Phe Gly Leu Thr Thr Lys Ala Phe Glu Gly Val Glu Lys
            20                  25                  30

Leu Val Glu Leu Asn Val Thr Ala Ser Lys Ala Leu Ser Glu Ala
            35                  40                  45

Gln Ser Thr Ala Gln Ala Ala Leu Asn Val Lys Asp Ala Gln Glu Leu
    50                  55                  60

Leu Thr Leu Gln Ala Ser Leu Phe Gln Pro Leu Ala Glu Lys Thr Ala
65                  70                  75                  80

Ala Tyr Ser Arg His Leu Tyr Asp Ile Ala Gln Gly Thr Gly Ala Glu
                85                  90                  95

Phe Thr Lys Ala Phe Glu Ala Lys Ala Ala Glu Ala Gln Gln Thr Phe
            100                 105                 110

Val Gly Leu Val Asp Ser Ala Ser Lys Asn Ala Pro Ala Gly Ser Glu
            115                 120                 125

Thr Ala Val Ala Val Leu Lys Ser Ala Val Ala Ala Asn Asn Ala
    130                 135                 140

Phe Glu Ser Val Gln Lys Ala Val Lys Gln Ala Ser Asp Val Ala Glu
145                 150                 155                 160

Ala Asn Phe Asn Ala Val Ser Thr Gln Ala Val Ala Ala Lys Thr
                165                 170                 175

Ala Thr Thr Ser Arg Lys Arg
            180

<210> SEQ ID NO 71
<211> LENGTH: 182
<212> TYPE: PRT
<213> ORGANISM: Artificial Sequence
<220> FEATURE:
<223> OTHER INFORMATION: Sequence derived from Acidovorax delafieldii
      2AN

<400> SEQUENCE: 71

Met Thr Leu Thr Ala Glu Gln Ile Leu Ala Ser His Lys Ala Asn Ile
1               5                   10                  15

Glu Thr Leu Phe Gly Leu Thr Asn Lys Ala Phe Glu Gly Val Glu Lys
            20                  25                  30

Leu Val Glu Leu Asn Val Thr Ala Ser Arg Ala Ala Leu Ala Glu Ala
            35                  40                  45

Ala Asn His Thr Gln Ala Leu Leu Gly Val Lys Asp Ala Gln Glu Leu
    50                  55                  60

Leu Ala Leu Gln Ala Gly Leu Phe Gln Pro Leu Ala Glu Lys Thr Ala
65                  70                  75                  80

Ala Tyr Ser Arg His Leu Tyr Asp Ile Ala Ser Gly Thr Gly Ala Glu
                85                  90                  95

Phe Thr Arg Ala Phe Glu Val Gln Ala Thr Asp Ala Gln Arg Ser Phe
            100                 105                 110

Thr Asn Leu Val Asp Ser Ala Ala Lys Asn Ala Pro Ala Gly Ser Glu
            115                 120                 125

Thr Ala Val Ala Val Met Lys Ser Ala Val Ser Ala Asn Asn Ala
    130                 135                 140

Phe Glu Ser Val Gln Lys Ala Val Lys Gln Ala Ser Asp Val Ala Glu
145                 150                 155                 160

Ala Asn Phe Asn Ala Val Ala Ser Thr Ala Ala Asn Ala Ala Lys Thr
                165                 170                 175
```

Ala Ala Pro Arg Lys Arg
            180

<210> SEQ ID NO 72
<211> LENGTH: 181
<212> TYPE: PRT
<213> ORGANISM: Artificial Sequence
<220> FEATURE:
<223> OTHER INFORMATION: Sequence derived from Methylibium
      petroleiphilum PM1

<400> SEQUENCE: 72

Met Leu Thr Ala Glu Gln Ile Ile Ala His Lys Ala Asn Leu Glu
1               5                   10                  15

Thr Leu Phe Gly Leu Thr Asn Lys Ala Phe Glu Gly Val Glu Lys Leu
                20                  25                  30

Val Glu Leu Asn Leu Gln Val Ala Lys Ser Gly Leu Gly Glu Val Ala
                35                  40                  45

Glu His Ala Lys Ala Thr Leu Ser Ala Lys Asp Ala Gln Glu Leu Leu
            50                  55                  60

Ala Leu Gln Ala Asn Leu Leu Gln Pro Ala Ala Glu Lys Ala Ala Ala
65                  70                  75                  80

Tyr Ser Arg His Leu Tyr Asp Ile Ala Ser Gly Thr Asn Ala Glu Val
                85                  90                  95

Ser Lys Ile Ala Glu Gly Lys Ile Ser Glu Ala Gln Lys Ser Phe Leu
                100                 105                 110

Ala Val Val Asp Thr Ala Ile Lys Asn Ala Pro Ala Gly Thr Glu Asn
            115                 120                 125

Ala Ala Ala Leu Val Lys Ser Ala Val Ala Ala Asn Asn Ala Leu
            130                 135                 140

Glu Ser Val Thr Lys Ala Ala Lys Gln Ala Gln Asp Val Ala Glu Ala
145                 150                 155                 160

Asn Phe Gln Ala Leu Asn Thr Asn Ala Val Lys Ala Thr Ala Ala Ala
                165                 170                 175

Thr Lys Ala Arg Arg
            180

<210> SEQ ID NO 73
<211> LENGTH: 187
<212> TYPE: PRT
<213> ORGANISM: Artificial Sequence
<220> FEATURE:
<223> OTHER INFORMATION: Sequence derived from Leptothrix cholodnii SP-6

<400> SEQUENCE: 73

Met Ser Asn Ser Pro Glu Gln Phe Ala Ala Gly Lys Ala Asn Leu
1               5                   10                  15

Glu Ala Leu Val Glu Leu Gly Gln Lys Thr Phe Glu Gly Val Glu Lys
                20                  25                  30

Leu Val Glu Leu Asn Leu Gln Ala Ala Arg Ser Asn Met Gly Glu Gly
                35                  40                  45

Val Asp Ala Ala Lys Ala Leu Phe Ala Val Lys Asp Ala Gln Glu Leu
            50                  55                  60

Phe Ala Leu Gln Ser Ser Leu Met Gln Pro Ala Thr Glu Lys Ala Thr
65                  70                  75                  80

Ala Tyr Gly Arg Gln Val Tyr Glu Ile Ala Gln Ser Thr Gln Ala Glu
                85                  90                  95

```
Val Ala Lys Leu Ala Glu Ala Gln Tyr Ala Ala Leu Gln Gln Asn Ile
                100                 105                 110

Ala Ala Leu Val Asp Thr Ala Val Lys Asn Ala Pro Ala Gly Ser Glu
            115                 120                 125

Gly Ala Val Ala Met Val Arg Gln Ala Val Thr Ala Ala Asn Thr Ala
        130                 135                 140

Leu Glu Asn Ala Gln Lys Ala Ala Lys Gln Ala Val Gly Val Ala Glu
145                 150                 155                 160

Ala Asn Phe Glu Ala Met Ser Gln Thr Ala Ala Lys Ala Ala Ser Ala
                165                 170                 175

Val Ala Pro Lys Ala Ala Arg Arg Ala Ala Ala
            180                 185

<210> SEQ ID NO 74
<211> LENGTH: 183
<212> TYPE: PRT
<213> ORGANISM: Artificial Sequence
<220> FEATURE:
<223> OTHER INFORMATION: Sequence derived from Cupriavidus taiwanensis

<400> SEQUENCE: 74

Met Ser Pro Phe Thr Pro Glu Gln Phe Ala Ala Ala Gln Lys Ser Asn
1               5                   10                  15

Val Ser His Leu Phe Ala Leu Thr Asn Thr Ala Phe Glu Gly Phe Gln
            20                  25                  30

Lys Leu Thr Glu Leu Asn Leu Gln Thr Leu Lys Ala Thr Leu Ser Glu
        35                  40                  45

Gly Gln Glu Asn Val Gln Ala Ala Leu Ala Gly Lys Asp Leu Arg Glu
    50                  55                  60

Val Phe Ala Ala Gln Gly Asn Leu Ala Gln Pro Ala Ala Glu Lys Ala
65                  70                  75                  80

Val Ala Tyr Ala Arg His Val Tyr Glu Ile Ala Ser Asn Thr Gln Ala
                85                  90                  95

Glu Leu Ser Lys Ala Val Glu Ala Gln Tyr Glu Gln His Asn Arg Asn
                100                 105                 110

Val Gln Ala Phe Val Asp Thr Phe Val Lys Asn Ala Pro Ala Gly Ser
            115                 120                 125

Glu Ala Leu Thr Ala Leu Leu Gln Ser Gly Val Ala Ala Ala Ser Thr
        130                 135                 140

Thr Tyr Gln Ser Phe Gln Asp Ala Ala Lys Gln Thr Ala Glu Val Ala
145                 150                 155                 160

Lys Ala Asn Phe Ala Lys Thr Ala Ala Ser Ala Thr Ala Ala Asn Ala
                165                 170                 175

Thr Pro Arg Ala Ala Lys Ala
            180

<210> SEQ ID NO 75
<211> LENGTH: 185
<212> TYPE: PRT
<213> ORGANISM: Artificial Sequence
<220> FEATURE:
<223> OTHER INFORMATION: Sequence derived from Ralstonia eutropha H16

<400> SEQUENCE: 75

Met Ser Pro Phe Met Pro Glu Gln Phe Ala Ala Val Gln Lys Ser Ser
1               5                   10                  15

Leu Asn Gln Leu Phe Ala Leu Thr Asn Met Ala Phe Asp Gly Phe Gln
            20                  25                  30
```

```
Lys Leu Thr Glu Leu Asn Leu Gln Ala Val Arg Thr Thr Leu Ala Glu
            35                  40                  45

Gly Gln Gly Asn Ile Glu Ala Val Leu Ala Gly Lys Asp Leu Arg Glu
 50                  55                  60

Val Phe Ala Val Gln Gly Asn Leu Ala Gln Pro Ala Ala Glu Lys Ala
 65                  70                  75                  80

Val Ala Tyr Ala Arg His Val Tyr Glu Ile Ala Ser Asn Thr Gln Val
                 85                  90                  95

Glu Leu Thr Lys Ala Val Glu Gly Gln Tyr Glu Gln His Asn Arg Asn
            100                 105                 110

Val Gln Ala Phe Val Asp Asn Phe Val Lys Asn Ala Pro Ala Gly Ser
            115                 120                 125

Glu Ala Ile Thr Ala Leu Leu Gln Ser Ser Val Ala Ala Ala Ser Ser
130                 135                 140

Thr Phe Gln Ser Phe Gln Asp Ala Ala Lys Gln Thr Ala Glu Val Ala
145                 150                 155                 160

Lys Ala Asn Phe Ala Lys Thr Ala Ala Ala Ser Gly Ala Ala Gln
                165                 170                 175

Gln Ala Ala Pro Arg Ala Ser Lys Gln
            180                 185

<210> SEQ ID NO 76
<211> LENGTH: 181
<212> TYPE: PRT
<213> ORGANISM: Artificial Sequence
<220> FEATURE:
<223> OTHER INFORMATION: Sequence derived from Ralstonia eutropha H16

<400> SEQUENCE: 76

Met Pro Glu Gln Phe Ala Ala Val Gln Lys Ser Ser Leu Asn Gln Leu
 1               5                  10                  15

Phe Ala Leu Thr Asn Met Ala Phe Asp Gly Phe Gln Lys Leu Thr Glu
             20                  25                  30

Leu Asn Leu Gln Ala Val Arg Thr Thr Leu Ala Glu Gly Gln Gly Asn
         35                  40                  45

Ile Glu Ala Val Leu Ala Gly Lys Asp Leu Arg Glu Val Phe Ala Val
 50                  55                  60

Gln Gly Asn Leu Ala Gln Pro Ala Ala Glu Lys Ala Val Ala Tyr Ala
 65                  70                  75                  80

Arg His Val Tyr Glu Ile Ala Ser Asn Thr Gln Val Glu Leu Thr Lys
                 85                  90                  95

Ala Val Glu Gly Gln Tyr Glu Gln His Asn Arg Asn Val Gln Ala Phe
            100                 105                 110

Val Asp Asn Phe Val Lys Asn Ala Pro Ala Gly Ser Glu Ala Ile Thr
            115                 120                 125

Ala Leu Leu Gln Ser Ser Val Ala Ala Ala Ser Ser Thr Phe Gln Ser
130                 135                 140

Phe Gln Asp Ala Ala Lys Gln Thr Ala Glu Val Ala Lys Ala Asn Phe
145                 150                 155                 160

Ala Lys Thr Ala Ala Ala Ser Gly Ala Ala Gln Gln Ala Ala Pro
                165                 170                 175

Arg Ala Ser Lys Gln
            180

<210> SEQ ID NO 77
```

<211> LENGTH: 188
<212> TYPE: PRT
<213> ORGANISM: Artificial Sequence
<220> FEATURE:
<223> OTHER INFORMATION: Sequence derived from Janthinobacterium sp. Marseille

<400> SEQUENCE: 77

```
Met Phe Thr Ile Pro Glu Gln Phe Ser Ala Ala Thr Lys His Gln Phe
1               5                   10                  15

Glu Ser Gln Leu Ala Ile Leu Asn Ser Leu Thr Ser Thr Ala Phe Asp
            20                  25                  30

Ser Val Gln Lys Ile Val Asp Leu Asn Leu Asn Ala Ala Lys Ser Ser
        35                  40                  45

Leu Gln Glu Ser Ser Ala Ala Ala Gln Lys Leu Ala Thr Ala Lys Asp
    50                  55                  60

Pro Gln Glu Phe Phe Ser Leu Ser Ala Ala His Ala Gln Pro Asn Ala
65                  70                  75                  80

Glu Lys Ala Leu Ala Tyr Gly Arg His Leu Ala Ser Ile Ala Ser Ser
                85                  90                  95

Thr Gln Ala Glu Phe Thr Lys Ala Ala Glu Thr Gln Ile Ala Glu Thr
            100                 105                 110

Asn Arg Lys Val Leu Ser Leu Ile Asp Glu Leu Ser Lys Asn Ala Pro
        115                 120                 125

Ala Gly Ser Glu Asn Ala Ile Ser Ile Leu Lys Ser Ala Ile Gly Asn
    130                 135                 140

Ala Asn Ala Gly Tyr Glu Gln Leu Ser Lys Thr Thr Lys Gln Ala Val
145                 150                 155                 160

Glu Ala Leu Glu Gly Asn Leu Asn Ala Ala Ala Asn Gln Phe Val Ser
                165                 170                 175

Ala Ala Glu Lys Thr Thr Thr Arg Ser Arg Lys Ser
            180                 185
```

<210> SEQ ID NO 78
<211> LENGTH: 192
<212> TYPE: PRT
<213> ORGANISM: Artificial Sequence
<220> FEATURE:
<223> OTHER INFORMATION: Sequence derived from Bordetella avium 197N

<400> SEQUENCE: 78

```
Met Thr Ala Ile Pro Gln Gln Val Leu Ala Arg Gln Lys Ser Ala Leu
1               5                   10                  15

Gln Thr Leu Val Ala Ala Gln Thr Ala Val Phe Gly Gly Phe Glu Lys
            20                  25                  30

Leu Val Asp Leu Asn Leu Lys Val Val Lys Ala Thr Leu Asp Glu Val
        35                  40                  45

Ala Gln Lys Ser Gln Gln Ala Val Glu Leu Lys Asp Val Gln Asp Ala
    50                  55                  60

Ala Ser Phe Thr Ser Ala Leu Val Gln Pro Ser Ala Glu Lys Ala Leu
65                  70                  75                  80

Ala Tyr Gly Lys His Val Tyr Asp Ile Ile Asn Thr Val Gln Ala Asp
                85                  90                  95

Leu Ala Lys Leu Ala Glu Ala Gln Ile Ala Glu Gly Gln Gln His Val
            100                 105                 110

Gln Glu Ala Val Glu Gln Phe Ser Lys Asn Ala Pro Asn Gly Ser Glu
        115                 120                 125
```

Ser Ala Val Ala Leu Leu Lys Ser Ser Leu Ala Thr Ala Asn Asn Ala
        130                 135                 140

Tyr Glu Ser Leu Thr Lys Ala Ala Lys Gln Ala Ala Glu Val Ala Glu
145                 150                 155                 160

Ser Asn Leu Asn Ala Ala Ala Ser Ala Thr Phe Lys Ala Ala Ser Asp
                165                 170                 175

Ala Ala Asp Val Ala Thr Lys Ala Ala Gly Arg Thr Arg Arg Ala Thr
            180                 185                 190

<210> SEQ ID NO 79
<211> LENGTH: 188
<212> TYPE: PRT
<213> ORGANISM: Artificial Sequence
<220> FEATURE:
<223> OTHER INFORMATION: Sequence derived from uncultured bacterium
      pEAF66

<400> SEQUENCE: 79

Met Phe Ala Ile Pro Glu Gln Phe Ser Asn Ala Thr Lys Ala Asn Phe
1               5                   10                  15

Glu Ser Gln Phe Ala Ile Phe Ser Ser Leu Thr Ser Lys Ala Phe Glu
                20                  25                  30

Gly Met Glu Lys Leu Val Glu Leu Asn Leu Thr Ala Ala Lys Ala Ser
            35                  40                  45

Leu Glu Glu Ser Ser Ile Thr Thr Arg Gln Leu Leu Ser Ala Lys Asp
50                  55                  60

Pro Gln Glu Phe Phe Ser Leu Thr Ala Ala Gln Ala Gln Pro Thr Ala
65                  70                  75                  80

Glu Lys Ala Met Ser Tyr Ser Arg Gln Val Ala Ala Ile Ala Ala Gly
                85                  90                  95

Thr Gln Ala Glu Phe Thr Lys Ala Ala Glu Glu Gln Ile Ala Glu Thr
            100                 105                 110

Asn Arg Lys Val Ile Ser Leu Val Asp Glu Val Thr Lys Asn Ala Pro
        115                 120                 125

Ala Gly Ser Glu Asn Val Val Ser Ile Ile Lys Ala Thr Ile Gly Asn
130                 135                 140

Ala Asn Ala Gly Tyr Glu Gln Phe Ser Lys Thr Ala Lys Gln Ala Ala
145                 150                 155                 160

Glu Thr Ile Glu Ala Asn Val Gly Ala Ala Val Asn Gln Phe Thr Gln
                165                 170                 175

Ala Ala Gln Asn Ala Val Pro Lys Ala Gly Lys Lys
            180                 185

<210> SEQ ID NO 80
<211> LENGTH: 181
<212> TYPE: PRT
<213> ORGANISM: Artificial Sequence
<220> FEATURE:
<223> OTHER INFORMATION: Sequence derived from Polaromonas
      naphthalenivorans CJ2

<400> SEQUENCE: 80

Met Asn Asn Ala Ala Glu Gln Phe Ile Ala Thr Asn Lys Ala Asn Leu
1               5                   10                  15

Gln Ser Leu Thr Asp Leu Thr Thr Gln Ala Phe Ala Gly Val Glu Lys
                20                  25                  30

Leu Val Glu Leu Asn Met Ala Ala Ser Lys Ala Ala Leu Ser Glu Ser
            35                  40                  45

-continued

```
Phe Thr His Val Gln Thr Val Met Ala Ile Lys Asp Pro Lys Glu Leu
    50                  55                  60

Met Ala Leu Gln Ser Gly Leu Leu Lys Pro Met Ala Asp Lys Thr Ala
65                  70                  75                  80

Ala Tyr Ala Gln His Leu Gln Thr Ile Val Thr Asp Ser Gly Ala Glu
                85                  90                  95

Phe Thr Lys Ala Val Glu Ala Lys Thr Ala Glu Ala Gln Lys Ala Phe
            100                 105                 110

Gly Asp Val Leu Glu Asn Leu Thr Lys Asn Ala Pro Ala Gly Ser Glu
        115                 120                 125

Thr Ile Val Thr Ala Phe Lys Asp Ala Leu Ser Ser Gly Gln Asn Ala
    130                 135                 140

Ile Glu Ser Val Gln Thr Gln Thr Lys Lys Ala Val Glu Thr Ala Gln
145                 150                 155                 160

Ser Asn Phe Thr Ala Ala Ala Thr Gln Ala Ser Asp Ala Val Lys Lys
                165                 170                 175

Val Thr Lys Ser Ala
            180

<210> SEQ ID NO 81
<211> LENGTH: 188
<212> TYPE: PRT
<213> ORGANISM: Artificial Sequence
<220> FEATURE:
<223> OTHER INFORMATION: Sequence derived from Burkholderia
      phytofirmans PsJN

<400> SEQUENCE: 81

Met Ala Leu Ser Ser Pro Asp Pro Ala Ala Val Val Lys Ala Asn Leu
1               5                   10                  15

Asp Ala Phe Phe Gly Leu Thr Gly Lys Ile Phe Glu Gly Ala Glu Lys
            20                  25                  30

Leu Ala Ala Leu Asn Leu Gln Ala Val Arg Ser Thr Leu Ala Glu Ala
        35                  40                  45

Gln Glu Asn Met Thr Lys Ala Pro Gly Thr Thr Asp Pro Leu Gln Trp
    50                  55                  60

Phe Ala Leu Gln Ser Gly Leu Thr Gly Pro Phe Ala Glu Asn Ser Leu
65                  70                  75                  80

Ser Tyr Gly Arg Gln Val Phe Asp Ile Ala Ser Thr Thr Gln Ala Glu
                85                  90                  95

Leu Thr Gln Phe Ala Gln Ala Gln Tyr Glu Arg His Asn Ala Arg Val
            100                 105                 110

Gln Ala Phe Val Glu Glu Ala Lys Asn Ala Pro Ala Gly Ser Glu
        115                 120                 125

Ala Ala Ile Ala Ala Trp Lys Ser Ala Thr Ser Ala Thr Ser Thr Leu
    130                 135                 140

Tyr Glu Thr Leu Gln Lys Thr Gly Gln Gln Ala Val Gln Ala Ala Glu
145                 150                 155                 160

Ser Asn Phe Asn Ser Val Ala Ala Thr Ala Ser Lys Thr Ala Arg Arg
                165                 170                 175

Ala Glu Gln Ala Pro Val Ala Ala Gly Thr Lys Gly
            180                 185

<210> SEQ ID NO 82
<211> LENGTH: 189
<212> TYPE: PRT
<213> ORGANISM: Artificial Sequence
```

```
<220> FEATURE:
<223> OTHER INFORMATION: Sequence derived from Herminiimonas
      arsenicoxydans

<400> SEQUENCE: 82

Met Phe Ala Ile Pro Glu Gln Phe Ser Thr Ala Thr Lys Asn Gln Phe
1               5                   10                  15

Glu Ala Gln Leu Ala Ile Leu Asn Ser Phe Ala Ser Thr Ala Phe Asp
            20                  25                  30

Ser Val Gln Lys Ile Val Asp Leu Asn Leu Asn Val Lys Ser Ser
        35                  40                  45

Leu Gln Glu Ser Ser Ala Ala Ala Gln Gln Leu Ile Ser Ala Lys Asp
50                  55                  60

Pro Gln Glu Phe Phe Ser Leu Ser Ala Ala Gln Ala Gln Pro Thr Ala
65                  70                  75                  80

Glu Lys Ala Leu Ala Tyr Ser Arg His Leu Val Gly Ile Thr Thr Ser
                85                  90                  95

Thr Gln Ala Glu Phe Ala Lys Ala Ala Glu Thr Gln Ile Ala Glu Thr
            100                 105                 110

Asn Arg Lys Val Leu Ser Leu Val Glu Glu Leu Ser Lys Asn Ala Pro
        115                 120                 125

Ala Gly Ser Glu Asn Ala Ile Ala Leu Ile Lys Ser Ala Ile Gly Asn
130                 135                 140

Ala Asn Ala Gly Tyr Glu Gln Leu Ser Lys Thr Thr Lys His Ala Val
145                 150                 155                 160

Glu Thr Leu Glu Gly Asn Leu Asn Ala Ala Ser Gln Phe Ala Ser
                165                 170                 175

Ala Ala Glu Lys Thr Thr Ala Arg Ala Arg Lys Ala Ala
            180                 185

<210> SEQ ID NO 83
<211> LENGTH: 181
<212> TYPE: PRT
<213> ORGANISM: Artificial Sequence
<220> FEATURE:
<223> OTHER INFORMATION: Sequence derived from Polaromonas sp. JS666

<400> SEQUENCE: 83

Met Thr Tyr Thr Ala Glu Gln Leu Ile Ala Thr Thr Gln Ser Asn Val
1               5                   10                  15

Asp Ala Leu Glu Gly Leu Ala Thr Gln Ala Phe Ala Gly Phe Glu Lys
            20                  25                  30

Leu Val Glu Leu Asn Leu Ser Ala Ser Lys Ala Ala Leu Ala Glu Ser
        35                  40                  45

Phe Ser Asn Ala Arg Ala Leu Ala Gly Ala Lys Asp Pro Gln Gln Leu
50                  55                  60

Leu Ala Leu Gln Ala Gly Leu Phe Gln Pro Leu Ala Glu Lys Ser Val
65                  70                  75                  80

Ser Tyr Gly Asn Gln Val Tyr Ser Val Ala Ala Glu Thr Gly Ala Val
                85                  90                  95

Phe Thr Lys Thr Phe Glu Ala Lys Val Asp Glu Ala Lys Lys Ala Phe
            100                 105                 110

Ala Val Ala Val Asp Asn Met Thr Lys Asn Ala Pro Ala Gly Thr Glu
        115                 120                 125

Ala Ala Val Ala Ala Phe Lys Ser Ala Val Ser Ala Ser Gln Asn Ala
130                 135                 140
```

```
Ile Glu Thr Ala Gln Gly Thr Ala Lys Lys Ala Val Glu Leu Ala Glu
145                 150                 155                 160

Ser Asn Phe Thr Ala Val Thr Lys Gln Ala Val Ser Ala Thr Thr
                165                 170                 175

Ser Ser Lys Lys Arg
            180
```

<210> SEQ ID NO 84
<211> LENGTH: 185
<212> TYPE: PRT
<213> ORGANISM: Artificial Sequence
<220> FEATURE:
<223> OTHER INFORMATION: Sequence derived from Ralstonia eutropha JMP134

<400> SEQUENCE: 84

```
Met Phe Pro Ser Thr Pro Asp Gln Val Val Ala Ala Gln Glu Ser Ser
1               5                   10                  15

Val Gly Tyr Trp Phe Thr Leu Thr Asn Ile Ala Val Glu Gly Leu Gln
            20                  25                  30

Arg Leu Thr Glu Leu Asn Leu Gln Thr Ala Arg Thr Thr Val Ala Asp
        35                  40                  45

Ser Gln Asp Asn Val Arg Ala Leu Phe Ala Gly Arg Asp Leu Arg Asp
    50                  55                  60

Val Phe Ala Val Gln Ala Asn Leu Ala Gln Pro Ala Ala Glu Lys Ala
65                  70                  75                  80

Ile Ala Tyr Ala Arg Asn Val Tyr Glu Ile Ala Ser Asn Thr Gln Ala
                85                  90                  95

Glu Leu Thr Lys Ala Val Glu Ala Arg Tyr Glu Gln His Ser Arg Asn
            100                 105                 110

Met Gln Ser Phe Val Asp Thr Phe Val Lys Asn Ala Pro Ala Gly Ser
        115                 120                 125

Glu Ala Ile Thr Ala Leu Leu Gln Ser Ser Val Ala Ala Ala Ser Ser
    130                 135                 140

Thr Tyr Gln Ser Ile Gln Ser Ala Ala Lys Gln Thr Ala Glu Ala Ala
145                 150                 155                 160

Gly Ala Arg Phe Val Thr Thr Ala Leu Ala Ala Ser Gly Ala Ala Gln
                165                 170                 175

Gln Ala Gly Ala Arg Ala Pro Arg Gln
            180                 185
```

<210> SEQ ID NO 85
<211> LENGTH: 174
<212> TYPE: PRT
<213> ORGANISM: Artificial Sequence
<220> FEATURE:
<223> OTHER INFORMATION: Sequence derived from Polaromonas
      naphthalenivorans CJ2

<400> SEQUENCE: 85

```
Met Asn Tyr Ser Asn Asp Gln Leu Ile Ala Thr Gln Lys Ser Ser Val
1               5                   10                  15

Glu Ala Leu Ala Gly Leu Ser Glu Lys Ala Phe Ala Ser Phe Glu Lys
            20                  25                  30

Leu Val Glu Leu Asn Met Ala Ala Ser Lys Ala Leu Leu Gly Glu Ser
        35                  40                  45

Ile Ser His Leu Gln Ala Leu Ser Glu Ile Lys Asp Pro Lys Glu Leu
    50                  55                  60

Leu Ser Leu Gln Ser Glu Leu Val Lys Pro Met Ala Glu Lys Ala Ala
```

```
                    65                  70                  75                  80
Ser Tyr Ser Arg His Leu Tyr Glu Ile Leu Ser Gly Ala Ser Ala Glu
                85                  90                  95

Phe Thr Lys Thr Leu Glu Ser Thr Ser Ala Glu Ser Gln Lys Thr Val
            100                 105                 110

Thr Glu Leu Leu Glu Thr Ser Leu Lys Asn Ala Pro Ala Gly Ser Glu
            115                 120                 125

Ala Ala Val Ala Val Ile Lys Ser Ala Ile Thr Ala Gly Asn Thr Ala
        130                 135                 140

Val Glu Thr Ala Gln Lys Ser Ala Lys Gln Ala Ala Gln Leu Val Glu
145                 150                 155                 160

Ser Asn Ile Thr Ala Leu Ser Ser Ala Ala Thr Lys Ala Glu
                165                 170

<210> SEQ ID NO 86
<211> LENGTH: 164
<212> TYPE: PRT
<213> ORGANISM: Artificial Sequence
<220> FEATURE:
<223> OTHER INFORMATION: Sequence derived from Burkholderia phytofirmans
      PsJN

<400> SEQUENCE: 86

Met Ser Thr Leu Ile Pro Gln Gln Leu Val Ala Ala Gln Gln Ser Ser
1               5                   10                  15

Leu Glu Ala Leu Phe Gly Leu Thr Asn Lys Ala Phe Glu Gly Phe Glu
            20                  25                  30

Gln Leu Val Ala Leu Asn Leu Gln Val Gly Lys Ala Val Leu Ala Glu
        35                  40                  45

Asn Gln Glu Ile Val Thr Lys Ala Leu Ser Ala Gly Asn Pro Gly Ala
    50                  55                  60

Leu Phe Ala Leu Gln Ala Ser Leu Ser Gln Pro Val Ala Glu Lys Val
65                  70                  75                  80

Val Ala Tyr Gly Arg Arg Val His Glu Ile Val Ser Gly Val Gln Ser
                85                  90                  95

Glu Ile Thr Ala Ala Ala Thr Ala Gln Gly Gln Gln Phe Gln Arg Asp
            100                 105                 110

Ala Gln Gly Phe Val Glu Ser Leu Gln Lys Asn Thr Pro Ala Gly Ser
        115                 120                 125

Glu Ser Ala Val Ala Ala Trp Asn Ser Val Leu Ser Ala Ala Asn Ala
    130                 135                 140

Thr Tyr Glu Ser Ala Asn Lys Ala Ala Lys Gln Phe Val Ser Ser Val
145                 150                 155                 160

Ser Ala Val His

<210> SEQ ID NO 87
<211> LENGTH: 191
<212> TYPE: PRT
<213> ORGANISM: Artificial Sequence
<220> FEATURE:
<223> OTHER INFORMATION: Sequence derived from Bordetella petrii DSM
      12804

<400> SEQUENCE: 87

Met Thr Ala Ile Pro Gln Gln Val Leu Asp Arg Gln Lys Ser Ala Leu
1               5                   10                  15

Asn Thr Leu Ala Ala Thr Gln Ala Thr Leu Phe Ala Gly Phe Glu Lys
            20                  25                  30
```

```
Leu Val Asp Leu Asn Leu Lys Val Lys Ala Thr Leu Asp Glu Val
            35                  40                  45

Ala Gln Thr Ser Gln Gln Ala Ile Ala Val Lys Asp Pro Gln Glu Ala
    50                  55                  60

Ala Ala Phe Ala Thr Ala Leu Val Gln Pro Gly Ala Glu Lys Ala Leu
65                  70                  75                  80

Ala Tyr Gly Lys His Val Tyr Asp Ile Val Ala Gly Val Gln Gly Glu
                85                  90                  95

Leu Ala Lys Leu Ala Glu Ala Gln Ile Ala Glu Gly Gln Gln Gln Val
            100                 105                 110

Ala Asp Ala Val Glu Gln Phe Ser Lys Ser Ala Pro Thr Gly Ser Glu
            115                 120                 125

Ser Ala Val Ala Leu Leu Lys Ser Ser Leu Ala Thr Ala Asn Gly Ala
    130                 135                 140

Tyr Glu Ser Leu Thr Lys Ala Ala Lys Gln Ala Ala Glu Val Ala Glu
145                 150                 155                 160

Ser Asn Leu Asn Ala Ala Asn Ala Thr Phe Lys Ala Ala Thr Asp
                165                 170                 175

Ala Ala Glu Ala Ala Thr Lys Ala Pro Arg Ser Arg Arg Ala Ala
            180                 185                 190

<210> SEQ ID NO 88
<211> LENGTH: 189
<212> TYPE: PRT
<213> ORGANISM: Artificial Sequence
<220> FEATURE:
<223> OTHER INFORMATION: Sequence derived from Ralstonia eutropha H16

<400> SEQUENCE: 88

Met Thr Gln Trp Ser Pro Glu Gln Phe Ile Lys Val Gln Met Ala Gly
1               5                   10                  15

Ile Glu Ala Leu Thr Gly Leu Thr Gly Lys Ala Phe Glu Gly Phe Glu
            20                  25                  30

Lys Leu Leu Glu Leu Asn Leu Gln Ala Met Lys Thr Ala Leu Ala Asp
            35                  40                  45

Ser Arg Glu Gly Ala Arg Lys Ala Leu Ser Ala Lys Asp Pro Gln Glu
    50                  55                  60

Leu Val Glu Leu Gln Ile Ala Leu Phe Gln Pro Ala Ala Asp Asn Val
65                  70                  75                  80

Leu Ala Tyr Arg Arg Gln Leu Tyr Asp Ile Leu Ala Ala Thr Arg Ala
                85                  90                  95

Glu Phe Glu Lys Val Ala Glu Val Gln Tyr Thr Ala Gly Lys Gln Gly
            100                 105                 110

Leu His Asp Phe Leu Gly Ser Val Ser Gln Thr Pro Ser Gly Ala
            115                 120                 125

Ala Ala Ala Pro Leu Ala Ala Trp Gln Glu Ala Val Ser Ala Thr Thr
    130                 135                 140

Thr Leu Tyr Glu Ser Met Gln Thr Thr Ala Lys Gln Ala Val Gln Ala
145                 150                 155                 160

Ala Glu Ser Ser Phe Asn Thr Ala Ala Gln Val Ala Ser Lys Gly Met
                165                 170                 175

Gln Arg Arg Ala Ala Gln Ala Ser Lys Ala Ala Ala Asn
            180                 185

<210> SEQ ID NO 89
```

<211> LENGTH: 164
<212> TYPE: PRT
<213> ORGANISM: Artificial Sequence
<220> FEATURE:
<223> OTHER INFORMATION: Sequence derived from Burkholderia graminis C4D1M

<400> SEQUENCE: 89

Met Ser Thr Leu Ile Pro Gln Gln Leu Val Thr Ala Gln Gln Ser Ser
1 5 10 15

Leu Glu Thr Leu Phe Gly Leu Thr Ser Lys Val Phe Glu Gly Phe Glu
20 25 30

Lys Leu Val Ala Leu Asn Leu Gln Val Ser Lys Ala Ala Ile Val Gln
35 40 45

Asn His Glu Asn Val Thr Lys Ala Met Ser Gly Gly Asn Pro Gly Glu
50 55 60

Leu Leu Ala Arg Gln Ala Ser Leu Ser Gln Pro Ala Ala Glu Lys Ala
65 70 75 80

Val Ala Tyr Gly Arg Gln Val His Glu Ile Leu Val Gly Val Gln Ser
85 90 95

Glu Ile Ser Ala Ala Ala Thr Ala Gln Gly Gln Gln Phe Gln Arg Glu
100 105 110

Ala Gln Gly Phe Val Glu Asn Leu Thr Lys Asn Ala Pro Ala Gly Ser
115 120 125

Glu Ser Ala Ile Ala Ala Trp Ser Ser Ala Phe Ser Thr Ala Ser Thr
130 135 140

Val Tyr Glu Ser Ala Asn Lys Ala Ala Lys Gln Phe Val Ser Lys Val
145 150 155 160

Ser Thr Val Gln

<210> SEQ ID NO 90
<211> LENGTH: 192
<212> TYPE: PRT
<213> ORGANISM: Artificial Sequence
<220> FEATURE:
<223> OTHER INFORMATION: Sequence derived from Bordetella pertussis Tohama I

<400> SEQUENCE: 90

Met Ser Ala Ile Pro Gln Gln Val Leu Ala Arg Gln Lys Ala Thr Val
1 5 10 15

Asn Ser Leu Val Ala Ala Gln Ser Ala Met Phe Ala Gly Phe Glu Lys
20 25 30

Leu Val Asp Leu Asn Leu Lys Val Val Arg Ala Thr Leu Asp Glu Val
35 40 45

Ala Gln Gln Ser Gln Gln Ala Ala Glu Leu Lys Asp Pro Gln Asp Val
50 55 60

Ala Ser Phe Thr Ser Gly Leu Val Gln Pro Gly Ala Glu Lys Ala Leu
65 70 75 80

Ala Tyr Gly Lys His Val Tyr Asp Ile Val Ala Gly Val Gln Ala Glu
85 90 95

Leu Ala Gln Leu Ala Glu Ala Gln Ile Ala Glu Gly Gln Gln Gln Leu
100 105 110

Thr Glu Ala Val Glu Gln Phe Ser Lys Asn Ala Pro Thr Gly Ser Glu
115 120 125

Ser Ala Val Ala Leu Ile Lys Ser Ser Leu Ala Thr Ala Asn Ser Ala
130 135 140

Tyr Asp Ser Leu Thr Lys Ala Ala Lys Gln Ala Ala Glu Val Ala Glu
145                 150                 155                 160

Ser Asn Leu Asn Ala Ala Asn Ala Ser Phe Lys Ala Ala Ser Asp
            165                 170                 175

Ala Ala Glu Val Ala Thr Lys Ala Ala Gly Arg Asn Arg Ala Ala
        180                 185                 190

<210> SEQ ID NO 91
<211> LENGTH: 189
<212> TYPE: PRT
<213> ORGANISM: Artificial Sequence
<220> FEATURE:
<223> OTHER INFORMATION: Sequence derived from Herbaspirillum
      seropedicae SmR1

<400> SEQUENCE: 91

Met Phe Ser Tyr Gln Asp Gln Phe Ser Ala Ala Thr Lys Ala Asn Leu
1               5                   10                  15

Gln Ala His Leu Asp Leu Ile Asn Ser Leu Thr Ala Lys Ala Phe Glu
            20                  25                  30

Gly Val Glu Lys Ile Val Glu Leu Asn Leu Ser Ala Thr Lys Ala Thr
        35                  40                  45

Leu Glu Glu Ala Ala Ala Ala Ala Lys Gln Leu Ala Gly Ala Lys Asp
50                  55                  60

Pro Gln Glu Leu Leu Ser Leu Ala Thr Ala Gln Ala Gln Pro Gly Ala
65                  70                  75                  80

Glu Lys Ala Thr Ala Tyr Gly Arg His Leu Ala Gly Ile Val Ser Ser
                85                  90                  95

Thr Gln Ala Glu Phe Thr Lys Ala Ala Glu Ala Gln Ile Ala Glu Thr
            100                 105                 110

Ser Arg Lys Leu Ser Ala Leu Ile Asp Glu Ile Thr Lys Asn Ala Pro
        115                 120                 125

Pro Gly Ser Glu Gln Ala Val Ser Ile Leu Lys Ala Thr Leu Thr Asn
    130                 135                 140

Ala Asn Ala Ala Tyr Glu Gln Leu Ser Lys Asn Ser Lys Gln Ala Val
145                 150                 155                 160

Glu Thr Leu Glu Ala Asn Leu Ala Asn Ala Thr Lys Gln Phe Thr Ala
                165                 170                 175

Ala Ala Glu Lys Thr Val Ala Ser Thr Arg Ala Lys Lys
            180                 185

<210> SEQ ID NO 92
<211> LENGTH: 192
<212> TYPE: PRT
<213> ORGANISM: Artificial Sequence
<220> FEATURE:
<223> OTHER INFORMATION: Sequence derived from Achromobacter piechaudii
      ATCC 43553

<400> SEQUENCE: 92

Met Ser Ala Ile Pro Gln Gln Val Leu Asp Arg Gln Lys Ala Ser Ile
1               5                   10                  15

Asn Thr Phe Val Ala Ala Gln Ser Ala Val Phe Ala Gly Phe Glu Lys
            20                  25                  30

Leu Val Glu Leu Asn Met Lys Val Val Arg Ala Thr Leu Asp Glu Val
        35                  40                  45

Ala Gln Lys Ser Gln Gln Ala Ser Glu Val Lys Asp Pro Gln Glu Ala
    50                  55                  60

```
Ala Ala Phe Ala Ser Gly Leu Leu Gln Pro Gly Ala Glu Lys Ala Met
65                  70                  75                  80

Ala Tyr Thr Lys His Val Tyr Asp Ile Val Ala Gly Val Gln Gly Ser
                85                  90                  95

Leu Val Lys Leu Thr Glu Glu Gln Ile Ala Glu Ser Gln Gln Gln Leu
            100                 105                 110

Ser Glu Ala Val Asp Gln Leu Ser Lys Asn Ala Pro Ala Gly Ser Glu
        115                 120                 125

Ser Ala Val Ala Leu Ile Lys Ser Ser Leu Ala Thr Ala Thr Ser Ala
    130                 135                 140

Tyr Asp Ser Val Thr Lys Ala Lys Gln Ala Ala Glu Val Ala Glu
145                 150                 155                 160

Ser Asn Leu Asn Ala Ala Ala Asn Ala Thr Phe Lys Ala Ala Thr Asp
                165                 170                 175

Ala Ala Asp Ala Ala Asn Lys Val Ala Ser Arg Ser Arg Arg Thr Ala
            180                 185                 190

<210> SEQ ID NO 93
<211> LENGTH: 183
<212> TYPE: PRT
<213> ORGANISM: Artificial Sequence
<220> FEATURE:
<223> OTHER INFORMATION: Sequence derived from Candidatus Accumulibacter
      phosphatis clade IIA str. UW-1

<400> SEQUENCE: 93

Met Phe Thr Thr Pro Glu Gln Phe Ala Ala Ala Asn Lys Ala Ser Val
1               5                   10                  15

Asp Ala Met Leu Thr Leu Ala Asn Thr Ala Leu Ala Ser Ala Glu Arg
            20                  25                  30

Ile Ala Ala Leu Asn Leu Asn Thr Ala Arg Ser Met Leu Glu Asp Gly
        35                  40                  45

Val Ala Asn Ala Lys Ala Met Leu Gly Ala Lys Asp Pro Gln Glu Phe
    50                  55                  60

Phe Ser Val Gln Ala Ser Leu Ala Gln Pro Ser Leu Glu Lys Ala Val
65                  70                  75                  80

Ala Tyr Thr Arg Ser Val Tyr Glu Ile Ser Ala Gln Ser Lys Glu Glu
                85                  90                  95

Ile Thr Lys Leu Leu Glu Ala Gln Phe Ser Asp Phe Gln Lys Gln Thr
            100                 105                 110

Leu Ala Leu Leu Glu Lys Ala Thr Lys Asn Ala Pro Val Gly Ser Asp
        115                 120                 125

Val Ala Val Ser Ala Val Lys Ser Ala Ile Ala Ser Ala Thr Ser Ala
    130                 135                 140

Phe Asp Ser Met Asn Lys Ala Ala Lys Gln Val Ala Asp Ile Ala Glu
145                 150                 155                 160

Ala Asn Val Ala Ala Ala Thr Asn Ala Thr Val Lys Ala Val Gly Ala
                165                 170                 175

Thr Ala Ala Asn Val Lys Lys
            180

<210> SEQ ID NO 94
<211> LENGTH: 181
<212> TYPE: PRT
<213> ORGANISM: Artificial Sequence
<220> FEATURE:
<223> OTHER INFORMATION: Sequence derived from Rhodoferax ferrireducens
      T118
```

<400> SEQUENCE: 94

| Met | Asn | Thr | Thr | Ala | Glu | Gln | Phe | Ile | Ala | Thr | Asn | Lys | Ala | Asn | Leu |
|---|---|---|---|---|---|---|---|---|---|---|---|---|---|---|---|
| 1 | | | | 5 | | | | | 10 | | | | | 15 | |

Gln Ala Leu Gln Gly Phe Thr Thr Gln Ala Phe Ala Gly Ile Glu Lys
          20                25                30

Leu Val Glu Leu Asn Leu Ala Ala Ser Lys Ala Ala Leu Gly Glu Ser
      35                40                45

Phe Asn His Val Gln Ala Ala Leu Gly Ala Lys Asp Ala Gln Gln Leu
      50                55                60

Leu Ala Leu Gln Ser Gly Leu Val Lys Pro Leu Thr Glu Lys Ser Ala
65              70                75              80

Ala Tyr Val Gln His Val Gln Thr Ile Val Thr Gly Ser Gly Ala Glu
              85                90              95

Phe Thr Lys Ala Val Glu Ala Lys Thr Ala Glu Ala Gln Lys Ala Phe
          100             105            110

Asp Ser Val Leu Glu Asn Leu Thr Lys Asn Ala Pro Ala Gly Ser Glu
         115            120            125

Thr Ala Val Ala Ala Phe Lys Asn Ala Leu Thr Ser Gly Gln Asn Ala
130             135               140

Leu Glu Ser Ala Gln Ala Gln Ala Lys Lys Ala Leu Ala Thr Ala Gln
145             150            155           160

Ala Asn Phe Thr Ala Ala Thr Gln Thr Ala Asp Ala Val Lys Lys
             165              170           175

Ala Thr Lys Val Ala
         180

<210> SEQ ID NO 95
<211> LENGTH: 186
<212> TYPE: PRT
<213> ORGANISM: Artificial Sequence
<220> FEATURE:
<223> OTHER INFORMATION: Sequence derived from Aromatoleum aromaticum
    EbN1

<400> SEQUENCE: 95

Met Phe Ala Thr Pro Glu Gln Phe Ala Thr Asn Lys Ala Asn Val
1             5                10              15

Glu Thr Leu Leu Thr Leu Ala Asn Asn Val Phe Ala Ser Ala Glu Arg
          20                25                30

Phe Ala Ala Leu Asn Leu Asn Thr Ala Arg Ser Ile Leu Glu Asp Ser
      35              40                45

Ile Ala Asn Ser Lys Ala Leu Leu Gly Ala Lys Asp Val Gln Glu Leu
      50              55                60

Val Ser Leu Gln Ala Ala Leu Ala Gln Pro Leu Val Glu Lys Ala Val
65              70                75              80

Ala Tyr Asn Arg Ser Val Tyr Glu Ile Ala Ser Gln Gly Gln Glu Glu
              85                90              95

Ile Ser Lys Leu Val Glu Thr Gln Ile Ala Glu Val Asn Lys Asn Leu
         100            105            110

Ser Leu Ala Leu Asp Lys Ala Ala Lys Ser Ala Pro Ala Gly Ser Asp
         115            120            125

Val Ala Val Ala Ala Val Lys Ser Ala Ile Ala Ala Asn Ser Ala
     130            135               140

Tyr Asp Ser Val Ser Lys Ala Ala Lys Gln Val Ala Glu Ile Ala Glu
145             150            155           160

```
Ala Asn Val Ala Ala Ala Thr Asn Ala Thr Val Lys Ala Val Gly Ala
                165                 170                 175

Ser Val Lys Thr Gly Val Lys Lys Ala Ala
            180                 185

<210> SEQ ID NO 96
<211> LENGTH: 188
<212> TYPE: PRT
<213> ORGANISM: Artificial Sequence
<220> FEATURE:
<223> OTHER INFORMATION: Sequence derived from Thauera sp. MZ1T

<400> SEQUENCE: 96

Met Ser Asn Phe Val Thr Pro Glu Gln Phe Ala Thr Ala Asn Lys Ala
1               5                   10                  15

Asn Ile Glu Thr Leu Leu Thr Leu Ala Asn Thr Ala Phe Ala Ser Ala
            20                  25                  30

Glu Arg Leu Ala Ala Leu Asn Leu Asn Thr Ala Arg Ser Leu Leu Glu
        35                  40                  45

Asp Gly Val Ala Asn Thr Lys Ala Leu Leu Ala Lys Asp Val Gln
    50                  55                  60

Glu Leu Val Asn Leu Gln Val Ser Leu Ala Gln Pro Ile Val Glu Lys
65                  70                  75                  80

Ala Val Ala Tyr Ala Arg Ser Val Tyr Glu Ile Ser Ser Gln Ser Gln
                85                  90                  95

Glu Glu Met Ser Lys Val Phe Glu Gly Gln Val Ala Glu Leu Asn Lys
            100                 105                 110

Gly Val Ala Thr Ala Leu Asp Lys Ala Ala Lys Ser Ala Pro Ala Gly
        115                 120                 125

Ser Asp Val Ala Val Ala Val Lys Ser Ala Ile Ala Ala Ala Asn
    130                 135                 140

Ser Ala Tyr Asp Ser Met Ser Lys Ala Ala Lys Gln Val Ala Glu Ile
145                 150                 155                 160

Ala Glu Ala Asn Val Ala Ala Thr Asn Ala Thr Val Lys Ala Val
                165                 170                 175

Ser Thr Thr Ala Lys Thr Thr Ala Lys Lys Ala Ala
            180                 185

<210> SEQ ID NO 97
<211> LENGTH: 188
<212> TYPE: PRT
<213> ORGANISM: Artificial Sequence
<220> FEATURE:
<223> OTHER INFORMATION: Sequence derived from Ralstonia eutropha H16

<400> SEQUENCE: 97

Met Thr Gln Trp Thr Ala Glu Gln Cys Thr Lys Ala Gln Met Ala Gly
1               5                   10                  15

Leu Glu Ala Met Ala Gly Leu Thr Asn Lys Val Leu Glu Gly Phe Glu
            20                  25                  30

Lys Val Met Asp Leu Asn Leu Gln Thr Met Lys Met Thr Leu Ala His
        35                  40                  45

Asn Arg Glu Gly Val Met Lys Ala Leu Ser Val Gln Asn Pro Gln Glu
    50                  55                  60

Leu Ile Glu Leu Gln Ile Glu Leu Phe Gln Pro Ala Ala Asp Lys Val
65                  70                  75                  80

Leu Glu Tyr Arg Arg Gln Leu His Asp Ile Leu Ala Ala Thr Arg Ala
```

```
                    85                  90                  95
Glu Phe Glu Lys Ile Ala Glu Val Gln Tyr Thr Thr Ser Lys Gly Gln
                100                 105                 110

Leu Gln Gly Leu Ile Asp Ser Ala Val Ser Asn Ala Pro Ser Gly Ser
            115                 120                 125

Thr Ala Pro Leu Ala Ala Trp Gln Glu Ala Val Lys Ala Thr Thr Ala
        130                 135                 140

Leu Tyr Glu Ser Met Gln Ser Thr Ala Lys Gln Ala Val Glu Val Ala
145                 150                 155                 160

Glu Asn Ser Phe Asn Thr Ala Ala Ala Ala Ser Lys Gly Ala Arg
                165                 170                 175

His Arg Ala Ala Leu Ala Ser Pro Ala Ala Lys
            180                 185

<210> SEQ ID NO 98
<211> LENGTH: 187
<212> TYPE: PRT
<213> ORGANISM: Artificial Sequence
<220> FEATURE:
<223> OTHER INFORMATION: Sequence derived from Herbaspirillum
      seropedicae SmR1

<400> SEQUENCE: 98

Met Thr Thr Tyr Thr Glu Gln Phe Ser Ala Ala Lys Ala Asn Ala
1               5                   10                  15

Glu Ala Gln Ile Ala Leu Phe Ser Gln Leu Ala Ser Lys Thr Phe Glu
                20                  25                  30

Gly Val Glu Lys Leu Val Asp Leu Asn Leu Lys Ala Ala Arg Ser Thr
            35                  40                  45

Leu Glu Glu Ser Gln Ala Ala Ala Gln Lys Leu Phe Ala Ala Lys Asp
        50                  55                  60

Pro Gln Glu Phe Phe Ala Leu Thr Ser Ala His Ala Gln Pro Thr Leu
65                  70                  75                  80

Glu Lys Ser Val Ala Tyr Gly Arg His Leu Ser Gly Ile Phe Ser Ser
                85                  90                  95

Thr Gln Ala Glu Leu Thr Lys Ala Ala Glu Ala Gln Ile Ala Glu Val
                100                 105                 110

Asn Arg Lys Val Val Ala Met Ile Asp Glu Val Ala Lys Asn Ala Pro
            115                 120                 125

Ala Gly Ser Glu Gln Ala Val Ser Val Leu Lys Ser Ala Ile Gly Asn
        130                 135                 140

Met Ser Ala Gly Tyr Glu Gln Phe Thr Lys Asn Ala Lys Gln Ala Ala
145                 150                 155                 160

Glu Val Leu Glu Ala Asn Val Thr Asn Ala Val Glu Gln Met Ser Gln
                165                 170                 175

Ala Gly Ala Lys Val Thr Arg Gly Ala Arg Lys
            180                 185

<210> SEQ ID NO 99
<211> LENGTH: 189
<212> TYPE: PRT
<213> ORGANISM: Artificial Sequence
<220> FEATURE:
<223> OTHER INFORMATION: Sequence derived from Sphingomonas sp. A1

<400> SEQUENCE: 99

Met Tyr Ala Thr Pro Glu Gln Phe Ala Ala Thr Asn Lys Ala Tyr Val
1               5                   10                  15
```

```
Glu Thr Leu Leu Thr Ile Ala Asn Thr Ser Phe Val Ser Ala Glu Lys
             20                  25                  30

Leu Ala Thr Leu Asn Leu Asn Ala Ala Arg Ala Val Leu Glu Asp Gly
         35                  40                  45

Val Ala Asn Ala Lys Ser Leu Leu Ala Val Lys Asp Ala His Glu Leu
 50                  55                  60

Val Asn Leu Gln Ala Ser Leu Ala Gln Pro Ser Val Glu Lys Leu Val
 65                  70                  75                  80

Ala Tyr Ser Arg His Val Tyr Asp Ile Ala His Gln Ala Gln Gln Glu
                 85                  90                  95

Ile Ala Gly Ile Leu Glu Ser Gln Leu Ala Glu Ile Asn Lys Asn Val
            100                 105                 110

Ala Ser Ala Leu Asp Lys Ala Ala Lys Ser Ala Pro Ala Gly Ser Asp
        115                 120                 125

Val Ala Val Ala Ala Val Lys Ser Ala Leu Ala Ala Ala Asn Ser Ala
130                 135                 140

Tyr Asp Ser Met Asn Lys Ala Ala Lys Gln Val Ala Glu Ile Ala Glu
145                 150                 155                 160

Ala Asn Val Ala Ala Ala Thr Asn Ala Thr Val Lys Ala Val Gly Ala
                165                 170                 175

Ser Ala Ser Ala Ala Ala Lys Thr Thr Lys Lys Val Ala
            180                 185

<210> SEQ ID NO 100
<211> LENGTH: 187
<212> TYPE: PRT
<213> ORGANISM: Artificial Sequence
<220> FEATURE:
<223> OTHER INFORMATION: Sequence derived from Leptothrix cholodnii SP-6

<400> SEQUENCE: 100

Met Thr Asn Pro Ala Glu Gln Ile Ala Ala Asn Lys Ala Ala Leu
1               5                  10                  15

Asp Asn Leu Val Thr Leu Thr Gln Gln Ala Phe Lys Gly Ile Glu Gln
            20                  25                  30

Leu Val Glu Leu Asn Met Gln Ala Ala Arg Ser Ser Ile Asp Asp Ser
         35                  40                  45

Val Glu Lys Ala Lys Ala Ala Leu Gly Ala Lys Asp Pro Gln Glu Phe
 50                  55                  60

Met Thr Ser Leu Gln Ala Asn Leu Gln Pro Ala Gln Asp Lys Ala Val
 65                  70                  75                  80

Ala Tyr Gly Arg Gln Val Ala Asp Ile Ala Ala Thr Gln Ala Glu
                 85                  90                  95

Val Ser Lys Leu Ala Glu Ala Gln Val Lys Ala Val Gln Glu Gln Phe
            100                 105                 110

Gln Ser Leu Val Asp Thr Ala Val Lys Asn Ala Pro Ala Gly Ser Glu
        115                 120                 125

Ser Ala Val Ala Ala Val Lys Ser Ala Ile Ala Asn Thr Thr Ala Ala
130                 135                 140

Phe Asp Ser Val Gln Lys Ala Ala Lys Gln Ala Ser Ala Ala Glu
145                 150                 155                 160

Ala Asn Phe Lys Gln Leu Ser Ala Thr Ala Glu Asn Thr Ala Lys Ala
                165                 170                 175

Ala Ala Glu Ala Val Lys Lys Ser Thr Lys Arg
            180                 185
```

<210> SEQ ID NO 101
<211> LENGTH: 174
<212> TYPE: PRT
<213> ORGANISM: Artificial Sequence
<220> FEATURE:
<223> OTHER INFORMATION: Sequence derived from Burkholderia phytofirmans PsJN

<400> SEQUENCE: 101

```
Met Tyr Phe Ser Thr Pro Glu Gln Phe Ile Ser Met Gln Ser Ala Asn
1               5                   10                  15

Val Ala Val Ala Phe Ser Leu Thr Gln Gln Thr Phe Gln Tyr Phe Glu
            20                  25                  30

Glu Leu Ala Lys Leu Asn Leu Gln Ala Ala Lys Ala Thr Leu Ala Glu
        35                  40                  45

Ser Glu Gln Ala Trp Gln Met Ala Met Ser Gly Lys Thr Pro Val Glu
    50                  55                  60

Leu Leu Val His Gln Ala Ser Asn Ala Lys Pro Val Ala Glu Lys Val
65                  70                  75                  80

Leu Ser Tyr Asn Ser His Met Leu Glu Ile Ala Asn Ala Ala Gln Ala
                85                  90                  95

Glu Phe Leu Lys Ile Phe Glu Asp Arg Phe Ala Gln Ser Asn Thr Lys
            100                 105                 110

Met Gln Thr Val Phe Glu Asp Leu Ala Arg Asn Ala Pro Ala Gly Ser
        115                 120                 125

Glu Leu Ala Val Thr Ala Phe Lys Ser Ala Val Ser Ser Ala Gly Ala
    130                 135                 140

Ala Tyr Asp Ala Met Arg Lys Ala Thr Ala Gln Ala Ile Ala Met Ala
145                 150                 155                 160

Gln Ala Ser Gln Leu Thr Val Pro Ala Pro Ala Arg Val Lys
                165                 170
```

<210> SEQ ID NO 102
<211> LENGTH: 186
<212> TYPE: PRT
<213> ORGANISM: Artificial Sequence
<220> FEATURE:
<223> OTHER INFORMATION: Sequence derived from Azoarcus sp. BH72

<400> SEQUENCE: 102

```
Met Thr Ala Thr Pro Glu Gln Ile Thr Ala Ala Lys Ala Asn Ile
1               5                   10                  15

Glu Thr Leu Leu Thr Leu Ala Asn Ser Ala Phe Ser Asn Val Glu Arg
            20                  25                  30

Leu Ala Ala Leu Asn Leu Asn Thr Ala Arg Ser Val Leu Glu Asp Gly
        35                  40                  45

Val Ala Asn Thr Lys Ala Leu Leu Ala Ala Lys Asp Val Gln Glu Phe
    50                  55                  60

Val Ser Leu Gln Thr Ser Leu Ala Gln Pro Leu Ile Glu Lys Ala Val
65                  70                  75                  80

Ala Tyr Asn Arg Ser Val Tyr Glu Ile Ala Ser Gln Ser Gln Glu Glu
                85                  90                  95

Leu Ser Lys Leu Phe Glu Gly Gln Val Ala Glu Leu Asn Lys Ser Leu
            100                 105                 110

Ala Ala Ala Leu Asp Lys Ala Ala Lys Ser Ala Pro Ala Gly Ser Asp
        115                 120                 125
```

```
Val Ala Val Ala Ala Val Lys Ser Ala Ile Ala Ala Asn Ser Ala
        130                 135                 140

Tyr Asp Ser Val Ser Lys Ala Lys Gln Val Ala Glu Ile Ala Glu
145                 150                 155                 160

Ala Asn Val Ala Ala Thr Asn Ala Thr Val Lys Ala Val Thr Thr
                165                 170                 175

Thr Ser Lys Ala Ala Ser Lys Lys Val Ala
                180                 185

<210> SEQ ID NO 103
<211> LENGTH: 174
<212> TYPE: PRT
<213> ORGANISM: Artificial Sequence
<220> FEATURE:
<223> OTHER INFORMATION: Sequence derived from Burkholderia xenovorans
      LB400

<400> SEQUENCE: 103

Met Tyr Phe Ser Met Pro Asp Gln Phe Ile Ser Met Gln Ser Ala Asn
1               5                   10                  15

Val Ala Val Ala Phe Ala Met Thr Gln Gln Thr Phe Gln Tyr Phe Glu
            20                  25                  30

Glu Leu Ala Lys Leu Asn Leu Gln Ala Lys Ala Thr Leu Ala Glu
        35                  40                  45

Ser Glu Gln Ala Trp Gln Leu Ala Thr Ser Gly Lys Thr Pro Val Glu
50                  55                  60

Leu Phe Val His Gln Ala Gly Asn Val Lys Pro Val Ala Glu Lys Val
65                  70                  75                  80

Leu Ser Tyr Asn Ser His Leu Phe Gly Ile Ala Asn Ser Val Gln Ala
                85                  90                  95

Glu Phe Leu Lys Leu Phe Glu Asp Arg Phe Ala Gln Ser Asn Ala Lys
            100                 105                 110

Met Gln Thr Val Val Asp Asp Phe Ala Arg Asn Ala Pro Ala Gly Ser
        115                 120                 125

Glu Val Ala Val Thr Val Phe Lys Ser Ala Val Ser Ser Ala Gly Ala
    130                 135                 140

Ala Tyr Asp Ala Met Arg Lys Ala Thr Ala Gln Ala Ile Ala Met Ala
145                 150                 155                 160

Gln Ala Gly Gln Ser Ser Ala Ser Ala Ser Thr Arg Val Lys
                165                 170

<210> SEQ ID NO 104
<211> LENGTH: 173
<212> TYPE: PRT
<213> ORGANISM: Artificial Sequence
<220> FEATURE:
<223> OTHER INFORMATION: Sequence derived from Ralstonia eutropha JMP134

<400> SEQUENCE: 104

Met Ser Ala Phe Thr Ser Asp Gln Phe Ala Ala Leu His Lys Thr Asn
1               5                   10                  15

Leu Ala Asn Leu Ala Met Met Ser Lys Ser Thr Ile Asp Gly Phe Gln
            20                  25                  30

Lys Leu Thr Glu Leu Asn Leu Lys Thr Ala Lys Ser Ala Leu Thr Glu
        35                  40                  45

Gly Gln Glu Asn Leu Lys Ala Val Leu Gly Gly Lys Asp Leu Arg Asp
    50                  55                  60

Val Leu Ala Val Gln Gly Ser Leu Ala Gln Pro Thr Thr Glu Lys Ala
```

```
                 65                  70                  75                  80
Ile Ser Tyr Ala Arg Gln Val Cys Glu Ile Ala Ala Gln Ala Gln Ala
                 85                  90                  95

Glu Leu Ala Arg Ala Val Glu Glu Gln Tyr Glu Gln His His Arg Asn
            100                 105                 110

Leu Gln Ala Phe Val Asp Thr Phe Val Lys Asn Ala Pro Ala Gly Ser
            115                 120                 125

Glu Ala Val Ser Ala Leu Leu Gln Ser Thr Val Asp Ala Ala Gly Asn
        130                 135                 140

Thr Tyr Arg Ser Ala Gln Ala Ile Ser Lys Gln Met Ser Asp Val Ala
145                 150                 155                 160

Arg Ser Asn Leu Ala Ala Ala Ala Ser Thr Lys Ala
                165                 170

<210> SEQ ID NO 105
<211> LENGTH: 178
<212> TYPE: PRT
<213> ORGANISM: Artificial Sequence
<220> FEATURE:
<223> OTHER INFORMATION: Sequence derived from Dechloromonas aromatica
      RCB

<400> SEQUENCE: 105

Met Ser Ile Asn Pro Glu Gln Leu Ala Ala Asn Lys Ala Ala Ile
1               5                  10                  15

Asp Ser Leu Leu Ser Val Ala Asn Thr Ala Leu Ala Ser Ala Glu Arg
                20                  25                  30

Ile Ala Thr Leu Asn Leu Glu Thr Ala Arg Ser Val Ile Glu Asp Ser
            35                  40                  45

Val Ser Gly Ala Lys Ala Leu Met Gly Ala Lys Asp Pro Gln Glu Ala
        50                  55                  60

Leu Ser Ile Gln Ala Ser Leu Thr Gln Pro Asn Val Glu Lys Ala Val
65                  70                  75                  80

Ala Tyr Ser Arg Ser Ile Tyr Glu Ile Ser Ala Gln Thr Gln Glu Gln
                85                  90                  95

Leu Ala Lys Met Val Glu Ala Gln Phe Gly Asp Phe Gln Lys Ser Val
            100                 105                 110

Ala Ser Met Leu Glu Lys Ala Ala Lys Ala Ala Pro Gly Gly Ser Asp
        115                 120                 125

Val Ala Val Asn Ala Phe Gln Ser Ala Ile Ala Ala Thr Ser Thr
    130                 135                 140

Phe Glu Asn Met Arg Lys Ala Ala Gln Gln Val Thr Glu Leu Ala Gln
145                 150                 155                 160

Ser Asn Met Ala Ala Thr Ser Ala Thr Thr Lys Ala Val Lys Lys
                165                 170                 175

Ser Lys

<210> SEQ ID NO 106
<211> LENGTH: 173
<212> TYPE: PRT
<213> ORGANISM: Artificial Sequence
<220> FEATURE:
<223> OTHER INFORMATION: Sequence derived from Burkholderia sp. Ch1-1

<400> SEQUENCE: 106

Met Tyr Phe Ser Thr Pro Asp Gln Phe Ile Ser Met Gln Ser Ala Asn
1               5                  10                  15
```

Val Ala Val Ala Phe Ser Leu Ala Gln Gln Thr Phe Gln Tyr Phe Glu
            20                  25                  30

Glu Leu Ala Arg Leu Asn Leu Gln Ala Arg Ala Thr Leu Ala Glu
        35                  40                  45

Ser Glu Gln Ala Trp Gln Leu Ala Val Ser Gly Lys Thr Pro Met Glu
50                  55                  60

Leu Phe Val Tyr Gln Ala Gly Asn Ala Lys Pro Val Ala Glu Lys Val
65                  70                  75                  80

Leu Ser Tyr Asn Ser His Leu Phe Gly Ile Ala Asn Ser Ala Gln Ala
            85                  90                  95

Glu Phe Leu Lys Leu Phe Glu Asp Arg Phe Ala Gln Ser Asn Ala Lys
            100                 105                 110

Met Gln Thr Ala Met Asp Asp Phe Ser Arg Asn Ala Pro Ala Gly Ser
            115                 120                 125

Glu Val Ala Val Thr Val Phe Lys Ser Ala Val Ser Ser Ala Gly Val
            130                 135                 140

Ala Tyr Glu Ala Met Arg Lys Ala Thr Ala Gln Ala Ile Ala Val Ala
145                 150                 155                 160

Gln Ala Gly Gln Ala Ala Pro Val Pro Thr Arg Asp Lys
            165                 170

<210> SEQ ID NO 107
<211> LENGTH: 182
<212> TYPE: PRT
<213> ORGANISM: Artificial Sequence
<220> FEATURE:
<223> OTHER INFORMATION: Sequence derived from Thauera sp. MZ1T

<400> SEQUENCE: 107

Met Thr Lys Ile Gln Thr Pro Glu Gln Phe Ala Ala Val Gly Gln Ala
1               5                   10                  15

Asn Leu Glu Ala Met Met Ser Leu Ala Asn Ser Ala Ile Ala Arg Ala
            20                  25                  30

Glu Arg Leu Ala Glu Leu Asn Leu Asn Thr Val Arg Ser Val Leu Glu
        35                  40                  45

Asp Ser Val Ala Thr Thr Arg Lys Leu Ala Glu Ala Lys Asp Pro Gln
50                  55                  60

Gln Leu Ala Lys Leu Gln Gly Glu Leu Thr Lys Pro Met Leu Asp Lys
65                  70                  75                  80

Ala Val Ala Tyr Ala Arg Ser Val Gln Glu Ile Ala Thr Glu Gly Gln
            85                  90                  95

Gln Glu Val Ser Asn Leu Phe Glu Lys Gln Ile Ala Asp Leu Asn Lys
            100                 105                 110

Arg Phe His Asp Met Leu Glu Gln Ala Ala Lys Gln Ala Pro Ala Gly
            115                 120                 125

Ser Glu Gly Val Phe Glu Ala Val Arg Ser Ala Met Asn Thr Ala Asn
            130                 135                 140

Ser Leu Tyr Asp Asn Ala Ser Lys Ala Ala Arg Gln Ala Ala Glu Val
145                 150                 155                 160

Ala Glu Ala Asn Met Ala Ala Thr Glu Ala Thr Val Lys Ala Val
            165                 170                 175

Ser Ala Ala Thr Lys Lys
            180

<210> SEQ ID NO 108
<211> LENGTH: 186

```
<212> TYPE: PRT
<213> ORGANISM: Artificial Sequence
<220> FEATURE:
<223> OTHER INFORMATION: Sequence derived from Ralstonia eutropha JMP134

<400> SEQUENCE: 108

Met Trp Thr Val Glu Gln Cys Lys Asn Val Gln Ala Ala Gly Leu Asp
1               5                   10                  15

Ala Met Leu Gly Leu Ala Lys Gln Gly Phe Asp Gly Phe Glu Lys Val
                20                  25                  30

Val Ala Leu Asn Leu Gln Thr Thr Lys Thr Ser Leu Ala Leu Thr Arg
            35                  40                  45

Glu Gly Val Leu Lys Ile Leu Ser Ala Gln Ser Pro Arg Glu Leu Ala
        50                  55                  60

Glu Leu Gln Ile Glu Trp Leu Gln Pro Leu Thr Asp His Ala Leu Thr
65                  70                  75                  80

Tyr Arg His Gln Leu Gln Asp Ile Leu Ala Ala Thr Arg Ala Glu Phe
                85                  90                  95

Ala Lys Val Ala Glu Ala Gln Tyr Ala Ala Ser Arg Gly Gln Leu Gln
                100                 105                 110

Asp Phe Phe Glu Gly Ala Val Ser Asn Ala Pro Ser Gly Ser Ala Ser
            115                 120                 125

Pro Leu Gly Ala Trp Gln Glu Ala Ile Lys Ala Thr Thr Met Leu Phe
        130                 135                 140

Glu Ser Met Gln Ser Thr Thr Lys Gln Ala Met Glu Val Ala Glu Gly
145                 150                 155                 160

Ser Phe Ser Thr Ala Val Glu Ala Ala Ser Lys Gly Val Arg Arg Arg
                165                 170                 175

Glu Ala Gln Thr Thr His Gly Ala Ala Lys
                180                 185

<210> SEQ ID NO 109
<211> LENGTH: 190
<212> TYPE: PRT
<213> ORGANISM: Artificial Sequence
<220> FEATURE:
<223> OTHER INFORMATION: Sequence derived from Ralstonia eutropha JMP134

<400> SEQUENCE: 109

Met Pro Glu Val Asn Leu Gln Pro Met Tyr Ala Ala Gln Ala Ala Ala
1               5                   10                  15

Met Asp Ile Val Phe Gly Met Thr Thr Lys Thr Leu Asp Ala Tyr Gln
                20                  25                  30

Arg Leu Thr Glu Leu Ser Met Gln Thr Met Lys Ala Thr Leu Ala Asp
            35                  40                  45

Asn Gln Glu Thr Val Arg Gln Ala Phe Ala Lys Ser Pro Gln Glu
        50                  55                  60

Phe Phe Ala Leu Gln Val Thr Val Glu Pro Ala Ala Glu Lys Ala
65                  70                  75                  80

Arg Ala Phe Phe Gln Gln Val Gln Glu Ile Ala Ala Thr Thr Arg Glu
                85                  90                  95

Glu Phe Gln Lys Val Ala Ala Gln Tyr Glu Thr Asn Lys Gln Thr
                100                 105                 110

Val Gln Gln Ile Phe Glu Lys Leu Ala Gln Asn Val Pro Ala Gly Ser
            115                 120                 125

Glu Gly Pro Phe Ser Ala Trp Gln Ala Ala Met Thr Ser Gly Ala Ser
        130                 135                 140
```

```
Leu Cys Glu Ser Met Gln Gln Ser Thr Lys Gln Ala Ile Glu Leu Ala
145                 150                 155                 160

Glu Thr Gln Val Ala Asn Ala Ala Ala Ala Ala Ala Gly His Lys
                165                 170                 175

Gly Gly Gly Gln Ser Ala Gly Arg Val Val Ala Lys Arg
            180                 185                 190

<210> SEQ ID NO 110
<211> LENGTH: 188
<212> TYPE: PRT
<213> ORGANISM: Artificial Sequence
<220> FEATURE:
<223> OTHER INFORMATION: Sequence derived from Pseudomonas stutzeri
      A1501

<400> SEQUENCE: 110

Met Ser Phe Phe Asp Ser Glu Lys Leu Gln Ser Ala Gln Lys Ala Asn
1               5                   10                  15

Leu Asp Leu Leu Gln Gln Ile Ser Gly Lys Val Phe Glu Ser Val Glu
            20                  25                  30

Gln Leu Ser Gln Leu Gln Phe Lys Ala Leu Arg Ala Ser Ser Gly Glu
        35                  40                  45

Gln Phe Asp Ser Leu Arg Lys Leu Leu Ser Val Arg Asp Pro Gln Ala
50                  55                  60

Phe Ala Glu Leu Gln Ala Ser Phe Ala Gln Pro Ala Ala Gln Ala Glu
65                  70                  75                  80

Arg Leu Leu Glu Phe Asn Arg Glu Val Tyr Asp Leu Val Ser Ser Thr
                85                  90                  95

Gln Ala Asp Ile Ala Lys Leu Ala Glu Arg Gln Val Glu Ala Gly Thr
            100                 105                 110

Lys Gln Val Arg Glu Leu Val Asp Val Ile Ala Lys Asn Ala Pro Ala
        115                 120                 125

Gly Ala Glu Pro Ala Val Ala Val Leu Lys Ser Ala Leu Glu Ser Ala
130                 135                 140

Gly Ser Val Tyr Glu Ser Ala Gln Lys Ala Ala Lys Gln Ala Ala Glu
145                 150                 155                 160

Ile Ala Glu Asn Gly Ile Ala Ala Ala Ser Ala Ala Gly Gln Ala
                165                 170                 175

Thr Arg Glu Ala Gly Lys Ala Ala Gly Gly Arg Lys
            180                 185

<210> SEQ ID NO 111
<211> LENGTH: 178
<212> TYPE: PRT
<213> ORGANISM: Artificial Sequence
<220> FEATURE:
<223> OTHER INFORMATION: Sequence derived from Methylibium
      petroleiphilum PM1

<400> SEQUENCE: 111

Met Leu Asn Thr Glu Gln Phe Ala Ala Thr Asn Lys Ala Asn Phe Glu
1               5                   10                  15

Ala Met Met Gly Leu Thr Ala Lys Ala Phe Gln Gly Val Glu Gln Leu
            20                  25                  30

Thr Ala Leu Asn Leu Gln Val Ala Lys Ala Gly Leu Asp Glu Ala Ala
        35                  40                  45

Glu Thr Gly Arg Ala Ala Leu Ser Ala Lys Asp Pro Gln Ala Leu Leu
50                  55                  60
```

```
Ala Leu Gln Ala Ala Pro Leu Gln Ala Ala Glu Lys Ala Thr Ala
 65                  70                  75                  80

Tyr Gly Lys Gln Val Tyr Gly Ile Val Ala Gly Ile Lys Ala Asp Val
                 85                  90                  95

Glu Lys Leu Ala Ala Glu Gln Ala Ala Ala Gln Ser Ser Phe Val
            100                 105                 110

Ala Leu Val Glu Ser Ala Gly Lys Asn Ala Pro Glu Gly Ala Val Asn
            115                 120                 125

Gly Ile Ala Leu Phe Lys Ser Ser Leu Ala Thr Met Asn Asn Ala Phe
130                 135                 140

Asp Gly Leu Gln Lys Ala Gly Arg Gln Ala Ala Glu Thr Ala Glu Ala
145                 150                 155                 160

Asn Tyr Ala Ala Val Thr Gly Ser Val Ile Lys Ala Ala Lys Thr Lys
                165                 170                 175

Arg Gly

<210> SEQ ID NO 112
<211> LENGTH: 186
<212> TYPE: PRT
<213> ORGANISM: Artificial Sequence
<220> FEATURE:
<223> OTHER INFORMATION: Sequence derived from Azotobacter vinelandii DJ

<400> SEQUENCE: 112

Met Ser Phe Phe Asp Leu Glu Lys Val Glu Ser Ala Ser Lys Ser Asn
1               5                   10                  15

Leu Asp Ala Val Gln Gln Leu Ser Ser Lys Leu Phe Glu Gly Ala Glu
            20                  25                  30

Glu Leu Ala Lys Leu Gln Phe Lys Thr Ile Arg Ala Ala Thr Asp Asp
        35                  40                  45

Asn Phe Glu Asn Leu Arg Lys Ile Ile Ser Val Arg Asp Pro Gln Ala
    50                  55                  60

Phe Leu Glu Leu Gln Ala Ser Phe Lys Pro Asn Glu Gln Ala Glu
65                  70                  75                  80

Arg Leu Val Glu Phe Ser Arg Gln Thr Tyr Asp Leu Ile Ser Arg Phe
                85                  90                  95

Gln Ala Glu Val Thr Arg Leu Thr Glu Arg Gln Ile Glu Ile Gly Thr
            100                 105                 110

Gln Gln Ala Gln Glu Ile Val Glu Glu Ile Cys Lys Asn Ala Pro Ala
        115                 120                 125

Ser Ala Glu Pro Val Val Ser Val Phe Lys Ser Ala Val Glu Gly Ala
    130                 135                 140

Gly Asn Val Tyr Glu Ser Ala Gln Arg Ala Ala Lys Gln Ala Ser Glu
145                 150                 155                 160

Ile Thr Ala Ser Gly Ile Glu Ala Ala Asn Ala Ala Gly Gln Ala
                165                 170                 175

Thr Ala Gln Ala Ala Gly Lys Lys Thr Ala
            180                 185

<210> SEQ ID NO 113
<211> LENGTH: 173
<212> TYPE: PRT
<213> ORGANISM: Artificial Sequence
<220> FEATURE:
<223> OTHER INFORMATION: Sequence derived from Ralstonia solanacearum
      UW551
```

<400> SEQUENCE: 113

Met Leu Lys Ser Glu His Val Ala Ala Thr His Lys Thr Gly Leu Glu
1               5                   10                  15

Ala Leu Ala Glu Leu Thr Ser Ala Thr Leu Asn Ser Val Glu Lys Leu
            20                  25                  30

Ser Glu Leu Gln Phe Gln Thr Val Arg Ala Ser Leu Glu Asp Ser Ala
        35                  40                  45

Glu Gln Gly Lys Arg Ala Phe Gly Ala Arg Ser Leu His Glu Leu Thr
    50                  55                  60

Glu Leu Gln Ser Glu Ser Ala Gln Pro Thr Glu Lys Leu Val Ala Tyr
65                  70                  75                  80

Gly Arg His Leu Tyr Gln Ile Ala Ala Gly Thr His Ala Glu Trp Arg
                85                  90                  95

Lys Val Ala Gln Ala Ser Ala Asn Glu Gln Cys Arg Ile Ala Leu Ala
            100                 105                 110

Trp Val Asp Asp Tyr Ala Lys Gln Ala Val Pro Gly Ser Glu Pro Ala
        115                 120                 125

Ile Ser Phe Met Arg Ser Thr Ile Ser Ala Thr Gln Arg Ala Cys Asp
    130                 135                 140

Ala Trp Gln Asp Ala Ser Val His Ala Ile His Leu Met Asp Asn Ala
145                 150                 155                 160

Leu Gln Ala Gly Ala Lys Thr Gly Lys Lys Ala Ser Ala
                165                 170

<210> SEQ ID NO 114
<211> LENGTH: 173
<212> TYPE: PRT
<213> ORGANISM: Artificial Sequence
<220> FEATURE:
<223> OTHER INFORMATION: Sequence derived from Ralstonia solanacearum
      PSI07

<400> SEQUENCE: 114

Met Leu Lys Ser Glu His Val Ala Ala Thr His Lys Thr Gly Leu Glu
1 5 10 15

Ala Leu Ala Glu Leu Thr Ser Ala Ala Leu Asn Ser Val Glu Lys Leu
20 25 30

Ser Glu Leu Gln Phe Gln Thr Val Arg Ala Ser Leu Glu Asp Thr Ala
35 40 45

Glu Gln Gly Met Arg Ala Phe Asp Ala Arg Ser Leu His Glu Leu Thr
50 55 60

Ala Leu Gln Ser Glu Ala Ser Gln Pro Ala Glu Lys Leu Val Ala Tyr
65 70 75 80

Gly Arg His Leu Tyr Gln Ile Ala Ala Gly Thr His Ala Glu Trp Arg
85 90 95

Lys Val Ala Gln Thr Arg Ala Asn Glu Gln Cys Arg Ile Ala Leu Ala
100 105 110

Trp Val Asp Asp Tyr Ala Lys Gln Ala Val Pro Gly Ser Glu Pro Ala
115 120 125

Val Ser Phe Met Arg Ser Thr Ile Thr Ala Ala Gln Arg Ala Cys Asp
130 135 140

Ala Trp Gln Asp Ala Ser Thr His Ala Ile His Leu Met Asp Asn Ala
145 150 155 160

Leu Gln Thr Ser Gly Lys Thr Thr Lys Lys Thr Ser Ala
165 170

<210> SEQ ID NO 115
<211> LENGTH: 193
<212> TYPE: PRT
<213> ORGANISM: Artificial Sequence
<220> FEATURE:
<223> OTHER INFORMATION: Sequence derived from Burkholderia vietnamiensis G4

<400> SEQUENCE: 115

```
Met Ser Val Phe Ala Pro Glu Lys Phe Ala Ala Asp Tyr Gln Ser Gly
1               5                   10                  15

Ile Ala Ala Trp Phe Ala Ile Ala Arg Pro Ala Ile Ser Gly Phe Glu
            20                  25                  30

Ala Val Val Glu Leu Asn Leu Gln Val Ala Arg Thr Ala Leu Ala Glu
        35                  40                  45

Tyr Glu Asp Lys Leu Lys Asn Ala Phe Asn Ala Ser Asn Pro Ala Ala
    50                  55                  60

Gly Phe Ala Gln Gln Val Ala Ala Pro Gln Glu Ala Ala Gly Lys Ala
65                  70                  75                  80

Ala Ala Tyr Gly Arg His Leu Phe Asp Ile Ala Val Ser Thr Gln Ala
                85                  90                  95

Glu Trp Ala Lys Val Ala Gln Ala Gln Tyr Glu Glu Thr Asp Lys Arg
            100                 105                 110

Val Lys Asp Val Val Gly Glu Leu Thr Lys His Ala Pro Ala Gly Ser
        115                 120                 125

Gly Ala Val Val Ala Ala Leu Asn Ser Ala Leu Ser Ala Ala Thr Ala
    130                 135                 140

Ala Ala Asp Ser Met Arg Ala Ala Thr Gly Gln Ala Ile Glu Ala Ala
145                 150                 155                 160

Gln Ser Gly Phe Asp Ala Val Ser Asp Thr Ala Ala Arg Gly Ala Lys
                165                 170                 175

Gln Thr Ala Ala Ala Ala Arg Lys Asp Ala Ala Ser Arg Glu Ser Ala
            180                 185                 190

Ala
```

<210> SEQ ID NO 116
<211> LENGTH: 188
<212> TYPE: PRT
<213> ORGANISM: Artificial Sequence
<220> FEATURE:
<223> OTHER INFORMATION: Sequence derived from Cupriavidus taiwanensis

<400> SEQUENCE: 116

```
Met Pro Thr Ser Asp Ile Glu Ala Ile Ala Ala Ala Gln Lys Ala Gly
1               5                   10                  15

Val Glu Ile Leu Tyr Gly Leu Thr Ser Arg Thr Leu Glu Gly Phe His
            20                  25                  30

Lys Val Ala Glu Leu Asn Leu Gln Thr Met Lys Trp Thr Leu Ala Glu
        35                  40                  45

Thr Gln Ala Cys Thr Arg Lys Ala Phe Glu Ala Lys Asn Asp Gly Asp
    50                  55                  60

Leu Pro Val Met Glu Ala Arg Ile Leu Leu Pro Leu Ala Glu Lys Ala
65                  70                  75                  80

Gln Ala Tyr Cys Arg Gln Gly Leu Glu Ile Ala Ala Glu Thr Arg Ala
                85                  90                  95

Asp Leu Ala Thr Val Val Glu Ala Gln Tyr Glu Gln Ser Lys Arg Val
            100                 105                 110
```

```
Met Gln Asp Tyr Ile Asp Ala Val Glu Arg Val Ala Pro Ser Gly Ser
            115                 120                 125

Gly Thr Ala Met Ala Ala Trp Lys Ser Ala Leu Thr Ala Thr Thr Ser
        130                 135                 140

Phe Leu Asp Ala Met Gln Arg Thr Ala Lys Gln Val Gly Asn Ile Thr
145                 150                 155                 160

Glu Asn Asn Val Asn Leu Ala Ala Ser Leu Ala Ser Ser Ser Ala Leu
                165                 170                 175

Gln Pro Ser Ser Asn Ala Ala Arg Ala Asp Lys Gly
            180                 185

<210> SEQ ID NO 117
<211> LENGTH: 173
<212> TYPE: PRT
<213> ORGANISM: Artificial Sequence
<220> FEATURE:
<223> OTHER INFORMATION: Sequence derived from Ralstonia solanacearum

<400> SEQUENCE: 117

Met Leu Lys Ser Glu His Val Ala Ala Thr His Lys Thr Gly Leu Asp
1               5                   10                  15

Ala Leu Ala Glu Leu Thr Gly Ala Ala Leu Asn Ser Val Glu Lys Leu
            20                  25                  30

Ser Glu Leu Gln Phe Gln Thr Val Arg Ala Ser Leu Glu Asp Ser Thr
        35                  40                  45

Glu Gln Ser Lys Arg Ala Phe Asp Ala Arg Ser Leu His Glu Leu Thr
    50                  55                  60

Ala Leu Gln Ser Glu Val Ser Gln Pro Thr Glu Lys Leu Met Ala Tyr
65                  70                  75                  80

Gly Gln His Leu Tyr Gln Ile Ala Ala Gly Thr His Ala Glu Trp Arg
                85                  90                  95

Lys Val Ala Gln Thr Arg Ala Asn Glu Gln Cys Arg Ile Ala Leu Ala
            100                 105                 110

Trp Val Asp Asp Tyr Ala Lys Gln Ala Val Pro Gly Ser Glu Pro Ala
        115                 120                 125

Ile Ser Phe Met Arg Ser Thr Ile Thr Ala Thr Gln Arg Ala Cys Asp
    130                 135                 140

Ala Trp Gln Asp Ala Ser Thr His Ala Ile His Leu Met Asp Asn Ala
145                 150                 155                 160

Leu Gln Ala Gly Ala Lys Ile Ala Lys Lys Thr Gly Ala
                165                 170

<210> SEQ ID NO 118
<211> LENGTH: 197
<212> TYPE: PRT
<213> ORGANISM: Artificial Sequence
<220> FEATURE:
<223> OTHER INFORMATION: Sequence derived from Dechloromonas aromatica
      RCB

<400> SEQUENCE: 118

Met Ser Asn Pro Asn Ile Glu Gln Leu Ala Ala Gln Lys Ala Asn
1               5                   10                  15

Ala Glu Val Met Leu Ala Leu Leu Arg Thr Ala Phe Asn Gly Val Glu
            20                  25                  30

Arg Leu Thr Ala Leu Asn Val Ala Ala Ser Arg Glu Phe Phe Asn Asn
        35                  40                  45
```

```
Ser Val Ala Asn Ser Gln Gln Leu Leu Gly Ala Lys Asp Ala Ala Ala
        50                  55                  60

Val Ala Lys Leu Asn Ala Glu Leu Ala Gln Pro Asn Leu Glu Lys Leu
 65                  70                  75                  80

Val Glu Tyr Ser Arg Asn Val Tyr Glu Leu Thr Thr Asp Val Gln Lys
                 85                  90                  95

Glu Leu Thr Ser Val Ile Glu Ala Gln Tyr Gly Asn Leu Thr Lys Asn
            100                 105                 110

Ala Ala Ser Ala Val Gln Lys Ala Ser Ala Ser Ala Pro Ile Gly Gly
            115                 120                 125

Asp Val Phe Ala Ala Met Asn Ser Val Ile Asn Ala Ser Ser Gln
130                 135                 140

Ala Phe Glu Ser Leu Asn Ser Val Thr Arg Gln Leu Ser Glu Ile Ala
145                 150                 155                 160

Glu Ala Asn Ile Gln Thr Ala Thr Lys Ala Thr Gly Thr Lys Ala Ala
                165                 170                 175

Ala Thr Lys Ala Pro Ala Lys Thr Ser Ala Thr Ala Ala Ala Lys
            180                 185                 190

Lys Ser Thr Ala Lys
            195

<210> SEQ ID NO 119
<211> LENGTH: 173
<212> TYPE: PRT
<213> ORGANISM: Artificial Sequence
<220> FEATURE:
<223> OTHER INFORMATION: Sequence derived from Ralstonia solanacearum
      CFBP2957

<400> SEQUENCE: 119

Met Leu Lys Ser Glu His Val Ala Ala Thr His Lys Thr Gly Le

-continued

```
<220> FEATURE:
<223> OTHER INFORMATION: Sequence derived from Azotobacter sp. FA8

<400> SEQUENCE: 120

Met Ala Phe Phe Asp Leu Glu Lys Met Glu Ser Ala Ser Lys Ser Asn
1               5                   10                  15

Leu Asp Ala Val Gln Gln Leu Asn Ser Lys Ile Phe Glu Ser Ala Glu
            20                  25                  30

Glu Leu Tyr Lys Leu Gln Phe Lys Thr Leu Arg Ala Ala Ala Asp Asp
        35                  40                  45

Asn Phe Glu Ser Leu Arg Lys Leu Leu Ser Val Arg Asp Pro Gln Ala
    50                  55                  60

Phe Leu Glu Leu Gln Ala Ser Phe Phe Lys Pro Asn Glu Gln Ala Glu
65                  70                  75                  80

Arg Leu Val Glu Phe Ser Arg Gln Thr Tyr Asp Leu Ile Ser Arg Phe
                85                  90                  95

Gln Ala Glu Val Thr Lys Leu Thr Glu Arg Gln Ile Glu Ile Gly Thr
            100                 105                 110

Gln Gln Ala Gln Glu Ile Val Glu Glu Ile Cys Lys Asn Ala Pro Ala
        115                 120                 125

Ser Ala Glu Pro Val Val Ser Val Phe Lys Ser Ala Val Glu Gly Ala
    130                 135                 140

Gly Asn Val Tyr Glu Ser Ala Gln Lys Ala Ala Lys Gln Ala Ser Glu
145                 150                 155                 160

Ile Thr Ala Ser Gly Ile Glu Ala Ala Ala Asn Ala Ala Gly Gln Ala
                165                 170                 175

Ala Ala Gln Ala Ala Ser Gly Lys Lys Thr Ala
            180                 185

<210> SEQ ID NO 121
<211> LENGTH: 187
<212> TYPE: PRT
<213> ORGANISM: Artificial Sequence
<220> FEATURE:
<223> OTHER INFORMATION: Sequence derived from Dechloromonas aromatica
      RCB

<400> SEQUENCE: 121

Met Ala Phe Asn Phe Thr Thr Pro Glu Gln Phe Ala Ser Ala Asn Lys
1               5                   10                  15

Ala Thr Val Asp Ser Leu Leu Ser Val Ala Asn Ala Ala Leu Ala Ser
            20                  25                  30

Ala Glu Arg Ile Ala Ala Leu Asn Leu Asn Thr Ala Arg Ser Val Leu
        35                  40                  45

Glu Asp Ser Val Ser Gly Thr Lys Ala Leu Leu Gly Ala Lys Asp Val
    50                  55                  60

Gln Glu Ala Ile Ser Ile Gln Ala Ser Leu Ala Gln Pro Asn Val Glu
65                  70                  75                  80

Lys Ala Val Ala Tyr Ser Arg Ser Val Tyr Glu Ile Ser Ala Gln Ala
                85                  90                  95

Gln Glu Glu Leu Ser Lys Ser Ile Glu Ala Gln Phe Gly Gly Phe Gln
            100                 105                 110

Lys Gln Val Ala Asp Leu Leu Asp Lys Ala Ala Lys Ser Ala Pro Ala
        115                 120                 125

Gly Ser Asp Val Ala Val Ala Val Lys Ser Ala Ile Ala Ala Ala
    130                 135                 140
```

```
Asn Ser Ala Phe Asp Asn Leu Asn Lys Ala Ala Lys Gln Val Ala Glu
145                 150                 155                 160

Ile Thr Glu Ala Asn Val Ala Ala Thr Asn Ala Thr Val Lys Ala
                165                 170                 175

Val Ser Ala Ser Thr Ala Ala Ser Lys Arg Lys
                180             185
```

METHODS, CHIMERIC POLYPEPTIDES, POLYNUCLEOTIDES AND CELLS FOR PRODUCING BIOPLASTICS

CROSS-REFERENCE TO RELATED APPLICATIONS

This application claims the priority of U.S. Provisional Application Ser. No. 61/252,967, entitled "A NOVEL USE OF THE PHASIN PROTEIN FOR THE PURIFICATION OF POLYHYDROXYALKANOATES (PHAs)," filed on 19 Oct. 2009, the entire contents and substance of which are hereby incorporated by reference herein.

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISK APPENDIX

This application includes a 181 KB computer readable sequence listing created on Oct. 19, 2010 using Pat-In 3.5 and entitled "Phasin_ST25," the entire contents of which is hereby incorporated by reference herein.

PRIORITY CLAIM

This application claims priority under 35 U.S.C. 119(e) to U.S. Provisional Application No. 61/252,967.

BACKGROUND

Polyhydroxyalkanoates (PHAs) are polyesters accumulated by a variety of microorganisms in response to nutrient limitation or an environmental stress. The intracellular storage of these bioplastics provides a reserve of carbon, energy, and reducing power. The material properties of PHAs are similar to those of traditional petroleum-based plastics, like polypropylene, which enables their use in commercial and medical applications. Additionally, PHAs have the advantages of biodegradability and renewability, therefore providing a sustainable source of non-petrochemically-derived plastic.

The high cost of microbial PHA production has limited the use and application of these materials. Specifically, downstream processing and purification procedures can be as much as 50% of the total expense. Traditional PHA downstream processing methods involving the use of solvents, enzymatic digestion, or mechanical disruption are often impractical for industrial-scale recovery.

BRIEF DESCRIPTION

Disclosed herein is a system whereby a PHA specific binding protein is fused to a signal sequence, allowing for the bioplastic to be transported out of the cell or transported to a cellular domain to facilitate purification. This technology will reduce purification costs for bioplastic production, as well as allow for production of bioplastics in continuous culture since the bacteria will not need to be destroyed in any downstream processing.

Methods of producing bioplastics are disclosed, as are chimeric polypeptides useful to transport polyhydroxyalkanoates (PHAs), polynucleotides that code for the chimeric polypeptides, cells harboring the chimeric polypeptides and methods of transporting PHAs.

One aspect of the invention includes chimeric polypeptides. In one embodiment, the chimeric polypeptide comprises a phasin or a phasin analog which binds to a PHA and a signal sequence. In another embodiment, the signal sequence is N-terminal to the phasin or phasin analog. In another embodiment, the signal sequence is C-terminal to the phasin or phasin analog. In another embodiment, the signal sequence is connected to the phasin or phasin analog by a linker.

In another embodiment of chimeric polypeptides, the signal sequence is one of SEQ ID NO: 8, 9, 10, 11, 12, 13, 14, 15, 16, 17, 18, 19, 20, 21, 22, or 23. In another embodiment, the signal sequence is one of: SEQ ID NO: 8, 9, 10, 11, or 12. In another embodiment, the polypeptide comprises a phasin, and the phasin is one of 1-7 or 29-121. In another embodiment of chimeric polypeptides the phasin is SEQ ID NO:1. In another embodiment, the polypeptide comprises SEQ ID NO: 1 and one of SEQ ID NO: 8, 9, 10, 11, or 12.

In another embodiment, the chimeric polypeptide comprises a phasin analog which binds to a PHA. In another embodiment, the phasin analog comprises a phasin sequence with one or more residue additions, substitutions, or deletions, wherein the analog meets the default threshold to be marked as bearing a phasin domain by a phasin Hidden Markov Model.

Other aspects of the invention include polynucleotides which code for a chimeric polypeptide. In one embodiment, the polynucleotide comprises a sequence which codes for a chimeric polypeptide, the chimeric polypeptide comprising a phasin or a phasin analog which binds to a PHA, and a signal sequence.

In another embodiment, the polynucleotide further comprises a promoter sequence disposed 5' of the sequence which codes for the chimeric polypeptide, wherein the promoter may drive transcription of the polynucleotide to create an mRNA which codes for the chimeric polypeptide. In a related embodiment, the polynucleotide comprises a ribosomal binding site disposed between the promoter and the sequence which codes for the chimeric polypeptide such that the mRNA which codes for the chimeric polypeptide will also comprise a ribosomal binding site, and the mRNA which codes for the chimeric polypeptide may be translated to form the chimeric polypeptide. In another embodiment, the polynucleotide comprises one or more terminator sequences 3' of the sequence which codes for the chimeric polypeptide, wherein the terminator sequences may terminate transcription of the polynucleotide. In a related embodiment, the promoter, the ribosomal binding site and the one or more terminators are adapted for use in a prokaryotic cell. In a related embodiment, the promoter, the ribosomal binding site and the one or more terminators are adapted for use in a bacterial cell. In a related embodiment, the promoter, the ribosomal binding site and the one or more terminators are adapted for use in a gram-negative bacterial cell. In a related embodiment, the promoter, the ribosomal binding site and the one or more terminators are adapted for use in an *E. coli* cell.

In another embodiment, the polynucleotide comprises a signal sequence which is one of SEQ ID NO: 8, 9, 10, 11, 12, 13, 14, 15, 16, 17, 18, 19, 20, 21, 22, or 23. In another embodiment, the polypeptide comprises a phasin, and the phasin is one of: 1-7 or 29-121. In another embodiment, the polypeptide comprises a phasin analog which binds to a PHA, wherein the phasin analog a phasin sequence with one or more residue substitutions, wherein the analog meets the default threshold to be marked as bearing a phasin domain by a phasin Hidden Markov Model.

In another embodiment, the sequence which codes for the chimeric polypeptide comprises a sequence which codes for SEQ ID NO: 1; and a sequence which codes for a signal sequence selected from SEQ ID NO: 8, 9, 10, 11, or 12.

In another embodiment, the ribosomal binding site comprises B0034, wherein the one or more terminators comprise B0015, and wherein the promoter is one of: the Lac promoter, the TetR promoter, the Lac pL Hybrid promoter, or the Lambda pl Regulated promoter.

Other aspects of the invention include a cell bearing chimeric polypeptides. In one embodiment, the cell comprises any chimeric polypeptide or polynucleotide discussed above. In a related embodiment, the cell is a prokaryotic cell. In a related embodiment, the cell is a bacterial cell. In a related embodiment, the cell is a gram-negative bacterial cell. In a related embodiment, the cell is an *E. coli* cell.

In another embodiment, the cell comprises an expression system for PHA anabolic enzymes. In another embodiment, the expression system for PHA anabolic enzymes comprises SEQ ID NO:25, SEQ ID NO:26 and SEQ ID NO:27. In another embodiment, the expression system for PHA anabolic enzymes comprises the plasmid pBHR68, and the polynucleotide comprises SEQ ID NO:1 connected to SEQ ID NO:8.

Another aspect of the invention includes methods of producing a bioplastic. In one embodiment, the method comprises providing a cell which produces one or more PHAs, providing to the cell a chimeric polypeptide comprising a phasin or a phasin analog which binds to a PHA, and collecting a PHA which has been transported by association with the chimeric polypeptide. Another aspect of the invention includes methods of transporting a PHA. In one embodiment, the method comprises providing a chimeric polypeptide to the cell, the chimeric polypeptide comprising a phasin or a phasin analog which binds to a PHA; and a signal sequence.

Either methods of producing a bioplastic or methods of transporting a PHA may encompass the additional embodiments described below.

In one embodiment, the step of providing a chimeric polypeptide to the cell comprises providing to the cell a polynucleotide comprising a sequence which codes for the chimeric polypeptide, wherein the cell expresses the chimeric polypeptide coded for by the polynucleotide.

In another embodiment, the signal sequence is one of SEQ ID NO: 8, 9, 10, 11, 12, 13, 14, 15, 16, 17, 18, 19, 20, 21, 22, or 23. In another embodiment, the polypeptide comprises a phasin, and the phasin is one of: 1-7 or 29-121. In another embodiment, the polypeptide comprises a phasin analog which comprises a phasin sequence with one or more residue additions, substitutions, or deletions, wherein the analog meets the default threshold to be marked as bearing a phasin domain by a phasin Hidden Markov Model.

In another embodiment, the step of providing to the cell a polynucleotide comprises transforming the cell with the polynucleotide. In one embodiment, the cells used are bacterial. In another embodiment, the cells are *E. coli* cells.

In another embodiment, the chimeric polypeptide comprises SEQ ID NO: 1; and a signal sequence selected from SEQ ID NO: 8, 9, 10, 11, or 12.

In another embodiment, an additional step of providing to the cell an expression system for PHA anabolic enzymes is performed.

In another embodiment, the expression system for PHA anabolic enzymes comprises SEQ ID NO:25, SEQ ID NO: 26 and SEQ ID NO:27. In another embodiment, the expression system for PHA anabolic enzymes comprises pBHR68, and the polynucleotide comprises SEQ ID NO:1 connected to SEQ ID NO:8.

In another embodiment, the PHA is transported outside the cell. In another embodiment, the PHA is transported to the periplasmic space.

In any embodiment described above, the PHA may be polyhydroxybutyrate PHB. Furthermore, the cell may also comprise the plasmid pLG575, and the methods may comprise providing pLG575 to the cell. Furthermore, any method may further comprise the step of growing the cell in continuous culture.

BRIEF DESCRIPTION OF THE DRAWINGS

FIG. 1A-H. Depicts an alignment of selected phasin sequences. The sequences identified were aligned using Cobalt.

FIG. 5. Layout of constructed plasmids representing several embodiments of the polynucleotides described.

FIG. 6. The phasin genetic sequence after a point mutation of a G to a T nucleotide at position 114 for the removal of a PstI restriction enzyme site (SEQ ID NO:28). The location of the removed restriction site is underlined.

FIG. 12A-D. SEM image of E. coli with genes for PHB production and ability to secrete phasin/PHB. E. coli were transformed with pLG575 and pBHR68:PhaP1:HlyA and imaged.

FIG. 14. NMR identification of PHB in the media.

DETAILED DESCRIPTION

Definitions

Figure 2:
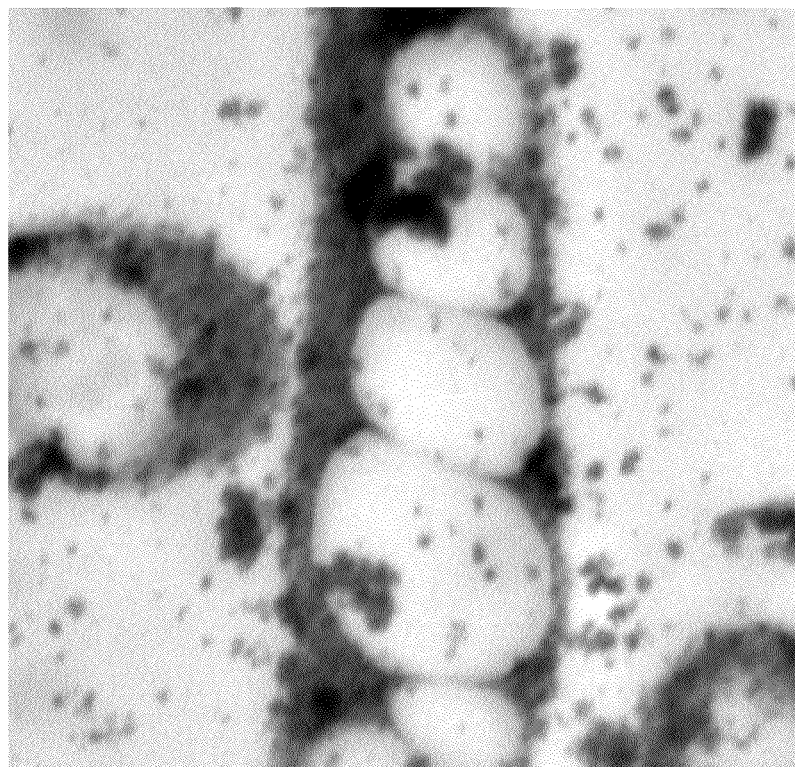
FIG. 2. Polyhydroxyalkanoate granules inside of *Cupriavidus necator* H16.

"Chimeric polypeptide" means a protein that comprises a first polypeptide connected to a second polypeptide, where the first and second polypeptides are not found connected in nature. The first and second polypeptides may be connected by a peptide bond, or a linker.

"Phasin" means an amphipathic protein found associated with PHA granules in cells. Phasins are thought to stabilize the PHA granules. Phasins have been identified in many species, including Cupriavidus necator, Ralstonia euthera, Burkholderia multivorans, Comamonas testosteroni, Rhodoferax ferrireducens, and Polaromonas naphthalenivorans. Table 1 gives a representative listing of phasin proteins. Furthermore, FIG. 1 shows an alignment of the sequences in Table 1.

TABLE 1

Representative phasin proteins

| SEQ ID NO: | NCBI Accession Number | Description |
|---|---|---|
| 1 | YP_725885.1 | phasin (PhaP) [Cupriavidus necator] |
| 2 | 2111322A | GA24 protein [Alcaligenes eutrophus] |
| 3 | YP_002005324.1 | phasin; polyhydroxyalkanoate synthesis and granule formation regulator/factor [Cupriavidus taiwanensis] |
| 4 | YP_583355.1 | phasin [Cupriavidus metallidurans CH34] |
| 5 | YP_001899509.1 | phasin family protein [Ralstonia pickettii 12J] |
| 6 | NP_519726.1 | hypothetical protein RSc1605 [Ralstonia solanacearum GMI1000] |
| 7 | YP_002981570.1 | phasin family protein [Ralstonia pickettii 12D] |
| 29 | YP_003752340.1 | phasin; polyhydroxyalkanoate synthesis and granule formation regulator/factor [Ralstonia solanacearum PSI07] |
| 30 | ZP_00942918.1 | granule-associated protein [Ralstonia solanacearum UW551] |
| 31 | YP_002231333.1 | phasin-like protein [Burkholderia cenocepacia J2315] |
| 32 | YP_369678.1 | phasin [Burkholderia sp. 383] |
| 33 | ZP_03571485.1 | phasin [Burkholderia multivorans CGD2M] |
| 34 | YP_001857695.1 | phasin family protein [Burkholderia phymatum STM815] |
| 35 | ZP_04945277.1 | hypothetical protein BDAG_01165 [Burkholderia dolosa AUO158] |
| 36 | YP_001579323.1 | phasin family protein [Burkholderia multivorans ATCC 17616] |
| 37 | YP_003605474.1 | phasin family protein [Burkholderia sp. CCGE1002] |
| 38 | YP_774061.1 | phasin family protein [Burkholderia ambifaria AMMD] |
| 39 | YP_625781.1 | phasin [Burkholderia cenocepacia AU 1054] |
| 40 | YP_001896207.1 | phasin family protein [Burkholderia phytofirmans PsJN] |
| 41 | ZP_02374191.1 | phasin family protein [Burkholderia thailandensis TXDOH] |
| 42 | ZP_02885879.1 | phasin family protein [Burkholderia graminis C4D1M] |
| 43 | ZP_04902353.1 | phasin family protein [Burkholderia pseudomallei S13] |
| 44 | YP_001120051.1 | phasin family protein [Burkholderia vietnamiensis G4] |
| 45 | YP_108894.1 | phasin-like protein [Burkholderia pseudomallei K96243] |
| 46 | YP_442397.1 | phasin family protein [Burkholderia thailandensis E264] |
| 47 | ZP_00441758.1 | phasin family protein [Burkholderia mallei GB8 horse 4] |
| 48 | YP_559463.1 | phasin [Burkholderia xenovorans LB400] |
| 49 | ZP_02464059.1 | phasin family protein [Burkholderia thailandensis MSMB43] |
| 50 | ZP_02356283.1 | phasin family protein [Burkholderia oklahomensis EO147] |
| 51 | ZP_03270753.1 | phasin family protein [Burkholderia sp. H160] |
| 52 | YP_002254539.1 | polyhydroxybutyrate granule-associated protein (phasin) phap1 [Ralstonia solanacearum MolK2] |
| 53 | YP_002912259.1 | Phasin-like protein [Burkholderia glumae BGR1] |
| 54 | ZP_02379121.1 | Phasin [Burkholderia ubonensis Bu] |
| 55 | YP_003277457.1 | phasin family protein [Comamonas testosteroni CNB-2] |
| 56 | YP_001565756.1 | phasin family protein [Delftia acidovorans SPH-1] |
| 57 | ZP_03544352.1 | phasin family protein [Comamonas testosteroni KF-1] |
| 58 | YP_523395.1 | phasin [Rhodoferax ferrireducens T118] |
| 59 | YP_549900.1 | phasin [Polaromonas sp. JS666] |
| 60 | YP_986731.1 | phasin family protein [Acidovorax sp. JS42] |
| 61 | YP_981847.1 | phasin family protein [Polaromonas naphthalenivorans CJ2] |
| 62 | YP_002552830.1 | phasin family protein [Acidovorax ebreus TPSY] |
| 63 | ZP_07024764.1 | phasin family protein [Alicycliphilus denitrificans BC] |
| 64 | YP_971643.1 | phasin family protein [Acidovorax avenae subsp. citrulli AAC00-1] |
| 65 | YP_001155519.1 | phasin family protein [Polynucleobacter necessarius subsp. asymbioticus QLW-P1DMWA-1] |
| 66 | CAZ87940.1 | Granule-associated protein (Phasin) [Thiomonas sp. 3As] |
| 67 | YP_003642715.1 | phasin family protein [Thiomonas intermedia K12] |
| 68 | YP_997317.1 | phasin family protein [Verminephrobacter eiseniae EF01-2] |

TABLE 1-continued

Representative phasin proteins

| SEQ ID NO: | NCBI Accession Number | Description |
|---|---|---|
| 69 | ZP_06210175.1 | phasin family protein [*Acidovorax avenae* subsp. *avenae* ATCC 19860] |
| 70 | YP_002943682.1 | phasin family protein [*Variovorax paradoxus* S110] |
| 71 | ZP_04761740.1 | phasin family protein [*Acidovorax delafieldii* 2AN] |
| 72 | YP_001020703.1 | hypothetical protein Mpe_A1506 [*Methylibium petroleiphilum* PM1] |
| 73 | YP_001791024.1 | phasin family protein [*Leptothrix cholodnii* SP-6] |
| 74 | YP_002005766.1 | phasin; polyhydroxyalkanoate synthesis and granule formation regulator/factor [*Cupriavidus taiwanensis*] |
| 75 | YP_726637.1 | phasin (PHA-granule associated protein) [*Ralstonia eutropha* H16] |
| 76 | AAR38792.1 | PHA-granule associated protein 3 [*Ralstonia eutropha* H16] |
| 77 | YP_001352419.1 | hypothetical protein mma_0729 [*Janthinobacterium* sp. Marseille] |
| 78 | YP_787252.1 | granule-associated protein (phasin) [*Bordetella avium* 197N] |
| 79 | ABW82969.1 | PHA granule-associated protein [uncultured bacterium pEAF66] |
| 80 | YP_983322.1 | phasin family protein [*Polaromonas naphthalenivorans* CJ2] |
| 81 | YP_001895980.1 | phasin family protein [*Burkholderia phytofirmans* PsJN] |
| 82 | YP_001099132.1 | granule-associated protein phasin [*Herminiimonas arsenicoxydans*] |
| 83 | YP_549125.1 | phasin [*Polaromonas* sp. JS666] |
| 84 | YP_298066.1 | phasin [*Ralstonia eutropha* JMP134] |
| 85 | YP_983688.1 | phasin family protein [*Polaromonas naphthalenivorans* CJ2] |
| 86 | YP_001887976.1 | phasin family protein [*Burkholderia phytofirmans* PsJN] |
| 87 | YP_001629533.1 | hypothetical protein Bpet0930 [*Bordetella petrii* DSM 12804] |
| 88 | YP_841533.1 | phasin (PHA-granule associated protein) [*Ralstonia eutropha* H16] |
| 89 | ZP_02881484.1 | phasin family protein [*Burkholderia graminis* C4D1M] |
| 90 | NP_881967.1 | hypothetical protein BP3441 [*Bordetella pertussis* Tohama I] |
| 91 | YP_003778128.1 | hypothetical protein Hsero_4759 [*Herbaspirillum seropedicae* SmR1] |
| 92 | ZP_06686090.1 | phasin family protein [*Achromobacter piechaudii* ATCC 43553] |
| 93 | YP_003165918.1 | phasin family protein [*Candidatus Accumulibacter phosphatis* clade IIA str. UW-1] |
| 94 | YP_524362.1 | phasin [*Rhodoferax ferrireducens* T118] |
| 95 | YP_157742.1 | hypothetical protein ebA1323 [*Aromatoleum aromaticum* EbN1] |
| 96 | YP_002354538.1 | phasin family protein [*Thauera* sp. MZ1T] |
| 97 | NP_942840.1 | phasin [*Ralstonia eutropha* H16] |
| 98 | YP_003775060.1 | phasin family protein protein [*Herbaspirillum seropedicae* SmR1] |
| 99 | BAD38885.1 | alginate granule-binding protein [*Sphingomonas* sp. A1] |
| 100 | YP_001793324.1 | phasin family protein [*Leptothrix cholodnii* SP-6] |
| 101 | YP_001889866.1 | phasin family protein [*Burkholderia phytofirmans* PsJN] |
| 102 | YP_932293.1 | phasin [*Azoarcus* sp. BH72] |
| 103 | YP_553002.1 | phasin [*Burkholderia xenovorans* LB400] |
| 104 | YP_298545.1 | phasin [*Ralstonia eutropha* JMP134] |
| 105 | YP_286219.1 | phasin [*Dechloromonas aromatica* RCB] |
| 106 | ZP_06844451.1 | phasin family protein [*Burkholderia* sp. Ch1-1] |
| 107 | YP_002355664.1 | phasin family protein [*Thauera* sp. MZ1T] |
| 108 | YP_293207.1 | phasin [*Ralstonia eutropha* JMP134] |
| 109 | YP_299114.1 | phasin [*Ralstonia eutropha* JMP134] |
| 110 | YP_001171240.1 | phasin PhaP [*Pseudomonas stutzeri* A1501] |
| 111 | YP_001022794.1 | hypothetical protein Mpe_A3606 [*Methylibium petroleiphilum* PM1] |
| 112 | YP_002799530.1 | phasin protein [*Azotobacter vinelandii* DJ] |
| 113 | ZP_00944212.1 | granule-associated protein [*Ralstonia solanacearum* UW551] |
| 114 | YP_003753962.1 | putative polyhydroxybutyrate granule-associated protein (Phasin) phaP [*Ralstonia solanacearum* PSI07] |
| 115 | YP_001120704.1 | phasin family protein [*Burkholderia vietnamiensis* G4] |
| 116 | YP_001796368.1 | Phasin (PHA-granule associated protein) [*Cupriavidus taiwanensis*] |
| 117 | CBJ39631.1 | putative polyhydroxybutyrate granule-associated protein (Phasin) phap2 [*Ralstonia solanacearum*] |
| 118 | YP_286622.1 | phasin [*Dechloromonas aromatica* RCB] |
| 119 | YP_003747173.1 | putative polyhydroxybutyrate granule-associated protein (Phasin) phaP [*Ralstonia solanacearum* CFBP2957] |
| 120 | CAD42757.1 | PhaP protein [*Azotobacter* sp. FA8] |
| 121 | YP_286621.1 | phasin [*Dechloromonas aromatica* RCB] |

The phasins are a well defined class of proteins whose sequences are found in publicly available databases.

"Phasin analog" means a phasin protein bearing one or more additions deletions or substitutions of residues compared to the original phasin.

Useful phasin analogs include those that retain the property of binding one or more PHAs. By examining and aligning known phasin sequences, a skilled person can determine which phasin residues are conserved across species. Using this alignment, the skilled person could generate a consensus sequence, using, for example, the Clustal algorithm. Since conserved residues are generally those which are required for function (Boffelli D, Nobrega M A, Rubin E M. *Comparative genomics at the vertebrate extremes.* Nat Rev Genet. 2004; 5:456-465), non-naturally occurring proteins that conform to this consensus sequence would define phasin analogs that likely have the property of binding PHA. For example, an alignment was generated using SEQ ID NOS:1-7, and 29-121. The alignment is presented in FIG. 1.

Alternatively, generating phasin analogs with the property of binding PHA could also be accomplished by using existing bioinformatic resources. Proteins and protein domains are often described by a Hidden Markov Model (HMM). An HMM of a polypeptide is not a sequence alignment, but it does convey actual structural information about the protein. Most HMMs are based on the probability of any particular residue occurring next to a second residue in the linear sequence of the polypeptide. Using HMMs to describe proteins is discussed in Krogh A, Brown M, Mian I S, Sjölander K, Haussler D, *Hidden Markov models in computational biology. Applications to protein modeling.* J Mol. Biol. 1994; 235; 1501-31, which is hereby incorporated by reference.

The European Bioinformatics Institute maintains the Interpro database, which compiles Hidden Markov Model (HMM) information from various databases, including some described below. Interpro has five different entries which describe phasins. These entries are IPR010127 (Phasin, subfamily 1), IPR018968 (Phasin), IPR010234 (Phasin, subfamily 2), IPR014176 (Phasin, subfamily 3), and IPR008769 (Poly granule associated).

The Wellcome Trust Sanger Institute maintains the Pfam database, which describes the phasin proteins in terms of HMMs. The Pfam HMMs that define the phasin proteins are PF05597, PF09361, and PF05233. Included in the database for each HMM entry is a feature which allows the user to visualize the information in the HMM.

Finally, the J. Craig Venter Institute maintains the TIGR database. The TIGR HMM profiles that describe the probable structure of phasins are TIGR01841, TIGR01985, TIGR02809 and TIGR01837.

Although the HMMs do not provide typical sequence information regarding phasin proteins, they do provide a description of the probable structure of a phasin. Thus, analogs of phasin that conform to the HMM would likely have the property of binding PHA. To easily generate sequences of phasin analogs likely to have the property of binding PHA, a skilled person could generate phasin analog sequences using a computer to introduce substitutions, deletions or additions to a phasin sequence. The relative probabilities embodied in the phasin HMMs would guide a skilled person regarding which residues, when mutated, are more likely to lead to a loss of function. The skilled person could then compare the analog sequences to the HMMs in the databases listed above. Those analogs which met the threshold of being tagged as bearing a phasin domain would likely have the property of binding PHA. The HMMs discussed above which describe phasins and phasin analogs are hereby incorporated by reference.

"Signal sequence" means a polypeptide sequence which is transported by a cell. A signal sequence may be connected to another polypeptide, and the cell will transport the signal sequence along with the polypeptide to which the signal sequence is attached. Signal sequences generally transport proteins to specific locations in the cell, or transport the protein out of from the cell. Signal sequences exist which will lead to transport of a protein to organelles, to inclusion bodies, to a membrane, to the periplasmic space, or to the extracellular medium. Signal sequences are well known in the art. A skilled person can find a signal sequence for a given organism to target a protein to a particular cellular compartment, or to target a protein for secretion. For example, the Signal sequence website maintained by Katya Kapp at the University of Heidelberg allows the skilled person to browse over 3500 known and characterized signal sequences based on species and on the region to which the signal sequence is transported. The Signal Sequence database of the Signal sequence website is hereby incorporated by reference. Since PHAs are generated by many bacteria, a sample of useful bacterial signal sequences is provided in Table 2 below.

TABLE 2

Representative Signal Sequences

| Name | Sequence | SEQ ID NO |
|---|---|---|
| HlyA | LAYGSQGDLNPLINEISKIISAAGSFDVKEERTAASLLQL SGNASDFSYGRNSITLTTSA | 8 |
| TorA | MNNNDLFQASRRRFLAQLGGLTVAGMLGPSLLTPRRA TAAQA | 9 |
| GeneIII | MKKLLFAIPLVVPFYSHS | 10 |
| PelB | MKYLLPTAAAGLLLLAAQPAMA | 11 |
| OmpA | MKKTAIAIAVALAGFATVAQA | 12 |
| OmpF | MMKRNILAVIVPALLVAGTANA | 13 |
| OmpC | MKVKVLSLLVPALLVAGAANA | 14 |
| OmpT | MRAKLLGIVLTTPIAISSFA | 15 |
| StII | MKKNIAFLLASMFVFSIATNAYA | 16 |
| PhoA | MKQSTIALALLPLLFTPVTKA | 17 |
| PhoE | MKKSTLALVVMGIVASASVQA | 18 |
| MalE | MKIKTGARILALSALTTMMFSASALA | 19 |

TABLE 2-continued

Representative Signal Sequences

| Name | Sequence | SEQ ID NO |
|---|---|---|
| Endoxylanase | MFKFKKKFLVGLTAAFMSISMFSATASA | 20 |
| Lpp | MKATKLVLGAVILGSTLLAG | 21 |
| LamB | MMITLRKLPLAVAVAAGVMSAQAMA | 22 |
| LTB | MNKVKCYVLFTALLSSLYAHG | 23 |

Figure 3:
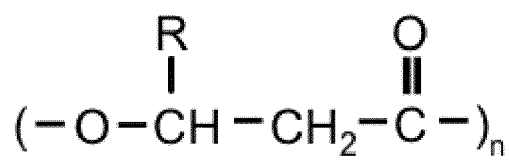
FIG. 3. Chemical structure of polyhydroxyalkanoate.

"Polyhydroxyalkanoate" (PHA) means a class of polyester accumulated by a variety of microorganisms in response to nutrient limitation or an environmental stress. The intracellular storage of these bioplastics provides a reserve of carbon, energy, and reducing power. FIG. 2 depicts a cell with PHA granules in its cytoplasm. The material properties of PHAs are similar to those of traditional petroleum-based plastics, like polypropylene, which enables their use in commercial and medical applications. Additionally, PHAs have the advantages of biodegradability and renewability, therefore providing a sustainable source of non-petrochemically-derived plastic. PHAs have the general formula as depicted in FIG. 3. A very common PHA is polyhydroxybutyrate (PHB). PHAs and PHB are discussed in detail in Reddy et al. *Polyhydroxyalkanoates: An Overview*. Bioresourse Technology 87 (2003) 137-146, which is hereby incorporated by reference.

In the context of a phasin or phasin analog interacting with a PHA, "binds to" means that the phasin or phasin analog interacts with the PHA such that if the phasin or phasin analog is transported, a measurable quantity of PHA is transported by association with the phasin or phasin analog.

"Connected" and "connecting" mean that two proteins are attached by a peptide bond or a linker.

"Linker" means between one and thirty amino acids that connect two proteins.

"Residue" means an individual amino acid at a prescribed position in a polypeptide chain. Residues may be identified by a number corresponding to the residue's ordinal position counting from the N-terminus of the polypeptide to the C-terminus.

When a promoter "drives transcription" it means that the presence of the promoter is sufficient, under one or more conditions, to cause an RNA polymerase to begin transcribing an mRNA from a polynucleotide. For example a promoter could be a constitutive promoter, which drives transcription under all conditions tested, or it could be a conditional promoter, which only drives transcription under a subset of all conditions tested.

"mRNA" means messenger RNA.

A polynucleotide or mRNA that "codes for" a polypeptide means that the polynucleotide or mRNA provides a series of nucleotide codons which may be used by a ribosome to generate a given polypeptide according to a genetic code.

A "ribosomal binding site" is a sequence in an mRNA which aids in recruiting a ribosome to the mRNA so that the mRNA may be translated. In bacteria, a ribosomal biding site often comprises a Shine-Dalgarno sequence (AGGAGG, SEQ ID NO:24), or a variant of this sequence. In eukaryotes, a ribosomal binding site often comprises a Kozak sequence. The exact sequence of the Kozak sequence varies and this variation affects the efficiency of translation of an mRNA. The skilled person can modify the Kozak consensus sequence to affect translation (see, e.g. Kozak M. *Point mutations define a sequence flanking the AUG initiator codon that modulates translation by eukaryotic ribosomes*. Cell 44 (2): 283-92, which is hereby incorporated by reference). Furthermore, in eukaryotes, a ribosomal binding site may comprise an internal ribosomal entry site (IRES).

To "translate" or "translated" means that a ribosome binds to an mRNA and generates a polypeptide that corresponds to the mRNA according to a genetic code.

"Terminator sequences" are sequences which cause an RNA polymerase to terminate transcription.

To "terminate transcription" means that an individual RNA polymerase disengages from its template polynucleotide and releases the mRNA it was generating. Sometimes, in the process of terminating transcription the 3' end of the mRNA is polyadenylated.

"Adapted for use in" means that a particular sequence is effective for its purpose in a particular species. For example, if a terminator is adapted for use in a species, then the terminator will be able to terminate transcription in that species. Likewise if a promoter is adapted for use in a species, then the promoter will drive transcription in that species. Promoters, ribosomal binding sites and terminators adapted for use in various species are known in the art.

"Cell" means a living organism belonging to the prokaryotic or eukaryotic lineage.

An "expression system" is one or more polynucleotides which can be introduced into cells to cause expression of a given set of proteins.

"PHA anabolic enzymes" are enzymes that, when expressed in a cell, will lead to accumulation of a PHA. PHA anabolic enzymes include PHA synthase (E.C. 2.3.1.-), acetyl CoA acetyltransferase (E.C. 2.3.1.9)/beta ketothiolase, and acetoacetyl-CoA reductase (E.C. 1.1.1.36). For example PhbC (SEQ ID NO:25), PhbA (SEQ ID NO:26), and PhbB (SEQ ID NO: 27) are PHA anabolic enzymes. Polynucleotides which code for these enzymes are found on the plasmid pBHR68.

"pLG575" is an expression system for the HlyB and HlyD genes. The HlyB and D genes code for proteins which aid in the export of HlyA from bacterial cells. The construction and sequence of pLG575 is described in further detail in Mackmann et al., *Genetical and functional organisation of the Escherichia coli haemolysin determinant* 2001, Mol Gen Genet (1985) 201:28-288, which is incorporated by reference.

"pBHR68" is an expression plasmid which expresses the PhbC PhbA and PhbB genes in *E. Coli*. The construction and sequence of this plasmid is described in further detail in Spikermann et al., *A sensitive, viable-colony staining method using Nile red for direct screening of bacteria that accumu-*

*late polyhydroxyalkanoic acids and other lipid storage compounds*, Arch Microbiol (1999) 171:73-80, which is incorporated by reference.

"pBHR68:PhaP1:HlyA" is the expression plasmid pBHR68 also containing an polynucleotide for expression of SEQ ID NO:1 connected to SEQ ID NO:8.

To "transport" or "transporting" means that a molecule is removed from one location to another. For example, a PHA could be transported from a granule to the periplasmic space, to an inclusion body, or it could be secreted. If eukaryotes generating PHA were provided the PHA could additionally be transported to an organelle. Transport of proteins is generally directed by signal sequences.

To "secrete" or "secretion" means transporting the secreted molecule from inside a cell to the outside of the cell.

To "express" or "expression" means that a cell is producing a polypeptide according to the information provided to the cell in a polynucleotide.

To "transform" or "transforming" means to introduce a polynucleotide into a cell by chemical, electrical or physical means. Methods of transforming cells include chemical destabilization of the cell membrane to allow the polynucleotide to enter, electroporation, microinjection, or firing particles coated with the polypeptide into the cell.

To "make available" a polypeptide or a polynucleotide to a cell means that the polypeptide or polynucleotide is introduced into the cell. Methods of introduction include transformation, genetic techniques, and conjugation between bacterial cells.

In the context of bioplastic production "collecting" a bioplastic means removing the bioplastic from the vessel in which bioplastic production occurred. "Collecting" does not necessitate purification of the bioplastic from the organism in which the bioplastic was synthesized.

"B0034" means the synthetic biology construct identified by "B0034" in the Registry of Standard Biological Parts maintained by Massachusetts Institute of Technology.

"B0015" means the synthetic biology construct identified by "B0015" in the Registry of Standard Biological Parts maintained by Massachusetts Institute of Technology.

"R0010" means the synthetic biology construct identified by "R0010" in the Registry of Standard Biological Parts maintained by Massachusetts Institute of Technology.

"R0011" means the synthetic biology construct identified by "R0011" in the Registry of Standard Biological Parts maintained by Massachusetts Institute of Technology.

"R0040" means the synthetic biology construct identified by "R0040" in the Registry of Standard Biological Parts maintained by Massachusetts Institute of Technology.

"R0051" means the synthetic biology construct identified by "R0051" in the Registry of Standard Biological Parts maintained by Massachusetts Institute of Technology.

Chimeric Polypeptides

One aspect of the invention includes chimeric polypeptides which can be used to transport PHAs. In a general sense, the chimeric polypeptide comprises a phasin or a phasin analog which binds to a PHA connected to a signal sequence. The signal sequence may be connected to the N- or C-terminus of the phasin or phasin analog, as appropriate. Many signal sequences are well characterized and the literature directed to a particular signal sequence will apprise the skilled person whether there is a preference for the signal sequence to be connected at the N- or C-terminus of the phasin or phasin analog.

The signal sequence may be connected by a peptide bond or by a linker of between one and thirty amino acids. Linkers are commonly used in the art, they provide a spacer between the signal sequence and the phasin or phasin analog.

The signal sequence used can be any signal sequence appropriate for the organism in which contains a PHA of interest. Since bacteria synthesize PHAs, bacterial signal sequences are useful. Any bacterial signal sequence may be used. Any of the 1161 confirmed bacterial signal sequences in the Signal sequence Website:

Signal Sequence Database may be used. In some embodiments of the invention, the signal sequence will comprise SEQ ID NO:8, 9, 10, 11, 12, 13, 14, 15, 16, 17, 18, 19, 20, 21, 22, or 23. In a separate embodiment, the signal sequence will comprise SEQ ID NO: 8, 9, 10, 11, or 12.

If a phasin is chosen for the chimeric polypeptide, the phasin chosen may be any characterized phasin. The phasin family of proteins is well characterized and the sequences of these proteins are viewable in publicly available databases. For example, the search "phasin" in the Entrez-Protein database returns 2125 entries Furthermore, the same search in the Entrez-Gene database returns 639 entries. In some embodiments, the phasin may be one of SEQ ID NO:1-7 or 29-121. In a particular embodiment, the phasin used is SEQ ID NO:1. In another particular embodiment, SEQ ID NO:1 is connected to a signal sequence chosen from the following: SEQ ID NO:8, 9, 10, 11, 12, 13, 14, 15, 16, 17, 18, 19, 20, 21, 22, or 23. In another embodiment, the chimeric polypeptide comprises SEQ ID NO:1 connected to a signal sequence chosen from the following: SEQ ID NO:8, 9, 10, 11, or 12. In another embodiment, the chimeric polypeptide comprises SEQ ID NO:1 and SEQ ID NO:8.

If a phasin analog is chosen for the chimeric polypeptide, the phasin analog should be chosen so as to bind a PHA as described above. In a particular embodiment, the phasin analog comprises a phasin sequence with one or more residue additions, substitutions, or deletions, wherein the analog meets the default threshold to be marked as bearing a phasin domain by a phasin Hidden Markov Model.

Polynucleotides

Another aspect of the invention includes polynucleotides which code for the chimeric polypeptides disclosed. In a general sense, the polynucleotides disclosed comprise a sequence which codes for a chimeric polypeptide, the chimeric polypeptide comprising a phasin or a phasin analog which binds to a PHA, and a signal sequence. This polynucleotide may be introduced into a cell in order to cause transcription of the chimeric polypeptide and subsequent transport of the PHA. The polynucleotide may be provided with a promoter 5' of the sequence which codes for the chimeric protein, or the polynucleotide may be inserted into the genome in such a way that the polynucleotide is transcribed by a promoter native to the cell. Likewise, a ribosomal binding site and terminator sequences may be introduced, or native sequences can be used as well.

The promoter, ribosomal binding site and terminator sequences should be adapted for use in an appropriate cell. In one embodiment, the promoter, ribosomal binding site and terminator sequences are adapted for use in a prokaryotic cell. In another embodiment, the promoter, ribosomal binding site and terminator sequences are adapted for use in a bacterial cell. In another embodiment, the promoter, ribosomal binding site and terminator sequences are adapted for use in a gram-negative bacterial cell. In another embodiment, the promoter, ribosomal binding site and terminator sequences are adapted for use in an *E. coli* cell. In a particular embodiment, the promoter comprises one of: the Lac promoter, the TetR promoter, the LacpL Hybrid promoter or the Lambda pl Regulated Promoter. These are well characterized promoters that are commonly used in the art to drive transcription in bacteria. In another embodiment, the ribosomal binding site comprises B0034. In another embodiment, the terminator sequence or sequences comprise B0015.

In another embodiment, the polynucleotide comprises a sequence which codes for any signal sequence appropriate for the organism in which contains a PHA of interest. Since bacteria synthesize PHAs, bacterial signal sequences are useful. Any of the 1161 confirmed bacterial signal sequences in the Signal sequence Website: Signal Sequence Database may be used. In some embodiments of the invention, the signal sequence will comprise SEQ ID NO:8, 9, 10, 11, 12, 13, 14, 15, 16, 17, 18, 19, 20, 21, 22, or 23. In a separate embodiment, the signal sequence will comprise SEQ ID NO: 8, 8, 10, 11, or 12.

If a phasin is chosen for the chimeric polypeptide, the polynucleotide should comprise a sequence which codes for any characterized phasin. In one embodiment, the phasin may be one of SEQ ID NO:1-7 or 29-121. In a particular embodiment, the phasin used is SEQ ID NO:1. In another particular embodiment, SEQ ID NO:1 is connected to a signal sequence chosen from the following: SEQ ID NO:8, 9, 10, 11, 12, 13, 14, 15, 16, 17, 18, 19, 20, 21, 22, or 23. In another embodiment, the chimeric polypeptide comprises SEQ ID NO:1 connected to a signal sequence chosen from the following: SEQ ID NO:8, 9, 10, 11, or 12. In another embodiment, the chimeric polypeptide comprises SEQ ID NO:1 and SEQ ID NO:8.

If a phasin analog is chosen for the chimeric polypeptide, the polynucleotide should comprise a sequence that codes for a phasin analog that will bind a PHA as described above. In a particular embodiment, the phasin analog comprises a phasin sequence with one or more residue additions, substitutions, or deletions, wherein the analog meets the default threshold to be marked as bearing a phasin domain by a phasin Hidden Markov Model.

In another embodiment, the polynucleotide comprises PBHR68:PhaP1:HlyA.

Cells

Another aspect of the invention includes cells which may be used to transport PHAs. The cell may be any cell chosen from among eukaryotes and prokaryotes. In one embodiment, the cell is any prokaryotic cell. In another embodiment, the cell is a bacterial cell. In another embodiment, the cell is a gram-negative bacterial cell. In another embodiment, the cell is an E. coli cell. This aspect of the invention contemplates that any of these listed cells may harbor any appropriate chimeric protein or polynucleotide disclosed above. A chimeric protein or polynucleotide will be considered appropriate for a cell if the signal sequence chosen will be transported by that cell and any additional sequences used, such as promoters, ribosomal binding sites and terminators, are adapted for use in that cell.

In another embodiment, the cells further comprise an expression system for PHA anabolic enzymes. In one embodiment, the expression system comprises SEQ ID NO: 25, SEQ ID NO: 26 and SEQ ID NO:27. In another embodiment, the expression system comprises pBHR68.

In another embodiment, the cell comprises the plasmid pBHR68, and the sequences SEQ ID NO:1 and SEQ ID NO:8. In another embodiment, the cell comprises pBHR68: PhaP1:HlyA. In another embodiment, the cell comprises HlyB and HlyD. In another embodiment, the cell may comprise pLG575.

Methods for Transporting PHAs

Another aspect of the invention includes methods for transporting PHAs. In a general sense, the methods comprise providing a chimeric polypeptide to the cell, the chimeric polypeptide comprising a phasin or phasin analog which binds to a PHA, and a signal sequence.

In one embodiment, providing the chimeric polypeptide to the cell is performed by introducing a polynucleotide into the cell, the polynucleotide comprising a sequence which codes for the chimeric polypeptide. Many methods for introducing polynucleotides into the cell are well known and characterized in the art. A skilled person may use chemical transformation, electroporation, gene gun technologies, microinjection, genetic recombination, or conjugation. The polynucleotide may be introduced in such a way that the polynucleotide inserts into the genome and replaces an existing gene. In this embodiment, the promoter, ribosomal binding site, and terminator sequences of the native gene may now cause expression of the chimeric polypeptide. In another embodiment, the polynucleotide is provided with a promoter, ribosomal binding site and terminator sequences. Further discussion of these well known techniques used to introduce polynucleotides into cells and to express genes in cells may be found in Joe Sambrook, *Molecular Cloning: A Laboratory Manual, Third Edition*, Cold Spring Harbor Laboratory Press, 2001 (ISBN: 0879695773); or in Frederick M. Ausubel, et al., eds., *Current Protocols in Molecular Biology*, Wiley (ISSN: 1934-3639, last updated Jun. 28, 2010).

In one embodiment, the polynucleotide provided to the cell comprises a promoter 5' of the sequence which codes for the chimeric protein. In another embodiment, the polynucleotide provided comprises a ribosomal binding site and terminator sequences.

The promoter, ribosomal binding site and terminator sequences should be adapted for use in an appropriate cell. In one embodiment, the promoter, ribosomal binding site and terminator sequences are adapted for use in a prokaryotic cell. In another embodiment, the promoter, ribosomal binding site and terminator sequences are adapted for use in a bacterial cell. In another embodiment, the promoter, ribosomal binding site and terminator sequences are adapted for use in a gram-negative bacterial cell. In another embodiment, the promoter, ribosomal binding site and terminator sequences are adapted for use in an E. coli cell. In a particular embodiment, the promoter comprises one of: the Lac promoter, the TetR promoter, the LacpL Hybrid promoter or the Lambda pl Regulated Promoter. These are well characterized promoters that are commonly used in the art to drive transcription in bacteria. In another embodiment, the ribosomal binding site comprises B0034. In another embodiment, the terminator sequence or sequences comprise B0015.

In another embodiment, the polynucleotide provided comprises a sequence which codes for any signal sequence appropriate for the organism in which contains a PHA of interest. Since bacteria synthesize PHAs, bacterial signal sequences are useful. Any of the 1161 confirmed bacterial signal sequences in the Signal sequence Website: Signal Sequence Database may be used. In some embodiments of the invention, the signal sequence will comprise SEQ ID NO:8, 9, 10, 11, 12, 13, 14, 15, 16, 17, 18, 19, 20, 21, 22, or 23. In a separate embodiment, the signal sequence will comprise SEQ ID NO: 8, 8, 10, 11, or 12.

In one embodiment, the polynucleotide provided to the cell may comprise a sequence which codes for any characterized phasin. In one embodiment, the phasin may be one of SEQ ID NO:1-7 or 29-121. In a particular embodiment, the phasin used is SEQ ID NO:1. In another particular embodiment, SEQ ID NO:1 is connected to a signal sequence chosen from the following: SEQ ID NO:8, 9, 10, 11, 12, 13, 14, 15, 16, 17, 18, 19, 20, 21, 22, or 23.

In another embodiment, the polynucleotide provided codes for a chimeric polypeptide comprising SEQ ID NO:1 connected to a signal sequence chosen from the following: SEQ ID NO:8, 9, 10, 11, or 12. In another embodiment, the polynucleotide provided codes for a chimeric polypeptide comprising SEQ ID NO:1 and SEQ ID NO:8.

If the polynucleotide codes for a chimeric polypeptide comprising a phasin analog, the polynucleotide should comprise a sequence that codes for a phasin analog that will bind a PHA as described above. In a particular embodiment, the phasin analog comprises a phasin sequence with one or more residue additions, substitutions, or deletions, wherein the analog meets the default threshold to be marked as bearing a phasin domain by a phasin Hidden Markov Model.

In another embodiment, the polynucleotide provided comprises PBHR68:PhaP1:HlyA.

In another embodiment, the polynucleotide may be provided to any appropriate cell, including a prokaryote, a bacterium, a gram-negative bacterium, or an *E. coli* cell. In another embodiment, the cell is provided with HlyB and HlyD. In another embodiment, the cell is provided with pLG575. In another embodiment, the cell may be provided with an expression system for PHA anabolic enzymes. In one embodiment, the expression system comprises SEQ ID NO:25, 26, and 27. In another embodiment, the expression system comprises pBHR68. In another embodiment, pBHR68:PahP1:HlyA is provided to the cell. In another embodiment, providing the polynucleotide to the cell causes the PHA to be transported outside the cell. In another embodiment, providing the polynucleotide to the cell causes the PHA to be transported to the periplasmic space.

In another embodiment, the cells are kept in continuous culture.

Methods for Producing a Bioplastic

Another aspect of the invention includes methods for producing a bioplastic. In a general sense, the methods comprise providing a cell which produces one or more PHAs, providing a chimeric polypeptide to the cell, the chimeric polypeptide comprising a phasin or phasin analog which binds to a PHA, and a signal sequence, and collecting a PHA which has been transported by association with the chimeric polypeptide.

In one embodiment, providing the chimeric polypeptide to the cell is performed by introducing a polynucleotide into the cell, the polynucleotide comprising a sequence which codes for the chimeric polypeptide.

In one embodiment, the polynucleotide provided to the cell comprises a promoter 5' of the sequence which codes for the chimeric protein. In another embodiment, the polynucleotide provided comprises a ribosomal binding site and terminator sequences.

The promoter, ribosomal binding site and terminator sequences should be adapted for use in an appropriate cell. In one embodiment, the promoter, ribosomal binding site and terminator sequences are adapted for use in a prokaryotic cell. In another embodiment, the promoter, ribosomal binding site and terminator sequences are adapted for use in a bacterial cell. In another embodiment, the promoter, ribosomal binding site and terminator sequences are adapted for use in a gram-negative bacterial cell. In another embodiment, the promoter, ribosomal binding site and terminator sequences are adapted for use in an *E. coli* cell. In a particular embodiment, the promoter comprises one of: the Lac promoter, the TetR promoter, the LacpL Hybrid promoter or the Lambda pl Regulated Promoter. These are well characterized promoters that are commonly used in the art to drive transcription in bacteria.

In another embodiment, the ribosomal binding site comprises B0034. In another embodiment, the terminator sequence or sequences comprise B0015.

In another embodiment, the polynucleotide provided comprises a sequence which codes for any signal sequence appropriate for the organism in which contains a PHA of interest. Since bacteria synthesize PHAs, bacterial signal sequences are useful. Any of the 1161 confirmed bacterial signal sequences in the Signal sequence Website: Signal Sequence Database may be used. In some embodiments of the invention, the signal sequence will comprise SEQ ID NO:8, 9, 10, 11, 12, 13, 14, 15, 16, 17, 18, 19, 20, 21, 22, or 23. In a separate embodiment, the signal sequence will comprise SEQ ID NO: 8, 8, 10, 11, or 12.

In one embodiment, the polynucleotide provided to the cell may comprise a sequence which codes for any characterized phasin. In one embodiment, the phasin may be one of SEQ ID NO:1-7 or 29-121. In a particular embodiment, the phasin used is SEQ ID NO:1. In another particular embodiment, SEQ ID NO:1 is connected to a signal sequence chosen from the following: SEQ ID NO:8, 9, 10, 11, 12, 13, 14, 15, 16, 17, 18, 19, 20, 21, 22, or 23.

In another embodiment, the polynucleotide provided codes for a chimeric polypeptide comprising SEQ ID NO:1 connected to a signal sequence chosen from the following: SEQ ID NO:8, 9, 10, 11, or 12. In another embodiment, the polynucleotide provided codes for a chimeric polypeptide comprising SEQ ID NO:1 and SEQ ID NO:8.

If the polynucleotide codes for a chimeric polypeptide comprising a phasin analog, the polynucleotide should comprise a sequence that codes for a phasin analog that will bind a PHA as described above. In a particular embodiment, the phasin analog comprises a phasin sequence with one or more residue additions, substitutions, or deletions, wherein the analog meets the default threshold to be marked as bearing a phasin domain by a phasin Hidden Markov Model.

In another embodiment of a method, the polynucleotide provided comprises PBHR68:PhaP1:HlyA.

In another embodiment, the polynucleotide may be provided to any appropriate cell, including a prokaryote, a bacterium, a gram-negative bacterium, or an *E. coli* cell. In another embodiment, the cell is provided with HlyB and HlyD. In another embodiment, the cell is provided with pLG575. In another embodiment, the cell may be provided with an expression system for PHA anabolic enzymes. In one embodiment, the expression system comprises SEQ ID NO:25, 26, and 27. In another embodiment, the expression system comprises pBHR68. In another embodiment, pBHR68:PahP1:HlyA is provided to the cell. In another embodiment, providing the polynucleotide to the cell causes the PHA to be transported outside the cell. In another embodiment, providing the polynucleotide to the cell causes the PHA to be transported to the periplasmic space.

In another embodiment, collecting the PHA comprises collecting the media in which the cells are grown. In another embodiment, collecting the PHA comprises centrifuging the cells from the media in which they are grown and concentrating the supernatant.

In another embodiment, the cells are kept in continuous culture.

For all of the preceding chimeric polypeptides, polynucleotides, cells, and methods, the PHA to be transported may comprise polyhydroxybutyrate (PHB).

It will be obvious to those having skill in the art that many changes may be made to the details of the above-described embodiments without departing from the underlying principles of the invention. The scope of the present invention should, therefore, be determined only by the following claims.

EXAMPLES

Example 1

Plasmids for Chimeric Polypeptide Production

Figure 4A:
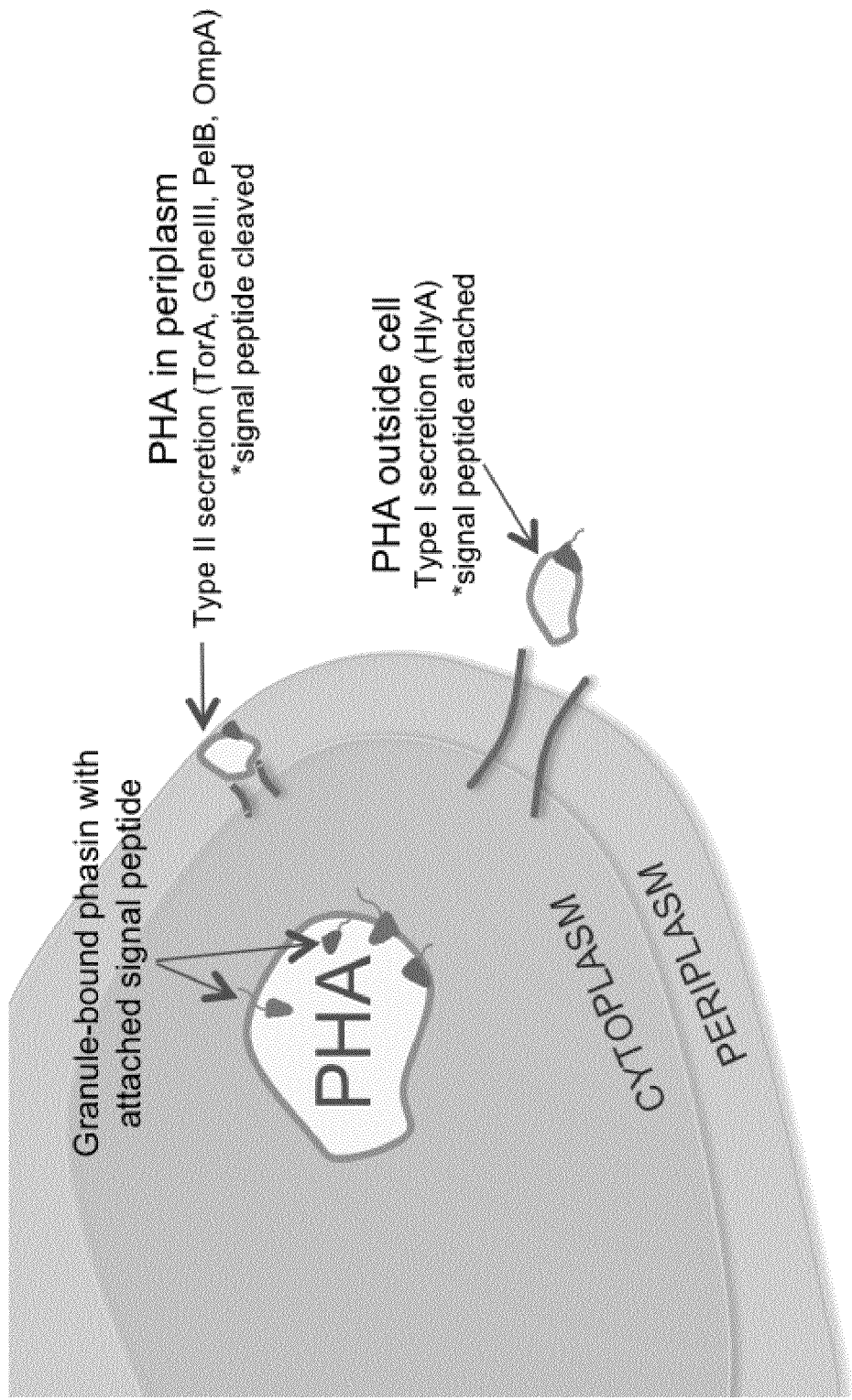
FIG. 4A. Schematic of the expected transport of PHA based on the signal sequence that is attached to a phasin or phasin analog.
Figure 4B:
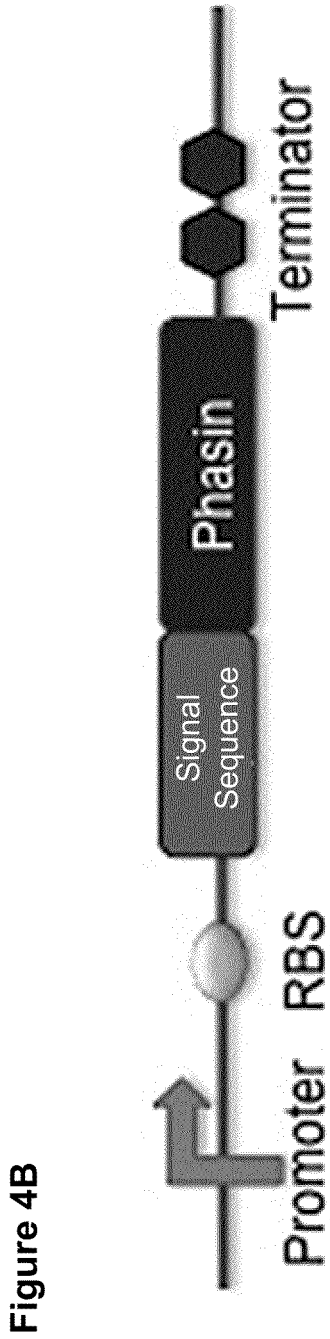
FIG. 4B. Schematic of one plasmid-based strategy to generate chimeric polypeptides.

Vectors capable of expressing a chimeric protein were designed. A general schematic of the overall expression construct organization is given in FIG. 4B. A promoter drives expression of a phasin gene connected to the DNA coding for a signal sequence. In FIG. 4B, the DNA coding for the signal sequence is 5' of the phasin gene, but the DNA coding for the signal sequence may also be 3' of the phasin gene, where the signal sequence used should be C-terminal of the phasin in the chimeric polypeptide (e.g. FIG. 5E). Furthermore, a ribosomal binding site and a terminator are included to ensure proper expression.

FIG. 5 shows the various plasmids that were designed. FIG. 5A shows plasmids having a kanamycin bacterial marker gene to select for the presence of the plasmid with kanamycin. The signal sequence used is the bacterial OmpA (SEQ ID NO:12) signal sequence, and it is connected to a phasin. Several examples are provided using the 4 different promoters R0010, R0011, R0051, and R0040. Furthermore the ribosomal binding site B0034 and the terminator B0015 were used.

Figure 5A:
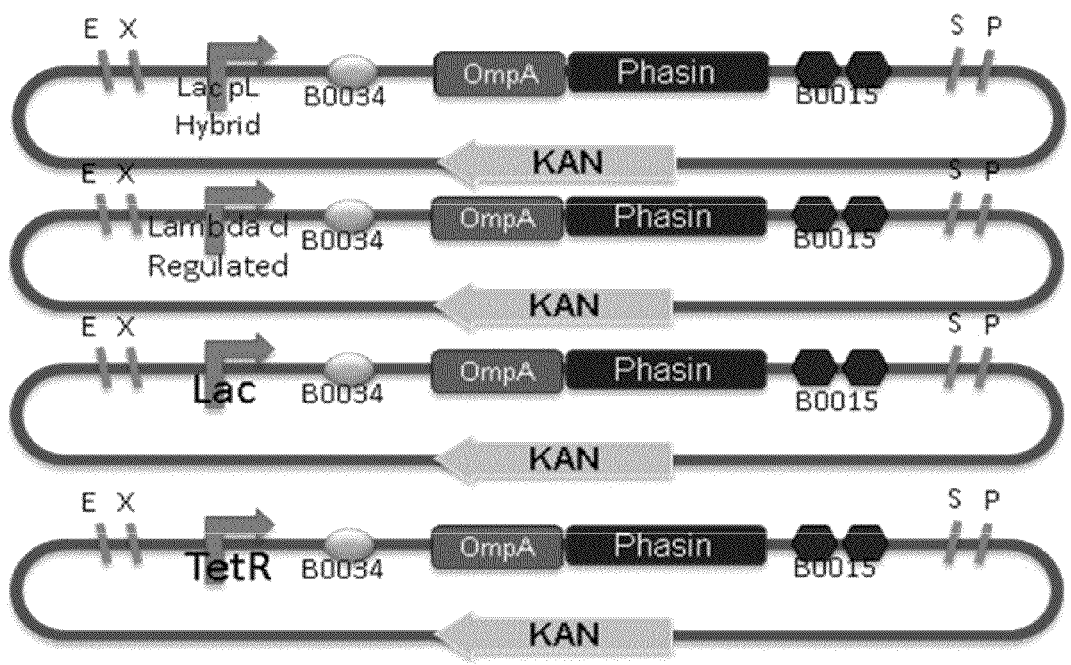
FIG. 5A. Phasin expression constructs with OmpA signal sequence and four different promoter sequences.
Figure 5B:
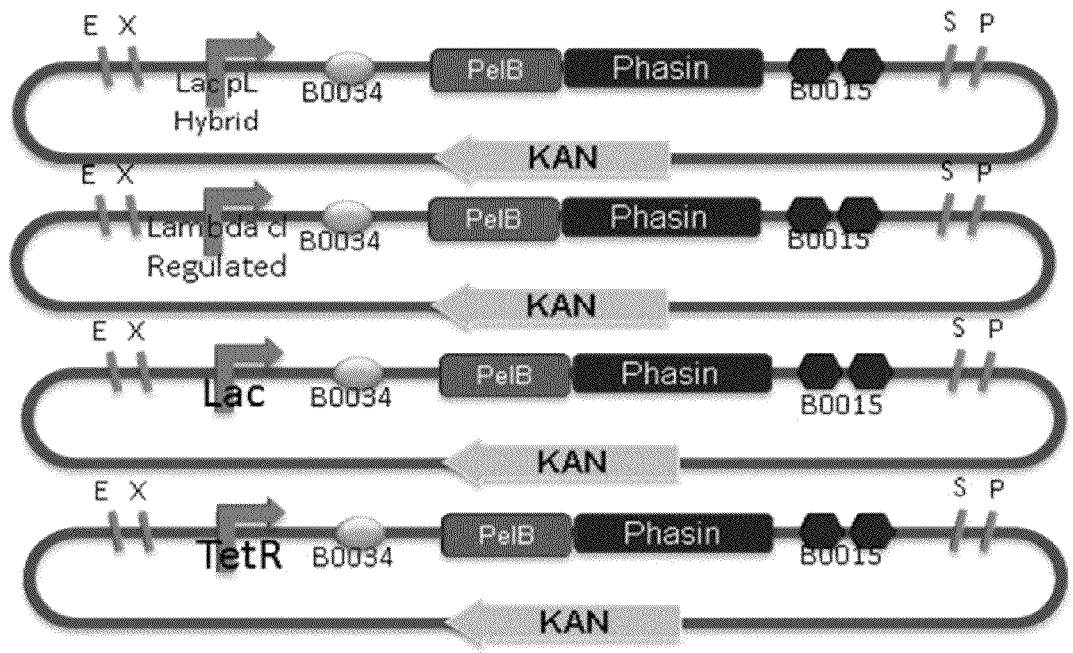
FIG. 5B. Phasin expression constructs with PelB signal sequence and four different promoter sequences.

FIG. 5B shows plasmids having a kanamycin bacterial marker gene to select for the presence of the plasmid with kanamycin. The signal sequence used is the bacterial PelB (SEQ ID NO:11) signal sequence, and it is connected to a phasin. Several examples are provided using 4 different promoters. Several examples are provided using the 4 different promoters R0010, R0011, R0051, and R0040. Furthermore the ribosomal binding site B0034 and the terminator B0015 were used.

Figure 5C:
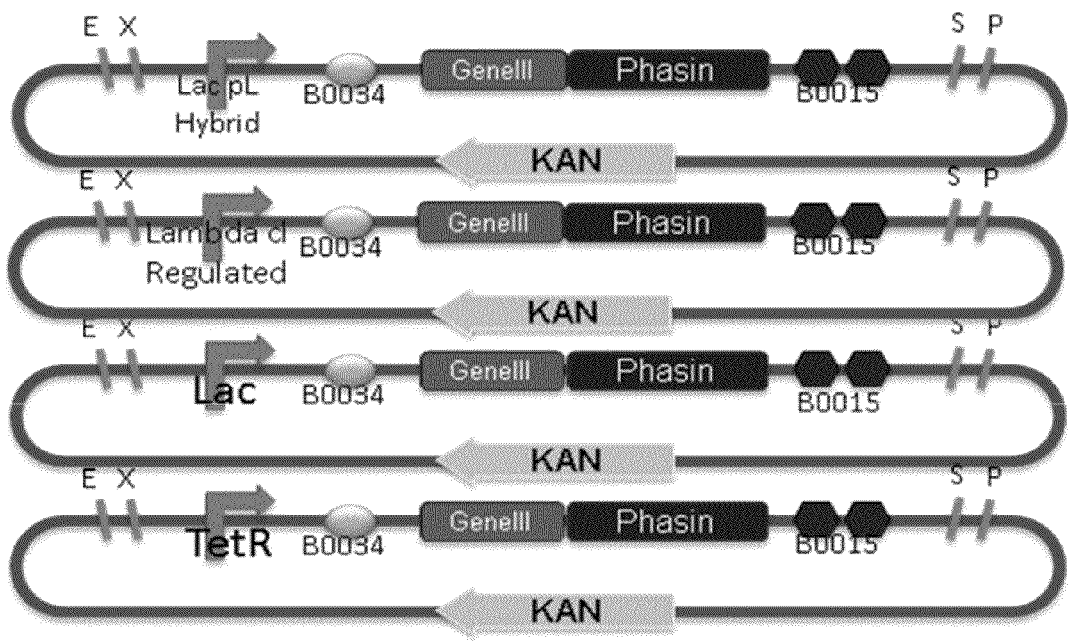
FIG. 5C. Phasin expression constructs with GeneIII signal sequence and four different promoter sequences.

FIG. 5C shows plasmids having a kanamycin bacterial marker gene to select for the presence of the plasmid with kanamycin. The signal sequence used is the bacterial GeneIII (SEQ ID NO:10) signal sequence, and it is connected to a phasin. Several examples are provided using 4 different promoters. Several examples are provided using the 4 different promoters R0010, R0011, R0051, and R0040. Furthermore the ribosomal binding site B0034 and the terminator B0015 were used.

Figure 5D:
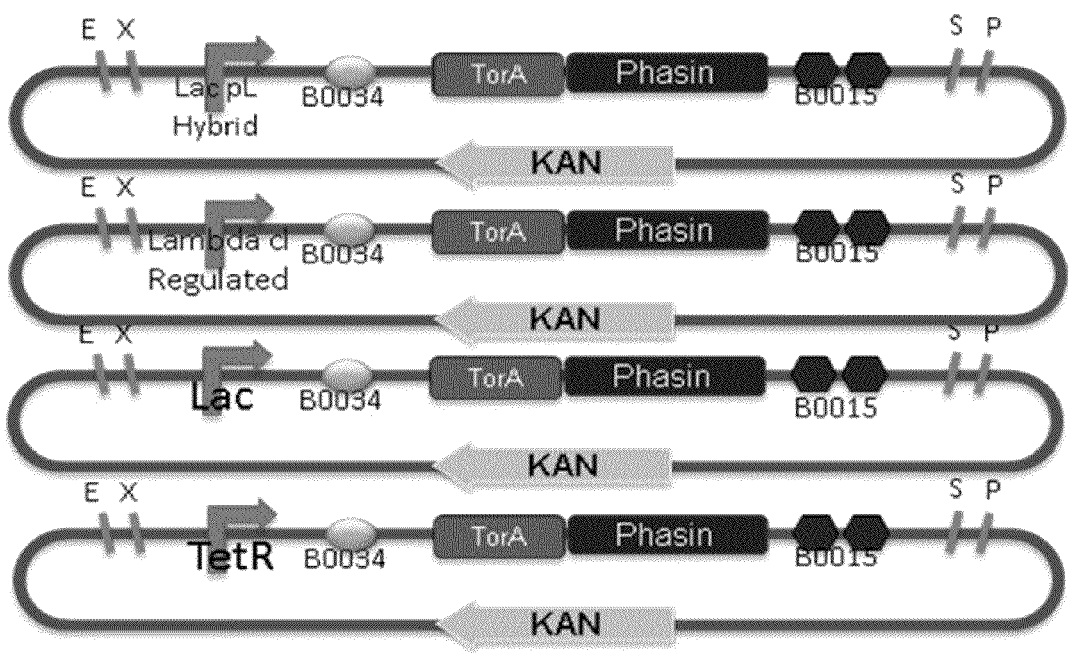
FIG. 5D. Phasin expression constructs with TorA signal sequence and four different promoter sequences.

FIG. 5D shows plasmids having a kanamycin bacterial marker gene to select for the presence of the plasmid with kanamycin. The signal sequence used is the bacterial TorA (SEQ ID NO:9) signal sequence, and it is connected to a phasin. Several examples are provided using 4 different promoters. Several examples are provided using the 4 different promoters R0010, R0011, R0051, and R0040. Furthermore the ribosomal binding site B0034 and the terminator B0015 were used.

Figure 5E:
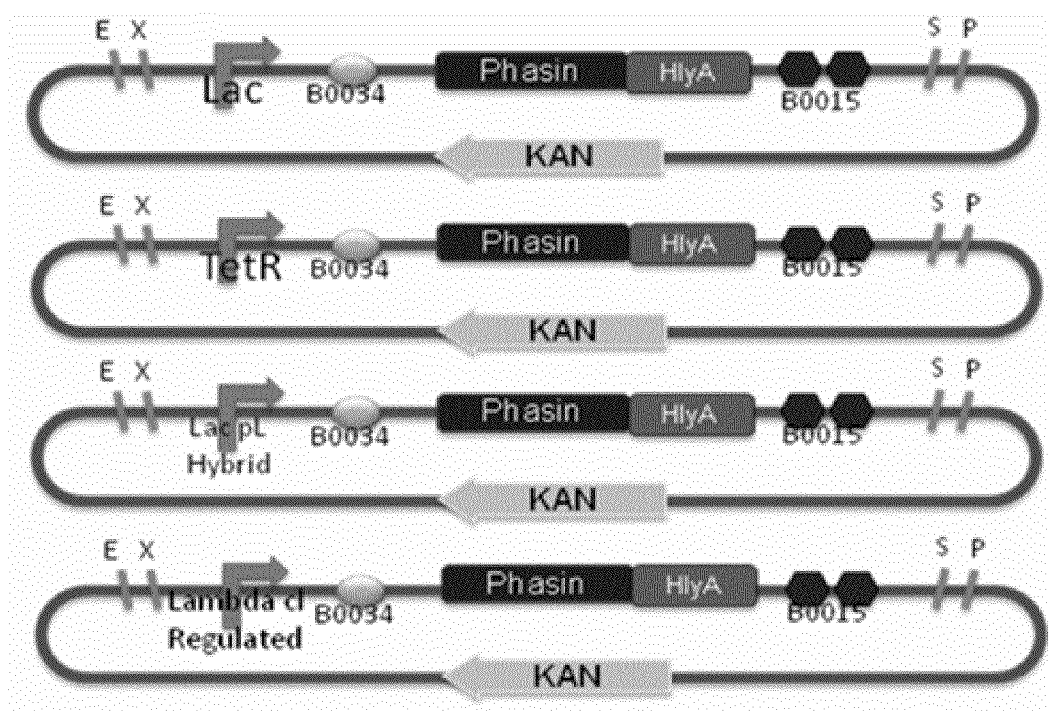
FIG. 5E. Phasin expression constructs with HlyA signal sequence and four different promoter sequences.

FIG. 5E shows plasmids having a kanamycin bacterial marker gene to select for the presence of the plasmid with kanamycin. The signal sequence used is the bacterial HlyA (SEQ ID NO:8) signal sequence, and it is connected to a phasin. Several examples are provided using 4 different promoters. Several examples are provided using the 4 different promoters R0010, R0011, R0051, and R0040. Furthermore the ribosomal binding site B0034 and the terminator B0015 were used.

To facilitate assembly of different polynucleotides, a PstI restriction enzyme site was removed from the phasin coding polynucleotide sequence by site-directed mutagenesis (FIG. 6). A QuikChangeII mutagenesis kit (Stratagene, Calif.) was used to produce a point mutation of the nucleotide at position 114 from a G to a T (SEQ ID NO:28). Site-directed mutagenesis using this kit consists of three basic steps. In the first step, primers are designed using the QuikChange® Primer Design Program (Stratagene) and used to create a mutagenic product. Next, methylated and hemimethylated DNA is digested by the addition of DpnI. Lastly, the competent cells are transformed with the mutagenic product. The sequence alteration produced by this method removed the PstI site, but did not alter the corresponding amino acid sequence.

Example 2

Initial Confirmation of Signal Sequence Function

Figure 7:
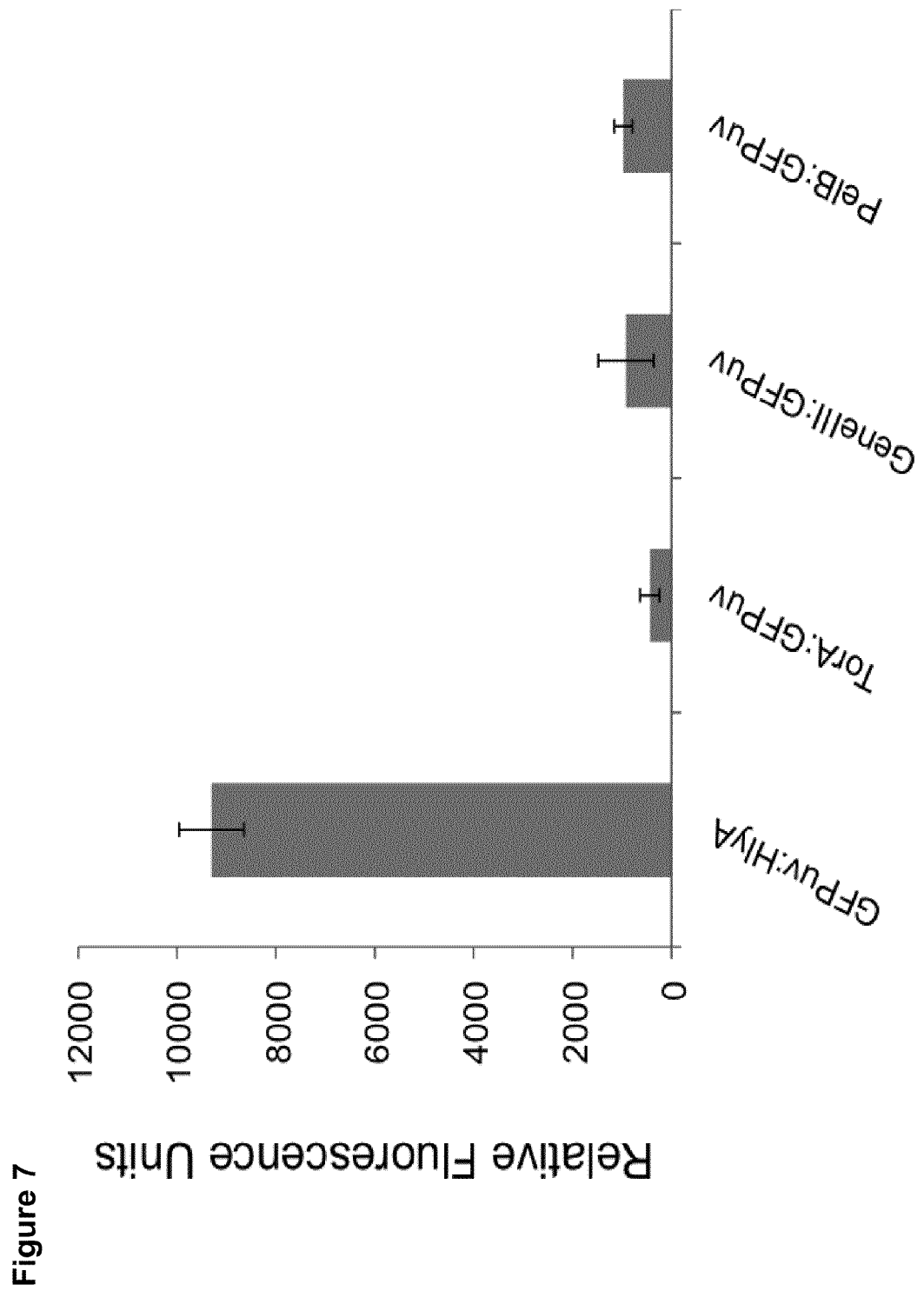
FIG. 7. Measurement of fluorescence in concentrated extracellular media. Cell free media from *E. coli* bearing the indicated constructs was tested for GFP fluorescence.

To initially confirm the function of several secretions signals, HlyA, TorA, GeneIII and PelB signal sequences (SEQ ID NO:8-11, Table 1) were fused to green fluorescent protein. Fluorescence intensity was then measured in concentrated media samples for each of the signal sequence/GFP devices. Fluorescence was also measured in pSB1A3 (no coding region) supernatant samples and subtracted from each replicate to obtain final fluorescence values. The averages and standard deviations were calculated (FIG. 7). Detected fluorescence in the GFPuv:HlyA supernatant samples was significantly higher than that measured for other signal sequence devices, thereby demonstrating GFP secretion by the presence of a significant amount of HlyA-targeted GFP in the extracellular medium. Targeting GFP with TorA, GeneIII, and PelB signal sequences resulted in lesser GFP activity in the media, as expected because these signal sequences signal protein transport to the periplasmic space, or to the membrane.

Example 3

Analysis of Transport of Chimeric Polypeptides

Figure 8:
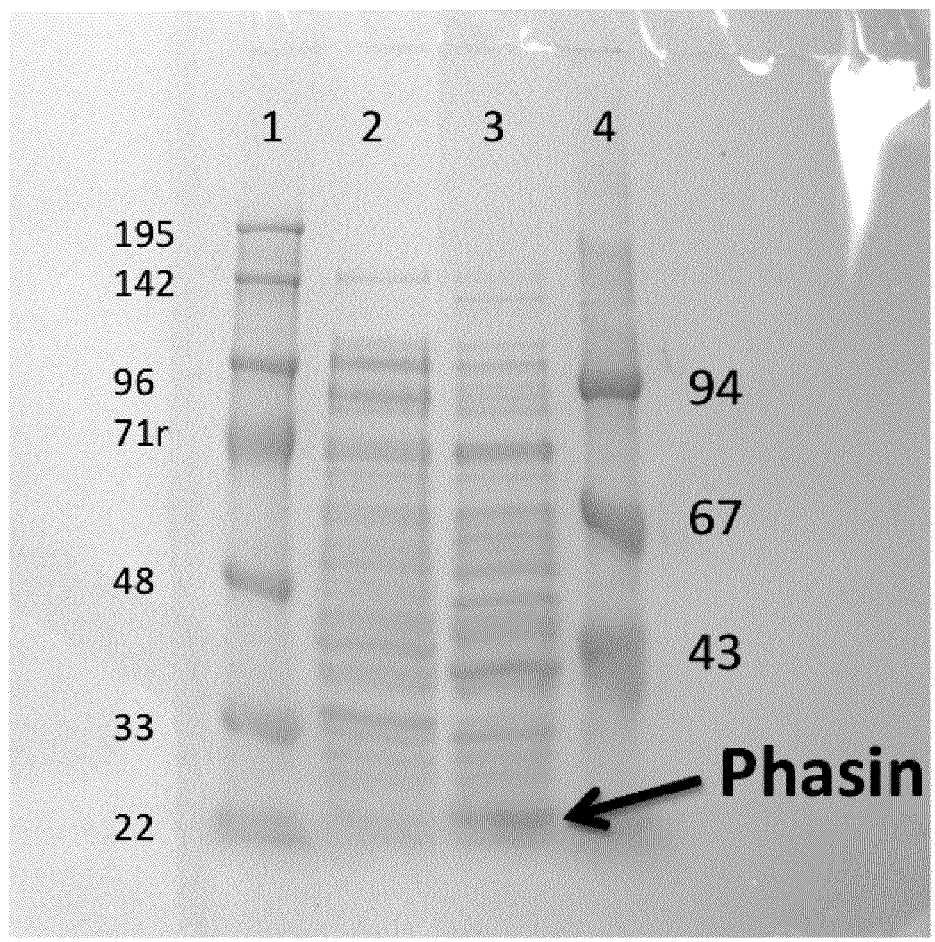
FIG. 8. Coomassie Blue Stained PAGE of Supernatant Proteins. Lane 1, molecular mass markers; lane 2, supernatant proteins from *E. coli* control without phasin secretion plasmid; lane 3, supernatant proteins from *E. coli* containing phasin secretion plasmid; lane 4, molecular mass markers.

The GeneIII signal sequence fused to the phasin protein was expressed in E. coli cells. The E. coli cells were grown overnight in LB growth media and centrifuged to pellet the cells. Supernatants (5 ml) were then concentrated using a Centricon Centriplus concentrator (Amicon, Beverly Mass.). This process concentrated proteins that were larger than 10 kDa and removed molecules smaller than 10 kDa. Approximately 20 ug of protein were then applied to a SDS polyacrylamide gel to separate the proteins according to size (FIG. 8). The gel was then stained with coomassie blue for protein detection.

After SDS polyacrylamide gel electrophoresis (PAGE) and subsequent coomassie blue staining of the separated proteins, a protein with an approximate size of 22 kDa is observed in the sample from the phasin-expressing E. coli cells that is not present in the control E. coli sample. The phasin protein has been reported by others to migrate on SDS PAGE from 20-27 kDa. These results indicate that the signal sequence peptide:: phasin expression constructs can be produced by the E. coli cells and is being secreted outside the cell into the media.

Figure 9:
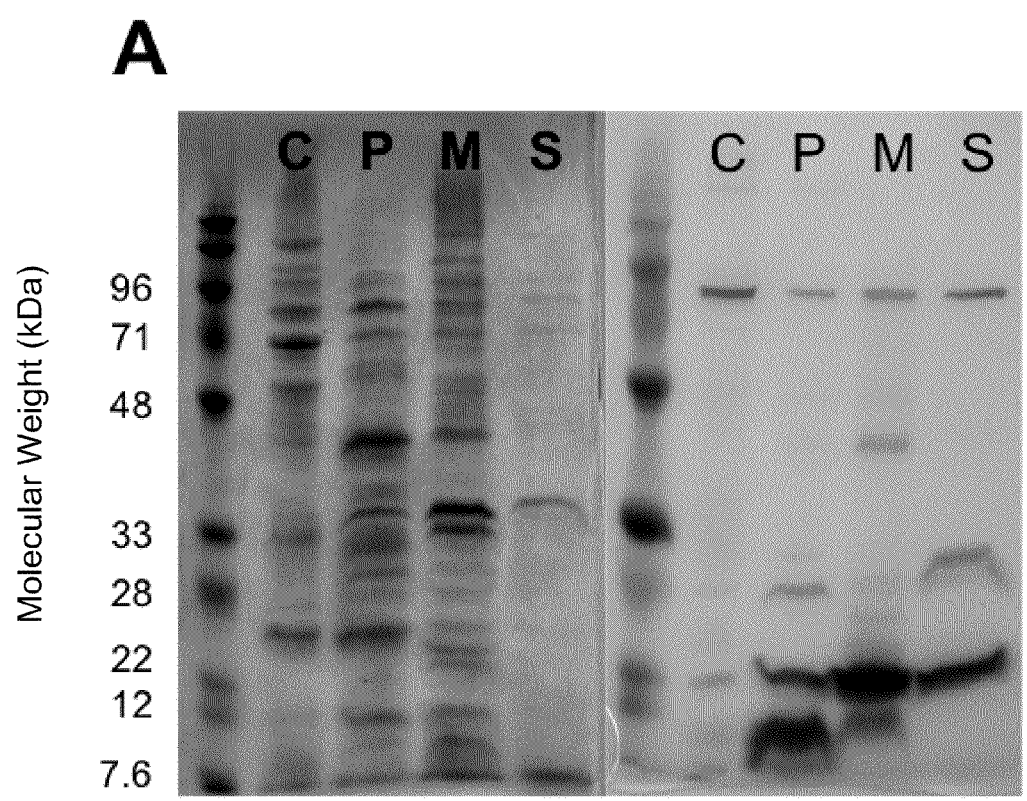
FIG. 9. SDS polyacrylamide gels and corresponding immunoblots of subcellular fractions for (A) PhaP1:HlyA, (B) TorA:PhaP1, (C) GeneIII:PhaP1, and (D) PelB:PhaP1. C—cytoplasmic fraction, P—periplasmic fraction, M—membrane fraction, S—concentrated supernatant (media) fraction. The position of GFP bands varies from roughly 22-27 kDa, and this size discrepancy between bands is a result of fusion with signal sequences.
Figure 9:
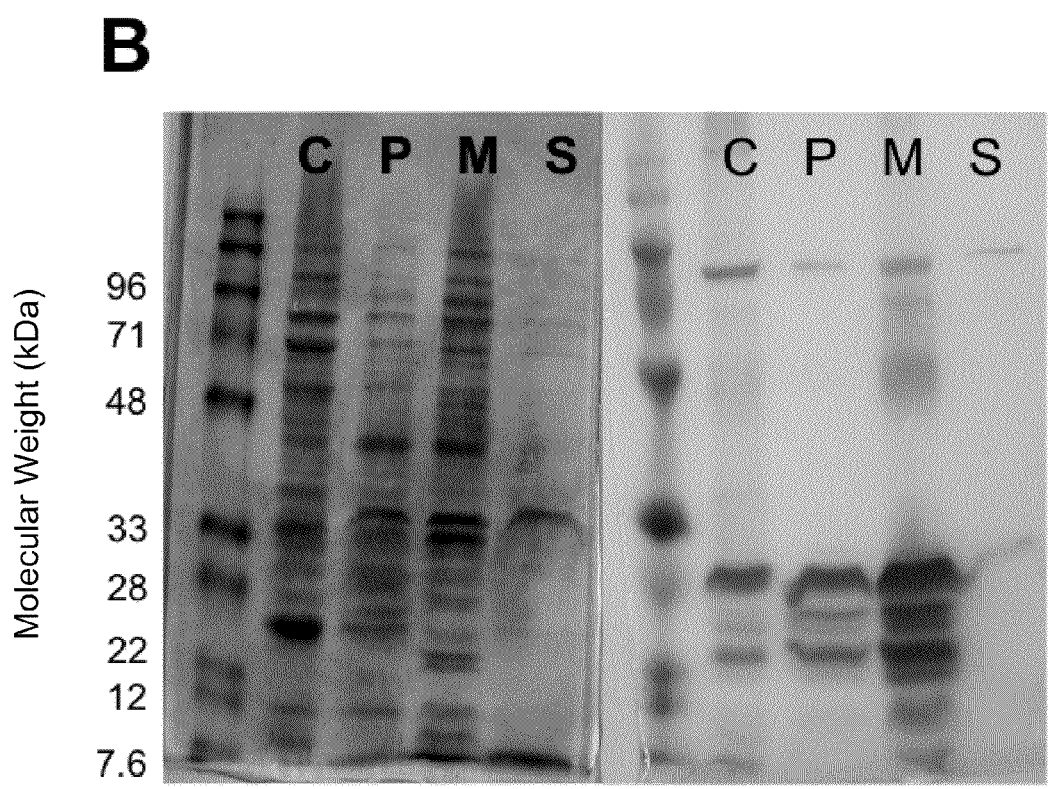
Figure 9:
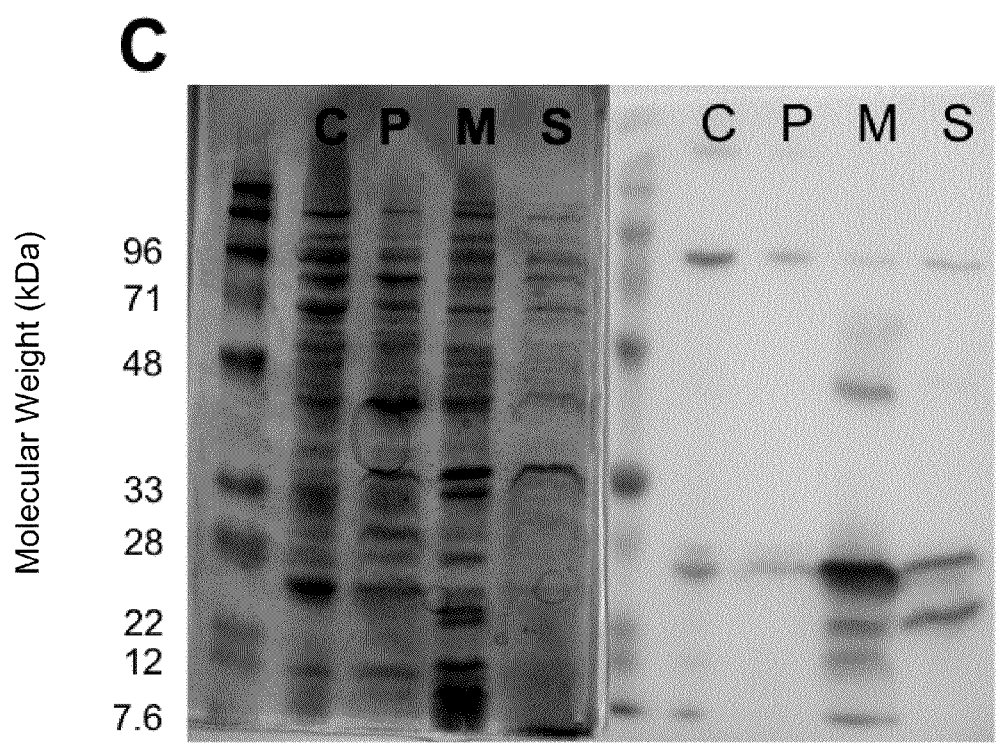
Figure 9:
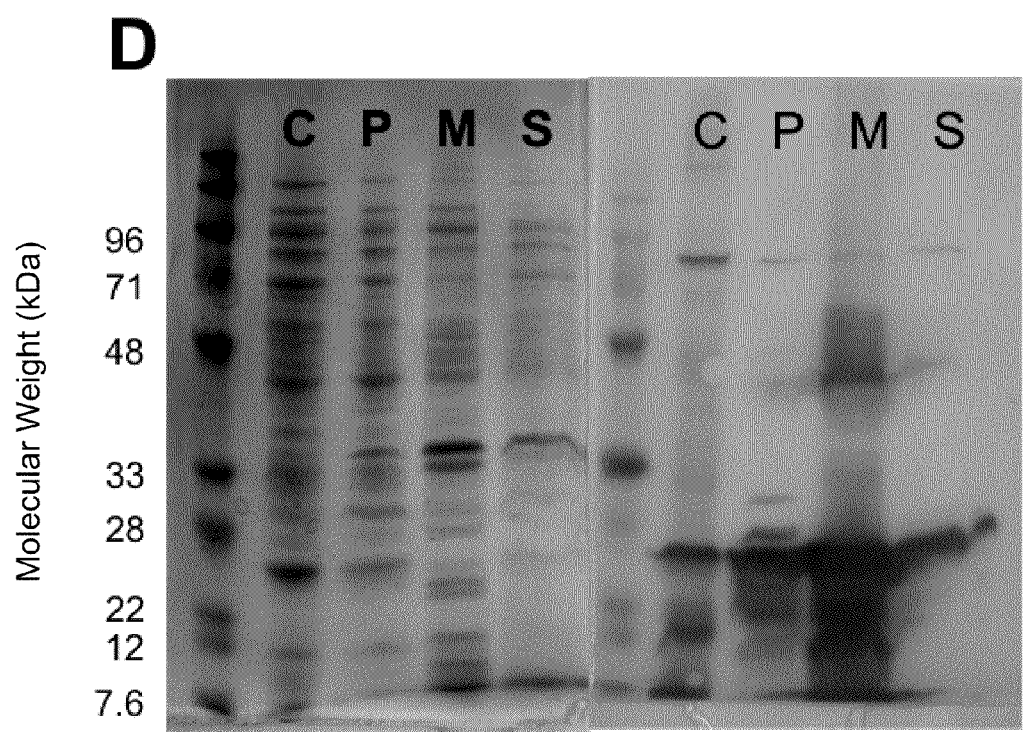

To determine the subcellular localization of these chimeric protein constructs, protein fractions obtained from various subcellular fractionations and from cell free media harvested after 24 hrs of bacteria growth were analyzed by SDS-PAGE and Western blotting. The polyacrylamide gels and corresponding immunoblots for each of the four signal sequence constructs are provided as FIG. 9.

For cells expressing the PhaP1:HlyA construct (FIG. 9A), a strong phasin band is observed at 22 kDa in the concentrated extracellular media. In these same samples, minimal phasin is observed in the cytoplamsic fraction and a strong band is observed in the membrane fraction. This suggests that the expressed phasin is primarily targeted to the HlyA secretion machinery and translocated to the extracellular media.

In analyzed TorA:PhaP1 samples (FIG. 9B), three distinct sizes of phasin were observed, which was consistent to the number and size differences of TorA targeted GFP. The strongest phasin band was observed in the membrane fraction, indicating that some of the targeted protein becomes entrapped in the inner cellular membrane. Periplasmic phasin bands were also observed.

Phasin was primarily found in the membrane fraction and extracellular media when GeneIII was used for targeting (FIG. 9C). Samples obtained from PeIB:PhaP1 harboring cells (FIG. 9D) contained significantly larger quantities of overall phasin. In particular, the membrane fraction had high levels of phasin that is apparent as a single smeared band. Phasin was also detected in the extracellular media. This could mean that the PeIB targeted phasin is expressed at more significant levels.

The functionality of the chimeric polypeptide constructs is shown by SDS-PAGE analysis. Protein bands at 22 kDa corresponding to the size of phasin are observed. The identity of the phasin protein was confirmed using a phasin-specific antibody. Using immunoblotting procedures, phasin translocation was analyzed and results demonstrate phasin export. A significant phasin band was observed in the extracellular media when HlyA was used for targeting. A supernatant band was also observed for GeneIII-targeted phasin. For the TorA, GeneIII, and PeIB signal sequences, significant levels of phasin were found in the membrane fractions. Periplasmic phasin was also observed when TorA was used for targeting.

Example 5

Analysis of Transport of PHB from *E. coli*

*E. coli* XL1-Blue cells harboring the pBHR68 plasmid were shown capable of accumulating as much as 55% of their cell dry weight as bioplastic. XL1-Blue was determined as a suitable candidate for PHA translocation studies, although this strain produces proteases, which may be dealt with if necessary by the addition of protease inhibitors. Scanning electron microscopy (SEM) was used to visualize *E. coli* cells containing various secretion systems (FIGS. 10-12).

Figure 10:
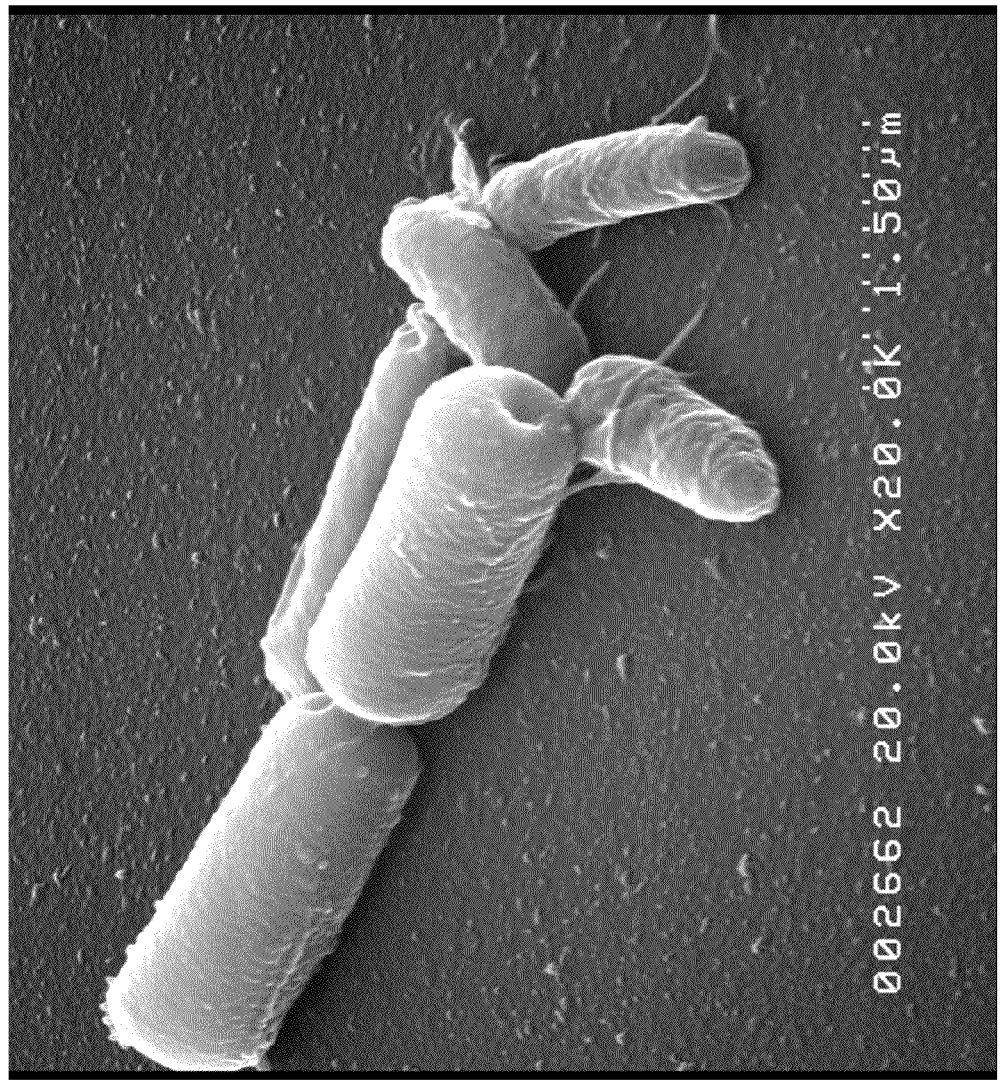
FIG. 10. SEM image of *E. coli* with genes for PHB production. *E. coli* were transformed with pBHR68 and imaged.

Cells containing plasmid pBHR68 that contains the phaCAB genes for PHB production from *Ralstonia eutropha* and no phasin constructs is shown in FIG. 10. As seen in this Figure a large percentage of the cells are fatter than normal (0.7 µM vs 0.3 µM.) This is presumably due to the increase in bioplastic (PHB) accumulation.

Figure 11:
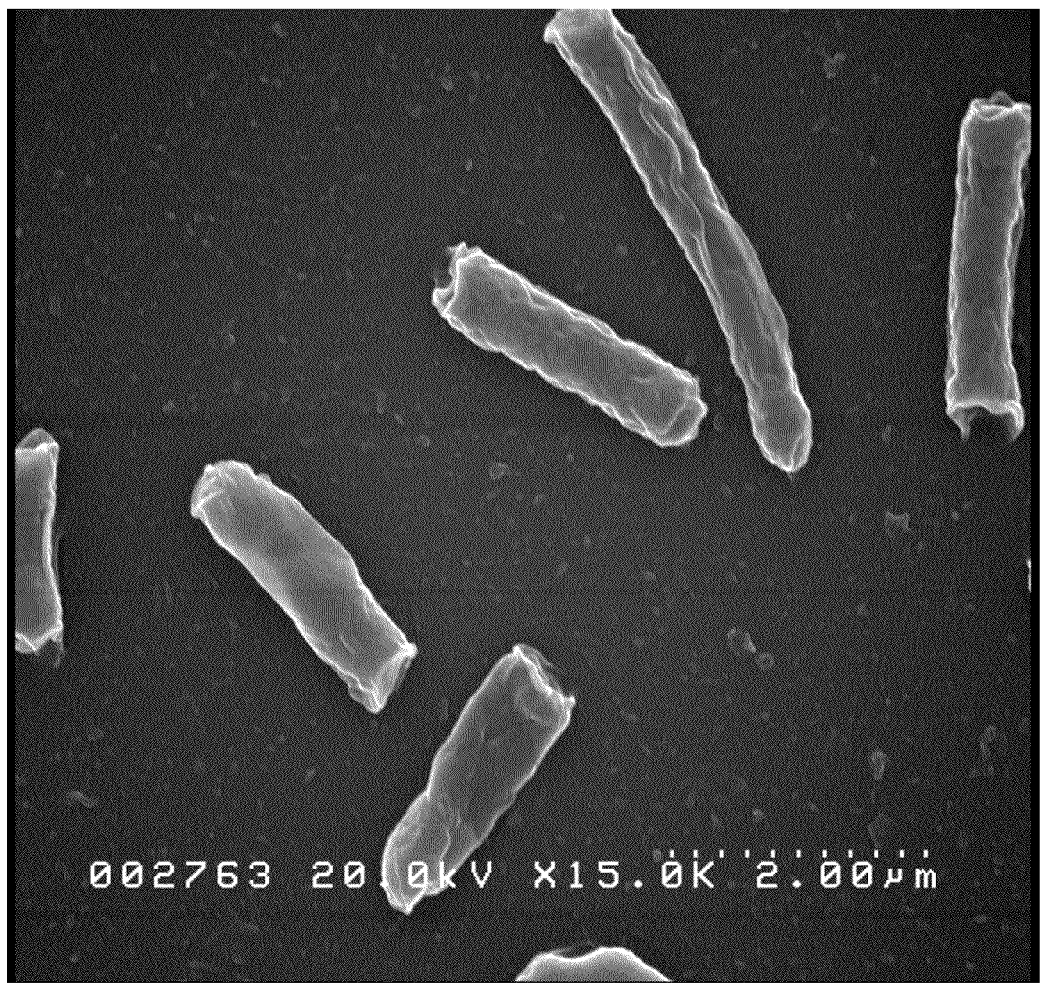
FIG. 11. SEM image of *E. coli* with genes for PHB and phasin production. *E. coli* were transformed with pBHR68 and a plasmid which expresses PhaP1 without a signal sequence.

SEM was performed on *E. coli* cells containing pBHR68 as well as plasmid pSB3K3 expressing the lac-regulated phasin protein without any signal sequence (FIG. 11). Phasin production has previously been shown to reduce PHB granule size.

Figure 13:
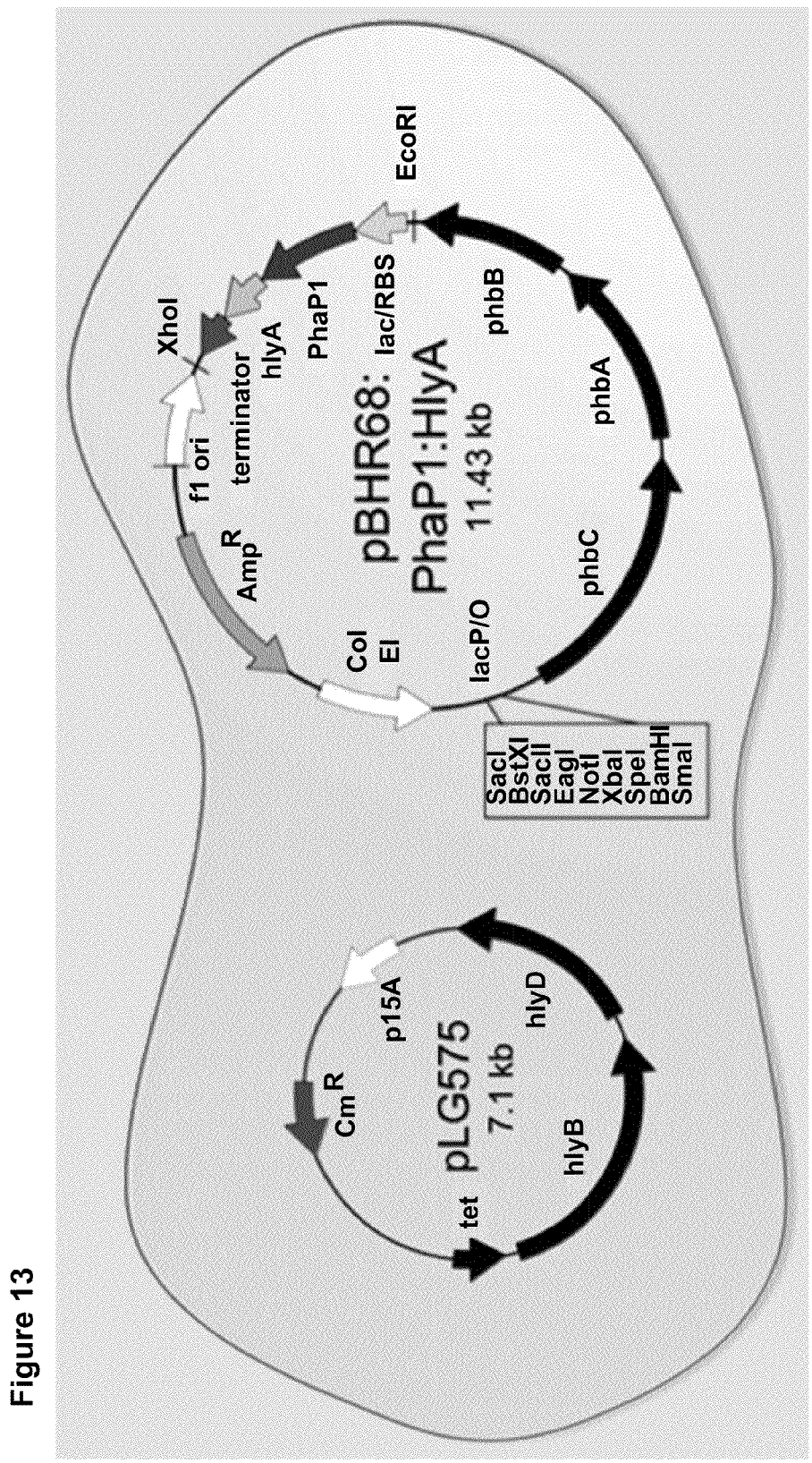
FIG. 13. An illustration of E. coli harboring pLG575 for HlyBD protein expression and pBHR68:PhaP1:HlyA for PHA production and PhaP1:HlyA biofusion expression.
Figure 14A:
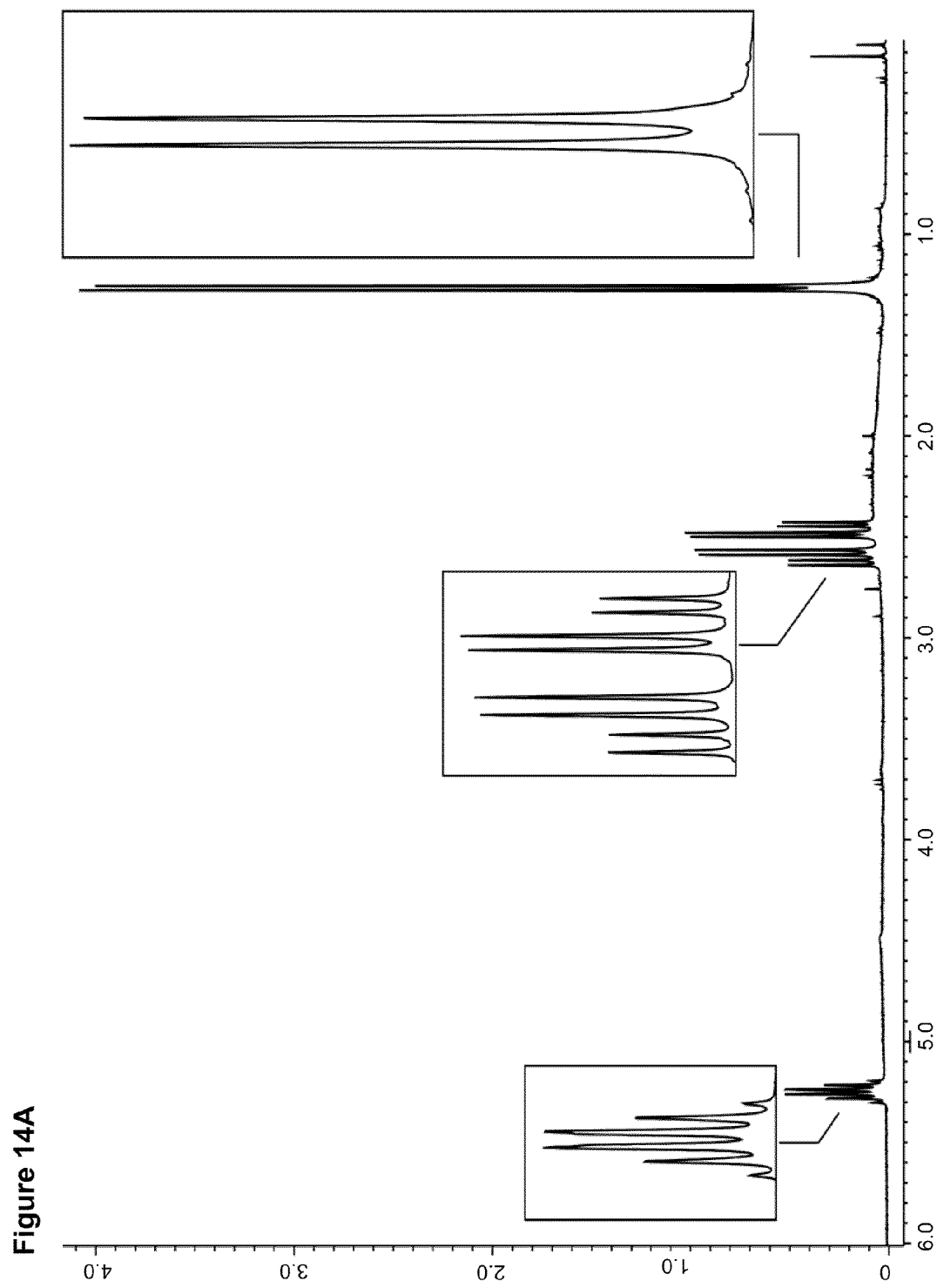
FIG. 14A. Media from E. coli cells containing the entire secretion system except for the secretion tag on the phasin protein (genes for PHB and phasin production).
Figure 14B:
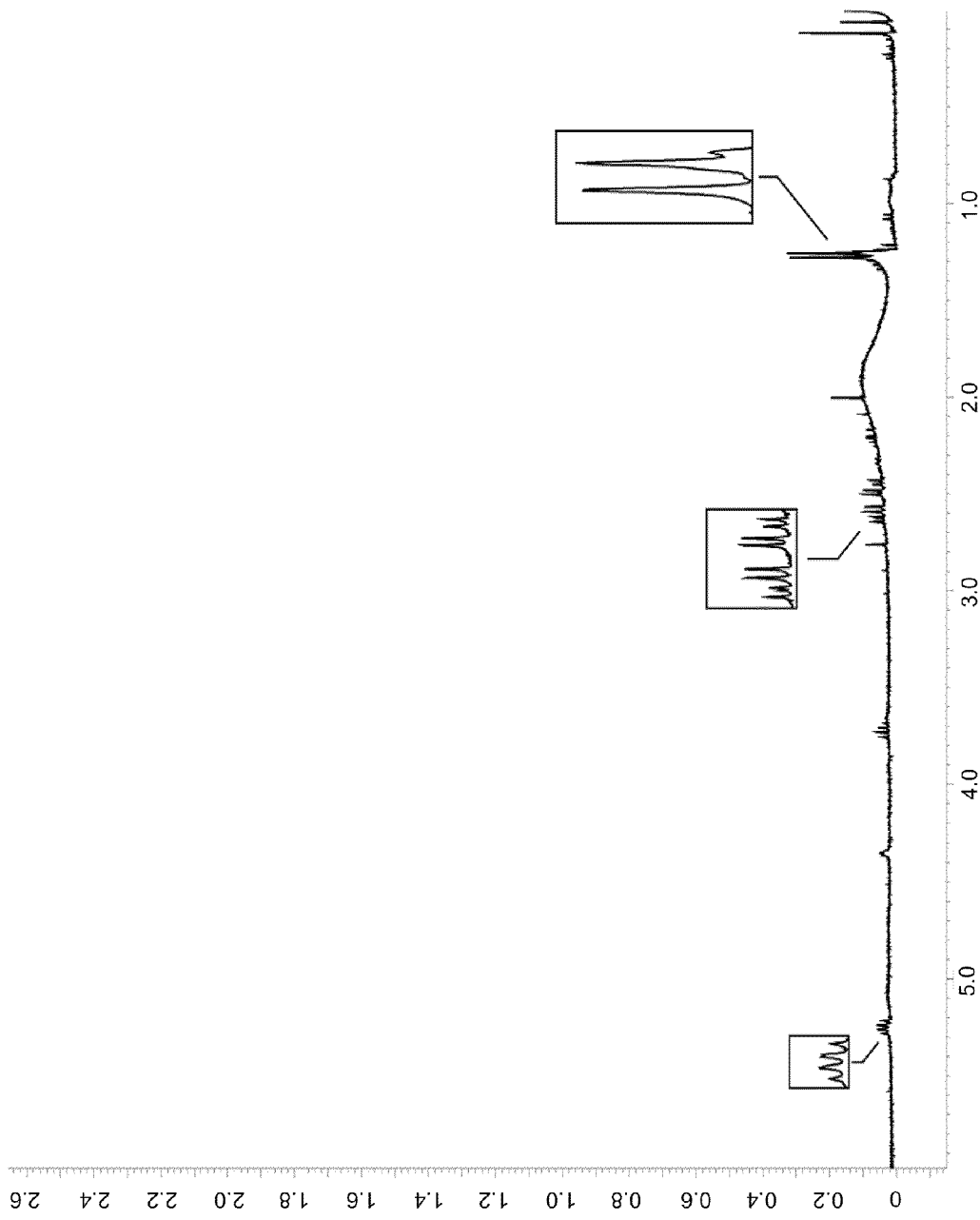
FIG. 14B. Media from E. coli cells containing the entire secretion system (genes for PHB production and ability to secrete phasin/PHB). The NMR signature for PHB is clearly visible in panel B and not in panel A. Note the y-axis for panel A only goes to 0.3 while the y-axis goes to 2.4 for panel B, demonstrating that the peaks in panel A are within the baseline for panel B and are mostly just background signals.

SEM was also performed on cells containing pBHR68: PhaP1:HlyA expressing the PHB synthesis genes phbCAB and phasin with the hlyA signal sequence fused to the carboxyl terminus and pLG575 containing the hlyB and hlyD genes for pore formation (FIG. 12). An illustration of this is shown in FIG. 13. *E. coli* in FIG. 12 are shown secreting PHB in the various panels.

To confirm that the substance transported from the *E. coli* cells is indeed PHB, nuclear magnetic resonance spectra were collected from concentrated supernatants from *E. coli*. Panel A shows concentrated supernatant from cells containing the entire secretion system except for the secretion tag on the phasin protein. Panel B shows concentrated supernatant from cells containing the entire secretion system.

The NMR signature for PHB is clearly visible in panel B and not in panel A. Note the y-axis for panel A only goes to 0.3 while the y-axis goes to 2.4 for panel B, demonstrating that the peaks in panel A are within the baseline for panel B and are mostly just background signals.

Panel A corresponds to cells in FIG. 11 and panel B corresponds to cells in FIG. 12. This data demonstrates that the secretion system is working and that bioplastic is being secreted into the media when the phasin protein has a secretion signal attached.

The invention claimed is:

1. A chimeric polypeptide comprising:
   i. a phasin; and
   ii. a signal sequence
   wherein:
      the phasin is one of SEQ ID NO: 1, 3-6, 31, 72, 84, 88, and 112, and
      the signal sequence is one of SEQ ID NO: 8, 9, 10, 11, 12, 13, 14, 15, 16, 17, 18, 19, 20, 21, 22, or 23.

2. The chimeric polypeptide of claim 1, wherein the signal sequence is N-terminal to the phasin.

3. The chimeric polypeptide of claim 1, wherein the signal sequence is C-terminal to the phasin.

4. The chimeric polypeptide of claim 1, wherein the signal sequence is connected to the phasin.

5. The chimeric polypeptide of claim 1, wherein the polypeptide comprises:
   i. SEQ ID NO: 1; and
   ii. One of SEQ ID NO: 8, 9, 10, 11, or 12.

6. A method of transporting a PHA produced by a cell comprising providing a chimeric polypeptide to the cell, the chimeric polypeptide comprising:
   i. a phasin; and
   ii. a signal sequence
   wherein:
      the phasin is one of SEQ ID NO: 1, 3-6, 31, 72, 84, 88, and 112, and
      the signal sequence is one of SEQ ID NO: 8, 9, 10, 11, 12, 13, 14, 15, 16, 17, 18, 19, 20, 21, 22, or 23.

7. The method of claim 6, wherein the step of providing a chimeric polypeptide to the cell comprises providing to the cell a polynucleotide comprising a sequence which codes for the chimeric polypeptide, wherein the cell expresses the chimeric polypeptide coded for by the polynucleotide.

8. The method of claim 6, wherein the chimeric polypeptide comprises:
   i. SEQ ID NO: 1; and
   ii. a signal sequence selected from SEQ ID NO: 8, 9, 10, 11, or 12.

9. A method of producing a bioplastic comprising:
   providing a cell which produces one or more PHAs;
   providing a chimeric polypeptide to the cell, the chimeric polypeptide comprising
      i. a phasin; and
      ii. a signal sequence; and
   collecting a PHA which has been transported by association with the chimeric polypeptide
   wherein:
      the phasin is one of SEQ ID NO: 1, 3-6, 31, 72, 84, 88, and 112, and
      the signal sequence is one of SEQ ID NO: 8, 9, 10, 11, 12, 13, 14, 15, 16, 17, 18, 19, 20, 21, 22, or 23.

10. The method of claim 9, wherein the step of providing a chimeric polypeptide to the cell comprises providing to the cell a polynucleotide comprising a sequence which codes for the chimeric polypeptide, wherein the cell expresses the chimeric polypeptide coded for by the polynucleotide.

11. The method of claim 9, wherein the chimeric polypeptide comprises:
   i. SEQ ID NO: 1; and
   ii. a signal sequence selected from SEQ ID NO: 8, 9, 10, 11, or 12.

12. The method of claim 9, wherein the PHA is transported outside the cell.

13. The method of claim 9, wherein the cell is a bacterial cell and the PHA is transported to the periplasmic space.

14. The method of claim 9 wherein the cell is maintained in continuous culture.

15. A chimeric polypeptide comprising:
   a phasin comprising SEQ ID NO: 1; and
   a signal sequence comprising SEQ ID NO: 8.

* * * * *